US011157144B2

(12) United States Patent
Gulaka et al.

(10) Patent No.: US 11,157,144 B2
(45) Date of Patent: Oct. 26, 2021

(54) MEDICAL IMAGE PROVIDING APPARATUS AND MEDICAL IMAGE PROCESSING METHOD OF THE SAME

(71) Applicant: SAMSUNG ELECTRONICS CO., LTD., Suwon-si (KR)

(72) Inventors: Praveen Gulaka, Suwon-si (KR); Girish Srinivasan, Seongnam-si (KR); Yeon-ju Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 204 days.

(21) Appl. No.: 16/423,576

(22) Filed: May 28, 2019

(65) Prior Publication Data
US 2019/0278436 A1      Sep. 12, 2019

Related U.S. Application Data

(63) Continuation of application No. 14/839,139, filed on Aug. 28, 2015, now Pat. No. 10,331,298, which is a
(Continued)

(30) Foreign Application Priority Data

Jan. 15, 2014 (KR) .................. 10-2014-0005206
Nov. 11, 2014 (KR) .................. 10-2014-0156244

(51) Int. Cl.
*G06F 3/0482* (2013.01)
*G06F 3/0484* (2013.01)
(Continued)

(52) U.S. Cl.
CPC ............ *G06F 3/0482* (2013.01); *A61B 6/032* (2013.01); *A61B 6/463* (2013.01); *A61B 6/469* (2013.01);
(Continued)

(58) Field of Classification Search
CPC .......... A61B 6/00; A61B 6/032; A61B 6/469; A61B 6/463; A61B 6/5229; A61B 5/055;
(Continued)

(56) References Cited

U.S. PATENT DOCUMENTS 5,332,968 A    7/1994 Brown
5,482,045 A    1/1996 Rust et al.
(Continued)

FOREIGN PATENT DOCUMENTS

CN    1671325 A    9/2005
CN    1985258 A    6/2007
(Continued)

OTHER PUBLICATIONS

Communication dated Jan. 18, 2019 issued by the European Intellectual Property Office in counterpart European Application No. 15 737 905.8.
(Continued)

*Primary Examiner* — Anil K Bhargava
(74) *Attorney, Agent, or Firm* — Sughrue Mion, PLLC

(57) ABSTRACT

A medical image providing apparatus includes: a display configured to display a first image including an object; and a processor configured to control to output a first list for selecting a medical image reconstruction technique to generate a second image based on a first region included in the first image being selected, receive a selection of the medical image reconstruction technique, and to control to overlay and display the second image generated by applying the selected medical image reconstruction technique on the first region of the first image.

18 Claims, 37 Drawing Sheets
(4 of 37 Drawing Sheet(s) Filed in Color)

Related U.S. Application Data continuation of application No. 14/597,793, filed on Jan. 15, 2015, now Pat. No. 9,582,152.

(51) Int. Cl.
*A61B 6/00* (2006.01)
*G16H 40/63* (2018.01)
*G16H 30/40* (2018.01)
*A61B 6/03* (2006.01)
*G06T 11/00* (2006.01)
*A61B 5/055* (2006.01)

(52) U.S. Cl.
CPC ........ *A61B 6/5229* (2013.01); *G06F 3/04845* (2013.01); *G06T 11/003* (2013.01); *G16H 30/40* (2018.01); *G16H 40/63* (2018.01); *A61B 5/055* (2013.01); *A61B 2576/026* (2013.01)

(58) Field of Classification Search
CPC ............. A61B 2576/026; G06F 3/0482; G06F 3/0485; G16H 30/40; G06T 11/003
See application file for complete search history.

(56) References Cited

U.S. PATENT DOCUMENTS

| | | | |
|---|---|---|---|
| 6,685,642 B1 | 2/2004 | Garg et al. | |
| 7,145,336 B2 | 12/2006 | Brown | |
| 7,502,445 B2* | 3/2009 | Shi | A61B 6/469 378/115 |
| 7,689,266 B2 | 3/2010 | Shinohara et al. | |
| 8,090,429 B2 | 1/2012 | Vija et al. | |
| 8,313,432 B2 | 11/2012 | Chiu et al. | |
| 8,488,860 B2 | 7/2013 | Uchizono et al. | |
| 8,712,798 B2 | 4/2014 | Gotman et al. | |
| 8,951,266 B2 | 2/2015 | Zingaretti et al. | |
| 9,299,313 B2 | 3/2016 | Goto et al. | |
| 2003/0016850 A1 | 1/2003 | Kaufman et al. | |
| 2004/0068170 A1 | 4/2004 | Wang et al. | |
| 2005/0089205 A1 | 4/2005 | Kapur et al. | |
| 2005/0245804 A1 | 11/2005 | Shinohara et al. | |
| 2006/0064396 A1 | 3/2006 | Wei et al. | |
| 2006/0245651 A1* | 11/2006 | Quinion | G16H 70/60 382/181 |
| 2007/0016018 A1 | 1/2007 | Kinicki | |
| 2007/0109294 A1* | 5/2007 | Gotman | A61B 6/467 345/418 |
| 2007/0127792 A1* | 6/2007 | Virtue | A61B 6/463 382/128 |
| 2008/0008401 A1 | 1/2008 | Zhu et al. | |
| 2008/0049996 A1* | 2/2008 | Marshall | G06T 7/0012 382/128 |
| 2008/0072151 A1 | 3/2008 | Song et al. | |
| 2008/0089584 A1 | 4/2008 | VanMetter et al. | |
| 2008/0177172 A1* | 7/2008 | John | A61B 90/36 600/413 |
| 2009/0213034 A1 | 8/2009 | Wu et al. | |
| 2009/0264753 A1 | 10/2009 | von Schulthess et al. | |
| 2010/0166274 A1* | 7/2010 | Busch | A61B 6/037 382/131 |
| 2010/0201708 A1 | 8/2010 | Dresel et al. | |
| 2010/0235352 A1* | 9/2010 | Slutsky | G06T 7/37 707/723 |
| 2010/0312094 A1 | 12/2010 | Guttman et al. | |
| 2011/0015520 A1* | 1/2011 | Meetz | A61B 6/507 600/425 |
| 2011/0210734 A1* | 9/2011 | Darrow | G06K 9/6284 324/309 |
| 2011/0288400 A1 | 11/2011 | Russell et al. | |
| 2011/0313268 A1 | 12/2011 | Kokones et al. | |
| 2012/0010475 A1 | 1/2012 | Rossmeier et al. | |
| 2012/0123253 A1* | 5/2012 | Renisch | A61B 6/5247 600/425 |
| 2012/0131498 A1 | 5/2012 | Gross et al. | |
| 2012/0172700 A1* | 7/2012 | Krishnan | G16H 30/20 600/407 |
| 2012/0179189 A1 | 7/2012 | Zingaretti et al. | |
| 2013/0039559 A1* | 2/2013 | Grass | G06T 7/32 382/131 |
| 2013/0187903 A1 | 7/2013 | Papageorgiou et al. | |
| 2013/0303911 A1 | 11/2013 | Lee et al. | |
| 2013/0343508 A1 | 12/2013 | Hagiwara | |
| 2014/0086471 A1 | 3/2014 | Ruth et al. | |
| 2014/0098932 A1* | 4/2014 | Profio | A61B 6/032 378/19 |
| 2014/0343400 A1 | 11/2014 | Takayama et al. | |
| 2015/0025372 A1* | 1/2015 | Ghosh | A61B 6/032 600/431 |
| 2015/0070016 A1* | 3/2015 | Ooshima | A61B 6/469 324/309 |
| 2019/0278436 A1 | 9/2019 | Gulaka et al. | |

FOREIGN PATENT DOCUMENTS

| | | |
|---|---|---|
| CN | 101076724 A | 11/2007 |
| CN | 101224114 A | 7/2008 |
| CN | 101978375 A | 2/2011 |
| CN | 102048540 A | 5/2011 |
| CN | 102525523 A | 7/2012 |
| CN | 102985012 A | 3/2013 |
| CN | 103269657 A | 8/2013 |
| CN | 105142513 A | 12/2015 |
| CN | 106725571 A | 5/2017 |
| EP | 1953566 A1 | 8/2008 |
| JP | 2012-249676 A | 12/2012 |
| KR | 10-2008-0053057 A | 6/2008 |
| WO | 98/47085 A2 | 10/1988 |
| WO | 00/51484 A2 | 9/2000 |
| WO | 2010096438 A2 | 8/2010 |
| WO | 2011/044295 A2 | 4/2011 |
| WO | 2012/117381 A1 | 9/2012 |
| WO | 2013/161911 A1 | 10/2013 |
| WO | 2013191036 A1 | 12/2013 |

OTHER PUBLICATIONS

Chinese Office Action dated Jan. 16, 2019 issued by the State Intellectual Property Office of P.R. China in counterpart Chinese Application No. 201611257370.9.
Communication dated Apr. 26, 2018 by the European Patent Office in counterpart European Patent Application No. 15737905.8.
Communication dated Oct. 10, 2017, issued by the European Patent Office in counterpart application No. 15 188 808.8.
Communication dated Aug. 31, 2017, issued by the State Intellectual Property Office of P.R. China in counterpart Chinese application No. 201580000391.X.
Communication from the Korean Intellectual Property Office dated Dec. 14, 2015 in a counterpart Korean application No. 10-2014-0156244.
Communication from the European Patent Office dated Feb. 4, 2016 in a counterpart European Application No. 15737905.8.
Communication from the European Patent Office dated Feb. 4, 2016 in a counterpart European Application No. 15188808.8.
Communication dated Apr. 23, 2015, issued by the International Searching Authority in counterpart International Application No. PCT/KR2015/000273.
Communication dated Nov. 3, 2016, issued by the European Patent Office in counterpart European Application No. 15188808.8.
Communication dated Nov. 30, 2016, issued by the European Patent Office in counterpart European Application No. 15737905.8.
Philips CT Marketing, "Philips' top-ranked Brilliance Workspace excels at Stanford's workstation face-off", NetForum Community, available at <http://clinical.netforum.healthcare.philips.com/us_en/Explore/Clinical-News/CT/Philips-top-ranked-Brilliance-Workspace-excels-at-Stanfords-workstation-face-off> , Jul. 30, 2009, Total 2 pages.
Philips CT Marketing, "Lung lesion ", NetForum Community, available at <http://acceptance.netforum.healthcare.philips.com/Clinical/global/Explore/Case-Studies/CT/Lung-lesion>, Jul. 10, 2009, Total 2 pages.

(56) References Cited

OTHER PUBLICATIONS

Communication dated Jun. 26, 2019, issued by the European Patent Office in counterpart European Application No. 19173691.7.
Communication dated Jul. 19, 2021, issued by the State Intellectual Property Office of P.R. China in counterpart Chinese Application No. 201810421024.2.

* cited by examiner

FIG. 28A
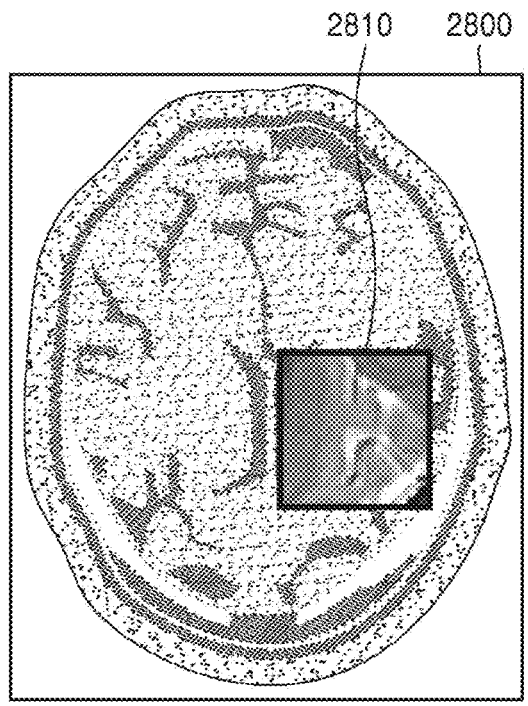
FIG. 28B
FIG. 28C
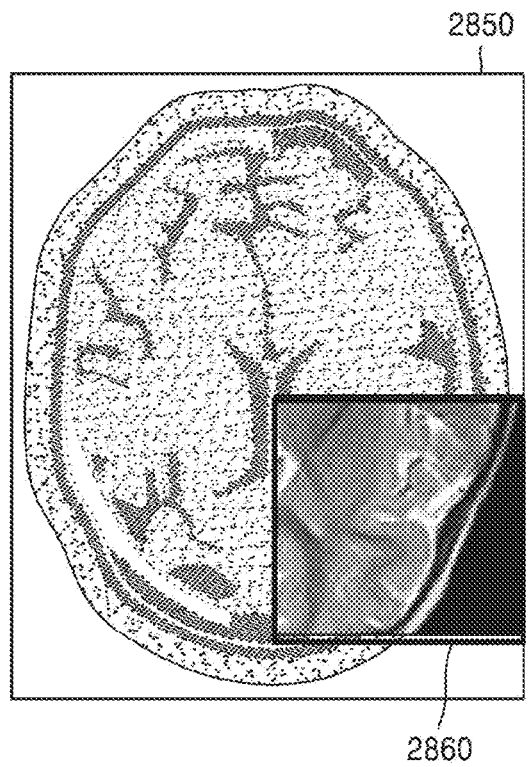
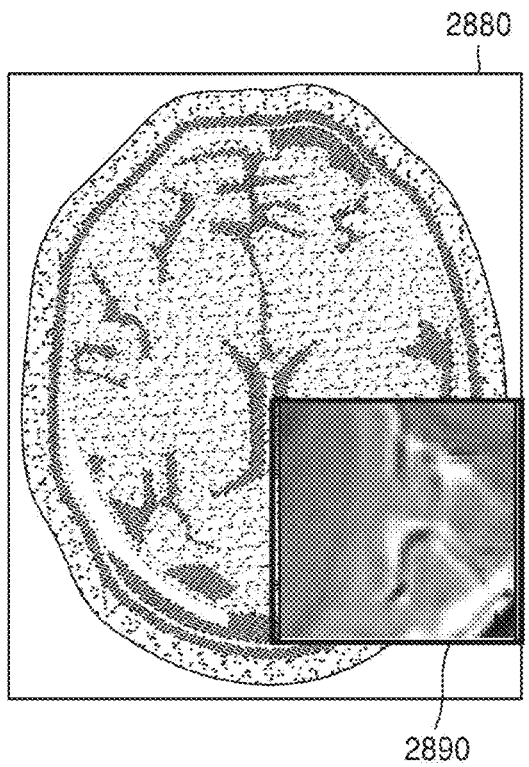

FIG. 29
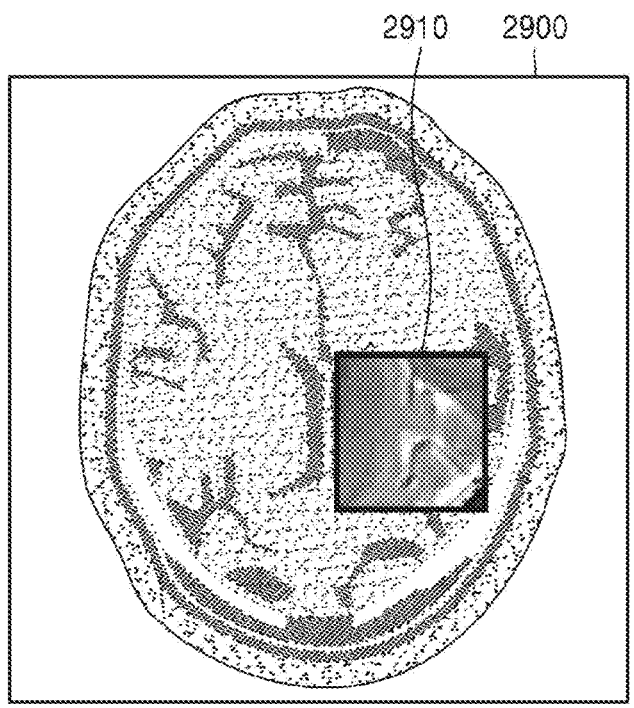
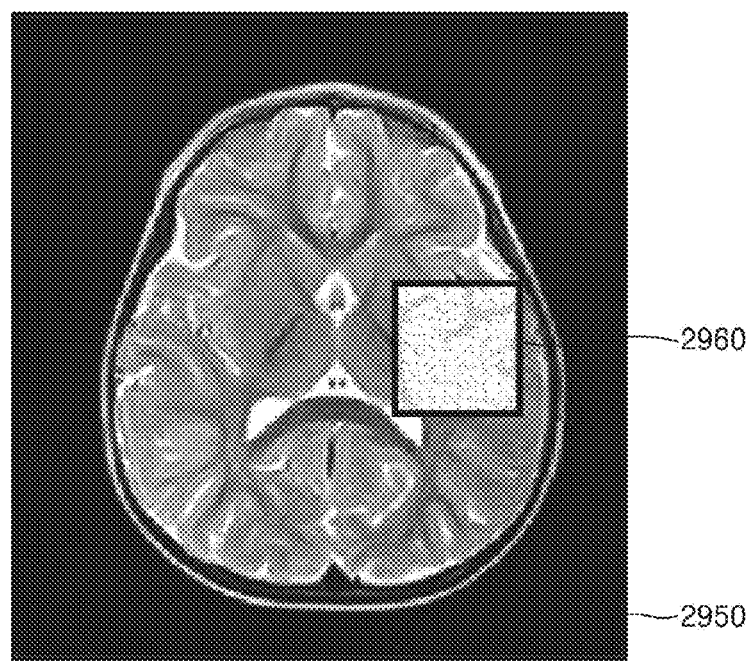

MEDICAL IMAGE PROVIDING APPARATUS AND MEDICAL IMAGE PROCESSING METHOD OF THE SAME

CROSS-REFERENCE TO RELATED APPLICATIONS

This is a continuation of U.S. application Ser. No. 14/839,139, which is a continuation of U.S. application Ser. No. 14/597,793 which claims priority from Korean Patent Application Nos. 10-2014-0005206, filed on Jan. 15, 2014, and 10-2014-0156244, filed on Nov. 11, 2014, in the Korean Intellectual Property Office, the disclosures of which are incorporated herein by reference in their entireties.

BACKGROUND

1. Field

One or more exemplary embodiments relate to a medical image providing apparatus for displaying a screen including a medical image and a medical image processing method of the same.

2. Description of the Related Art

A medical imaging apparatus is an apparatus used to obtain an image of an internal structure of an object. The medical imaging apparatus is a noninvasive examination apparatus that photographs and processes structural details in a body, internal tissues of the body, and flow of body fluids to show them to a user. The user, such as a doctor, may determine a health condition of a patient and diagnose a disease by using a medical image output from the medical imaging apparatus.

Examples of the medical imaging apparatus include a magnetic resonance imaging (MRI) apparatus for providing a magnetic resonance (MR) image, a computed tomography (CT) apparatus, an X-ray apparatus, and an ultrasound diagnostic apparatus.

An MRI apparatus is an apparatus for photographing a subject by using a magnetic field, and is widely used to accurately diagnose diseases since the MRI apparatus provides three-dimensional images showing bones, discs, joints, nerves, and ligaments at a desired angle.

The MRI apparatus obtains an MR signal by using a permanent magnet, a gradient coil, and a high frequency multi-coil including radio frequency (RF) coils. Then, the MRI apparatus samples the MR signal to restore the MR image.

A CT apparatus, which is one of the medical imaging apparatuses, is widely used to accurately diagnose a disease since the CT apparatus is capable of providing a sectional image of an object and is capable of distinctively expressing an internal structure, for example, organs such as a kidney and lungs, of the object, as compared to a general X-ray apparatus.

The CT apparatus irradiates an X-ray on the object, detects the X-ray that passed through the object, and then restores an image by using the detected X-ray.

As described above, medical images obtained by using various medical imaging apparatuses express an object in various methods according to types and photographing methods of the various medical imaging apparatuses.

A doctor determines a disease or a health disorder of a patient by reading a medical image. Accordingly, a medical imaging apparatus for diagnosis may be provided to the doctor such that the doctor may select and read a suitable medical image to diagnose the patient.

SUMMARY

One or more exemplary embodiments include a medical image providing apparatus for providing a medical image suitable for an intention of a user and a medical image processing method of the same.

One or more exemplary embodiments include a medical image providing apparatus for providing a medical image or a user interface (UI) screen including the medical image such that a user easily diagnoses a disease of a patient and a medical image processing method of the same.

Additional aspects will be set forth in part in the description which follows and, in part, will be apparent from the description, or may be learned by practice of the exemplary embodiments.

According to an aspect of an exemplary embodiment, a medical image providing apparatus includes: a display unit for displaying a first image including an object; a UI unit for, outputting a first list including at least one protocol applied while scanning the object in response to a first region included in the first image being selected, and receiving a selection on a first protocol included in the first list; and a control unit for controlling a second image reconstructed by using image data obtained by applying the first protocol to be overlaid and displayed on the first region of the first image.

The second image may be an image corresponding to a predetermined region of the object included in the first region.

The at least one protocol may be a protocol related to a pulse sequence applied to obtain the image data.

The protocol may include a magnetic resonance imaging (MRI) protocol.

The protocol may include a computed tomography (CT) protocol.

The UI unit may receive a setting on a region of interest (ROI) as the first region in the first image from a user.

The control unit may automatically extract a target region for diagnosis from the first image and select the target region as the first region.

The control unit may automatically perform an organ segmentation on the first image to obtain a segmented region and select the segmented region as the first region.

The control unit may automatically extract a disease suspected region from the first image and select the disease suspected region as the first region.

The first list may include a first sub-list including the at least one protocol, and a second sub-list including at least one manipulation menu item for manipulating the first region of the first image.

The UI unit may control the first and second sub-lists to be separately displayed.

The first list may include a magnetic resonance imaging (MRI) list including at least one protocol for scanning an MRI image, and a computed tomography (CT) list including at least one protocol for scanning a CT image.

The UI unit may generate at least one manipulation menu item for respectively manipulating at least one reconstructed image reconstructed by using at least one piece of image data obtained by applying each of the at least one protocol, and add and output the at least one manipulation menu item to the at least one protocol included in the first list.

Each item included in the first list may include a protocol and a reconstructed image reconstructed by using image data obtained by applying the protocol.

The medical image providing apparatus may further include a memory for storing at least one piece of image data obtained by applying each of the at least one protocol.

The control unit may read image data corresponding to the first protocol from the memory and generate the second image by using the read image data in response to the first protocol is selected.

The medical image providing apparatus may further include a memory for storing at least one reconstructed image respectively reconstructed by using at least one piece of image data obtained by applying the at least one protocol.

The control unit may read a reconstructed image corresponding to the first protocol from the memory, and control the second image to be overlaid on the first region by using the read reconstructed image in response to the first protocol being selected.

The at least one protocol may include at least one of an MRI protocol, a T1 period-related protocol, a T2 period-related protocol, a diffusion protocol, and a perfusion protocol.

The first list may include at least one additional item obtained or calculated by using at least one piece of image data obtained by applying the at least one protocol.

The additional item may include at least one of a cerebral blood volume (CBV) map, a cerebral blood flow (CBF) map, a histogram equalization image, an apparent diffusion coefficient (ADC) map, and a trace map.

The UI unit may add and output a sub-list including at least one reconstructed image according to at least one point in time, which corresponds to a protocol included in each item included in the first list, to each item included in the first list.

The UI unit may include an input device for receiving a predetermined command from a user, and the control unit may control a preview menu on a reconstructed image corresponding to a predetermined item included in the first list in response to the predetermined item being focused on by the input device.

The UI unit may receive a selection on a protocol corresponding to each of the plurality of first regions in response to a plurality of the first regions that are a plurality of partial regions included in the first image being selected.

The first list may include at least one of a plurality of anatomical image items corresponding to a protocol, and a plurality of functional image items corresponding to a protocol.

The first list may separately display the plurality of anatomical image items and the plurality of functional image items.

The control unit may control a type of an image displayed in the first region and a type of the first image to be mutually switched and displayed, according to a user request.

The control unit may change a type of an image overlaid on the first region of which a location is changed in response to the second image being overlaid on the first region of the first image and then a location of the first region being requested to be changed.

According to an aspect of another exemplary embodiment, a medical image providing apparatus includes: a display unit for displaying a first image including an object; a UI unit for, outputting a first list including at least one reconstructed image that is reconstructed by using at least one piece of image data obtained by applying at least one protocol applied while scanning the object in response to a first region included in the first image being selected, and receiving a selection on a first reconstructed image included in the first list; and a control unit for controlling a second image to be overlaid and displayed on the first region of the first image, by using the first reconstructed image.

The control unit may control a region of the first reconstructed image, which corresponds to the first region, to be overlaid and displayed on the first region.

The at least one reconstructed image included in the first list may be a whole image corresponding to the object.

The at least one reconstructed image included in the first list may be a partial image corresponding to a predetermined region of the object, which is included in the first region.

The at least one protocol may include at least one of a magnetic resonance imaging (MRI) protocol related to a pulse sequence applied to obtain the image data and a computed tomography (CT) protocol applied during a CT scan.

The control unit may automatically extract or select the first region from the first image.

Each item included in the first list may include a first sub-list including the at least one reconstructed image, and a second sub-list including at least one manipulation menu item for manipulating the first region of the first image.

The UI unit may control the first and second sub-lists to be separately displayed.

The first list may include a second sub-list including at least one of an MRI list including at least one reconstructed magnetic resonance imaging (MRI) image reconstructed by using image data obtained by applying a protocol for scanning an MRI image, and a computed tomography (CT) list including at least one reconstructed CT image reconstructed by using image data obtained by applying a protocol for scanning a CT image.

The UI unit may generate at least one manipulation menu item for manipulating each of the at least one reconstructed image, and add and output the at least one manipulation menu item to each of the at least one reconstructed image included in the first list.

Each item included in the first list may include a protocol and a reconstructed image reconstructed by using image data obtained by applying the protocol.

The medical image providing apparatus may further include a memory for storing the at least one reconstructed image.

The at least one protocol may include at least one of an MRI protocol, a T1 period-related protocol, a T2 period-related protocol, a diffusion protocol, and a perfusion protocol.

The first list may include at least one additional image generated by using at least one piece of image data obtained by applying the at least one protocol.

The additional image may include at least one of a cerebral blood volume (CBV) map, a cerebral blood flow (CBF) map, a histogram equalization image, an apparent diffusion coefficient (ADC) map, a trace map, a functional MRI (fMRI) map, a fractional anisotropy map, and a diffusion tractography image.

Each item of the first list may include at least one reconstructed image according to at least one point in time, which corresponds to a protocol included in each item of the first list.

When a second reconstructed image included in the first list is activated, the controller may control a second list including at least one reconstructed image related to a first protocol applied to obtain the second reconstructed image to be output.

The second list may include at least one reconstructed image that is obtained, calculated, or post-processed by using at least one piece of image data obtained according to the first protocol.

According to an aspect of another exemplary embodiment, a medical image providing apparatus includes: a display unit for displaying a first image including an object; a UI unit for receiving a selection on a first region in the first image; and a control unit for controlling a second image reconstructed by using first image data obtained by scanning the object to overlay and be displayed on the first region in the first image.

The control unit may select the predetermined protocol from among a plurality of protocols for scanning the object, based on a region of the object, which is included in the first region of the first image.

The medical image providing apparatus may further include a memory for storing at least one piece of image data obtained by scanning the object by applying at least one protocol.

The control unit may select the predetermined protocol from among the at least one protocol, read image data corresponding to the predetermined protocol from the memory, and generate the second image by using the read image data, based on the region of the object.

The medical image providing apparatus may further include a memory for storing at least one reconstructed image reconstructed by using at least one piece of image data obtained by scanning the object by applying at least one protocol.

The control unit may select the predetermined protocol from among the at least one protocol, read a reconstructed image corresponding to the predetermined protocol from the memory, and generate the second image by using the read reconstructed image, based on a region of the object, which is included in the first region.

According to an aspect of another exemplary embodiment, a medical image providing apparatus includes: a display unit for displaying a screen including a first list including at least one protocol applied while scanning an object; a UI unit for receiving a selection on a first protocol from the first list; and a control unit for setting a first region in a first image including an object after the selection on the first protocol, and controlling to overlay and display a second image reconstructed by using image data obtained by applying the first protocol, on the first region.

The UI unit may receive a setting on a region of interest (ROI) as the first region on the first image included in the screen from a user, and the control unit may set the ROI as the first region.

The first list may include at least one of a plurality of anatomical image items corresponding to a protocol, and a plurality of functional image items corresponding to a protocol.

According to an aspect of another exemplary embodiment, a medical image providing apparatus includes: a display unit for displaying a first image including an object; a UI unit for, outputting a first list including at least one of an image item obtained by using the first image in response to a first region being selected from the first image, and receiving a selection on a predetermined item included in the first list; and a control unit for controlling a second image corresponding to the predetermined item to be overlaid and displayed on the first region.

The first list may include at least one image item calculated or post-processed by using image data obtained by applying a protocol corresponding to the first image.

According to an aspect of another exemplary embodiment, a method for controlling a medical image providing apparatus is provided. The method includes: displaying a first image including a medical image; displaying a first list including at least one item corresponding to a protocol applied to the first image in response to a first region of the first image being selected; and overlaying a second image on the first image in response to receiving a selection of an item from the first list.

The at least one item may include a protocol and a reconstructed image obtained by applying the protocol.

The at least one item corresponding to the protocol applied to the first image may include a first item corresponding to a magnetic resonance imaging (MRI) protocol and second item corresponding to a computed tomography (CT) protocol.

The method may further include automatically extracting a disease suspected region from the first image and selecting the disease suspected region as the first region.

The method may further include performing organ segmentation on the first image to obtain a segmented region and selecting the segmented region as the first region.

The method may further include storing at least one reconstructed image obtained by applying the protocol.

The method may further include receiving a setting on a region of interest (ROI) as the first region in the first image from a user via the UI.

Each item included in the first list may include a protocol and a reconstructed image reconstructed by using image data obtained by applying the protocol.

According to an aspect of another exemplary embodiment, a medical image processing method includes: displaying a first image including an object; when a first region included in the first image is selected, outputting a first list including at least one protocol applied while scanning the object; receiving a selection of a first protocol included in the first list via a UI; and overlaying and displaying a second image reconstructed by using image data obtained by applying the first protocol, on the first region of the first image.

According to an aspect of another exemplary embodiment, a medical image processing method includes: displaying a first image including an object; when a first region included in the first image is selected, outputting a first list including at least one reconstructed image that is reconstructed by using at least one piece of image data obtained by applying at least one protocol applied while scanning the object; receiving a selection of a first reconstructed image included in the first list via a UI; and overlaying and displaying a second image on the first region of the first image by using the first reconstructed image.

According to an aspect of another exemplary embodiment, a medical image processing method includes: displaying a first image including an object; receiving a selection of a first region of the first image via a UI; and overlaying and displaying a second image reconstructed by using first image data obtained by scanning the object by applying a first protocol, on the first region of the first image.

According to an aspect of another exemplary embodiment, a medical image processing method including: displaying a screen including a first list including at least one protocol applied while scanning an object; receiving a selection of a first protocol from the first list via a UI; setting a first region in a first image including the object after the selection of the first protocol; and overlaying and displaying a second image reconstructed by using image data obtained by applying the first protocol, on the first region.

According to an aspect of another exemplary embodiment, a medical image processing method includes: displaying a first image including an object; when a first region is selected from the first image, outputting a first list including at least one image item obtained by using the first image; receiving a selection of a certain item included in the first list via a UI; and overlaying and displaying a second image corresponding to the certain item on the first region.

BRIEF DESCRIPTION OF THE DRAWINGS

The patent or application file contains at least one drawing executed in color. Copies of this patent or patent application publication with color drawings will be provided by the Office upon request and payment of the necessary fee. These and/or other aspects will become apparent and more readily appreciated from the following description of the embodiments, taken in conjunction with the accompanying drawings in which:

FIGS. 28A, 28B, and 28C show diagrams for describing operations of a medical image providing apparatus, according to another exemplary embodiment;

FIG. 29 is a diagram for describing operations of a medical image providing apparatus, according to another exemplary embodiment;

DETAILED DESCRIPTION

Figure 1:
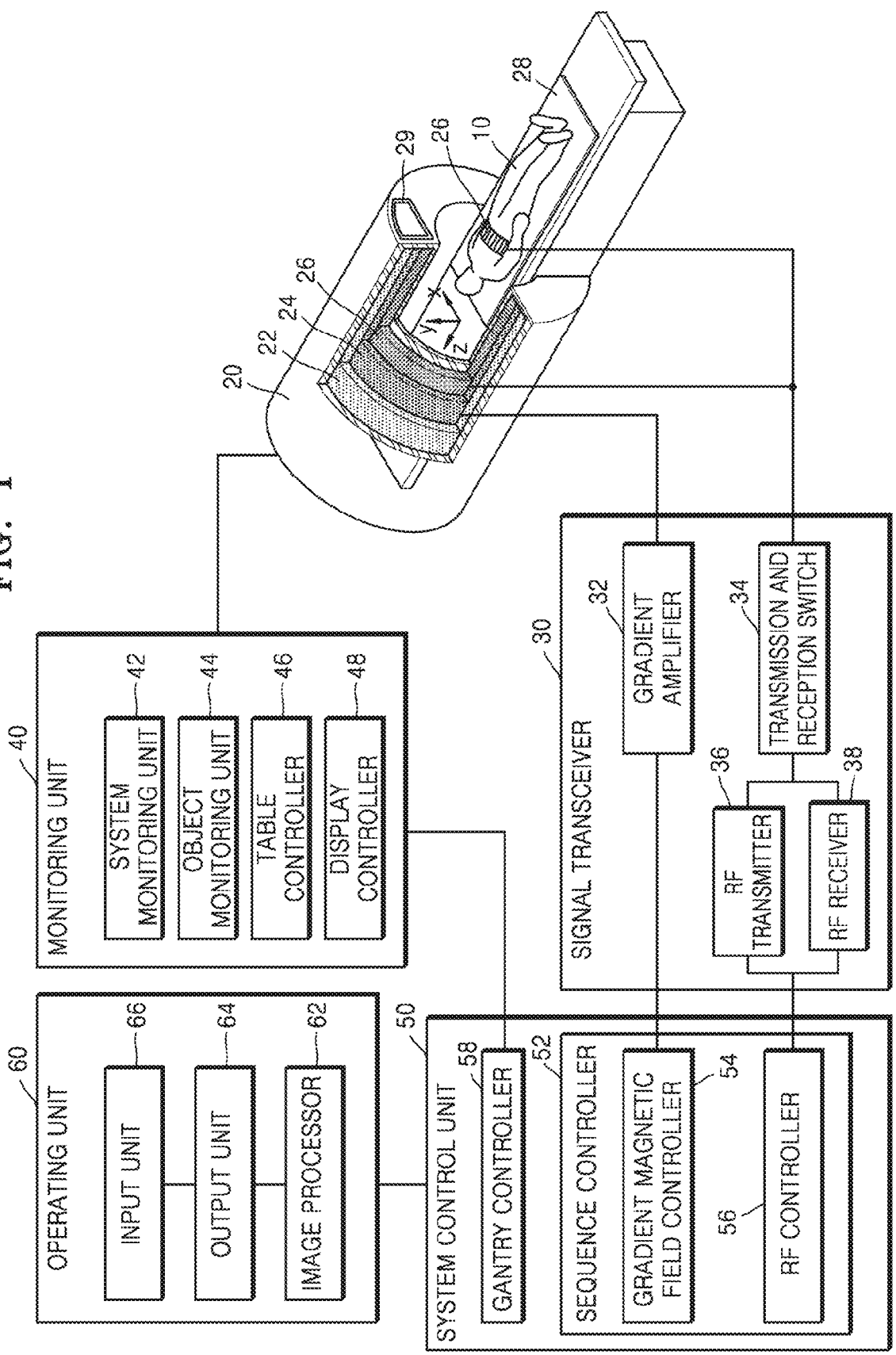
FIG. 1 is a schematic diagram of a general magnetic resonance imaging (MRI) system.

One or more exemplary embodiments will now be described more fully with reference to the accompanying drawings. The exemplary embodiments may, however, be embodied in many different forms and should not be construed as being limited to the embodiments set forth herein; rather, these embodiments are provided so that this disclosure will be thorough and complete, and will fully convey the concept of the exemplary embodiments to those skilled in the art.

Terms used herein will now be briefly described and then one or more exemplary embodiments will be described in detail.

General terms widely used are selected while considering functions in one or more exemplary embodiments for terms used herein, but the terms used herein may differ according to intentions of one of ordinary skill in the art, precedents, or emergence of new technologies. In some cases, an applicant arbitrarily selects a term, and in this case, the meaning of the term will be described in detail herein. Accordingly, the terms shall be defined based on the meanings and details throughout the specification, rather than the simple names of the terms.

When something "includes" a component, another component may be further included unless specified otherwise. The term "unit" used in the present specification refers to a software component, or a hardware component such as FPGA or ASIC, and performs a certain function. However, the "unit" is not limited to software or hardware. The "unit" may be configured in an addressable storage medium and may be configured to be executed by one or more processors. Hence, the "unit" includes elements such as software elements, object-oriented software elements, class elements, and task elements, and processes, functions, attributes, procedures, sub-routines, segments of program codes, drivers, firmware, micro-codes, circuits, data, databases, data structures, tables, arrays, and variables. The functions provided in the elements and the units may be combined into a fewer number of elements and units or may be divided into a larger number of elements and units.

As used herein, the term "and/or" includes any and all combinations of one or more of the associated listed items. Expressions such as "at least one of," when preceding a list of elements, modify the entire list of elements and do not modify the individual elements of the list.

While describing one or more exemplary embodiments, descriptions about drawings that are not related to the one or more exemplary embodiments are omitted.

In the present specification, "image" may refer to multi-dimensional data composed of discrete image elements (e.g., pixels in a two-dimensional image and voxels in a three-dimensional image). For example, an image may include a medical image of an object acquired by an X-ray, computed tomography (CT), magnetic resonance imaging (MRI), ultrasonic waves, or another medical image photographing apparatus.

Furthermore, in the present specification, "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, "user" refers to a medical professional, such as a doctor, a nurse, a medical laboratory technologist, and an engineer who repairs a medical apparatus, but the user is not limited thereto.

Furthermore, in the present specification, "MRI" refers to an image of an object obtained based on the nuclear magnetic resonance principle.

Furthermore, in the present specification, "pulse sequence" refers to continuity of signals repeatedly applied by an MRI apparatus. A pulse sequence may include a time parameter of a radio frequency (RF) pulse, for example, repetition time (TR) or echo time (TE).

Furthermore, in the present specification, "pulse sequence mimetic diagram" shows an order of events that occur in an MRI apparatus. For example, a pulse sequence mimetic diagram may be a diagram showing an RF pulse, a gradient magnetic field, or an MR signal according to time.

An MRI system is an apparatus for acquiring a sectional image of a part of an object by expressing, in a contrast comparison, a strength of a MR signal with respect to a radio frequency (RF) signal generated in a magnetic field having a specific strength. For example, if an RF signal that resonates only a specific atomic nucleus (for example, a hydrogen atomic nucleus) is irradiated for an instant onto the object that is placed in a strong magnetic field and then such irradiation stops, an MR signal is emitted from the specific atomic nucleus, and thus the MRI system may receive the MR signal and acquire an MR image. The MR signal denotes an RF signal emitted from the object. An intensity of the MR signal may be determined according to the density of a predetermined atom (for example, hydrogen) of the object, a relaxation time T1, a relaxation time T2, and blood flow.

MRI systems include different characteristics from those of other imaging apparatuses. Unlike imaging apparatuses such as CT apparatuses that acquire images dependent upon a direction of detection hardware, MRI systems may acquire two-dimensional (2D) images or three-dimensional (3D) volume images that are oriented toward an optional point. MRI systems do not expose objects and examinees to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are important to precisely describe abnormal tissue.

FIG. 1 is a block diagram of a general MRI system. Referring to FIG. 1, the general MRI system may include a gantry 20, a signal transceiver 30, a monitoring unit 40 (e.g., a monitoring device, etc.), a system control unit 50 (e.g., a system controller, etc.), and an operating unit 60 (e.g., an input device, an output device, etc.).

The gantry 20 blocks electromagnetic waves generated by a main magnet 22, a gradient coil 24, and an RF coil 26 from being externally emitted. A magnetostatic field and a gradient magnetic field are formed at a bore in the gantry 20, and an RF signal is irradiated towards an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning a direction of magnetic dipole moments of atomic nuclei of the object 10 in a constant direction. A precise and accurate MR image of the object 10 may be obtained when a magnetic field generated by the main magnet 22 is strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may irradiate an RF signal to a patient and receive an MR signal emitted from the object 10. In detail, the RF coil 26 may transmit an RF signal at a same frequency as precessional motion to the patient towards atomic nuclei in precessional motion, stop transmitting the RF signal, and then receive an MR signal emitted from the object 10.

For example, in order to transit an atomic nucleus from a low energy state to a high energy state, the RF coil 26 may generate and apply an electromagnetic wave signal having an RF corresponding to a type of the atomic nucleus, for example, an RF signal, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus, on which the electromagnetic waves were applied, transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei of the object 10.

The RF coil 26 may be realized as one RF transmitting and receiving coil having both a function of generating electromagnetic waves having a wireless frequency corresponding to a type of an atomic nucleus and a function of receiving electromagnetic waves emitted from an atomic nucleus. Alternatively, the RF coil 26 may be realized as a transmission RF coil having a function of generating electromagnetic waves having a wireless frequency corresponding to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil in any one of various channels, such as 16 channels, 32 channels, 72 channels, and 144 channels.

Hereinafter, it is assumed that the RF coil 26 is an RF multi-coil including N coils respectively corresponding to a plurality of channels, i.e., first through N-th channels. Herein, the RF multi-coil may also be referred to as a multi-channel RF coil.

The gantry 20 may further include a display 29 disposed outside the gantry 20 and a display (not shown) disposed inside the gantry 20. The gantry 20 may provide predetermined information to the user or the object through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 in the gantry 20 and may supply a pulse signal for generating a gradient magnetic field to the gradient coil 24 according to control of a gradient magnetic field controller 54. By controlling the pulse signal supplied from the gradient amplifier 32 to the gradient coil 24, gradient magnetic fields in X-, Y-, and Z-axis directions may be composed.

The RF transmitter 36 and the RF receiver 38 may drive the RF coil 26. The RF transmitter 36 may supply an RF pulse at a Larmor frequency to the RF coil 26, and the RF receiver 38 may receive an MR signal received by the RF coil 26.

The transmission and reception switch 34 may adjust transmitting and receiving directions of the RF signal and the MR signal. For example, the RF signal may be irradiated to the object 10 through the RF coil 26 during a transmission mode, and the MR signal may be received by the object 10 through the RF coil 26 during a reception mode. The transmission and reception switch 34 may be controlled by a control signal from an RF controller 56.

The monitoring unit 40 may monitor or control the gantry 20 or devices mounted on the gantry 20. The monitoring unit 40 may include a system monitoring unit 42 (e.g., a system monitoring device, etc.), an object monitoring unit 44 (e.g., an object monitoring device, etc.), a table controller 46, and a display controller 48.

The system monitoring unit 42 may monitor and control a state of a magnetostatic field, a state of a gradient magnetic field, a state of an RF signal, a state of an RF coil, a state of a table, a state of a device measuring body information of an object, a power supply state, a state of a thermal exchanger, and a state of a compressor.

The object monitoring unit 44 monitors a state of the object 10. In detail, the object monitoring unit 44 may include a camera for observing movement or position of the object 10, a respiration measurer for measuring the respiration of the object 10, an ECG measurer for measuring ECG of the object 10, or a temperature measurer for measuring a temperature of the object 10.

The table controller 46 controls movement of the table 28 where the object 10 is positioned. The table controller 46 may control the movement of the table 28 according to sequence control of a sequence controller 52. For example, during moving imaging of the object 10, the table controller 46 may continuously or discontinuously move the table 28 according to the sequence control of the sequence controller 52, and thus the object 10 may be photographed in a larger field of view FOV than that of the gantry 20.

The display controller 48 controls the display 29 and the display respectively outside and inside the gantry 20. In detail, the display controller 48 may turn on or off the display 29 and the display outside and inside the gantry 20, and may control a screen to be output on the display 29 and the display. When a speaker is located inside or outside the gantry 20, the display controller 48 may turn on or off the speaker or control the speaker to output sound.

The system control unit 50 may include the sequence controller 52 for controlling a sequence of signals formed in the gantry 20, and a gantry controller 58 for controlling the gantry 20 and devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. Here, the pulse sequence includes all information required to control the gradient amplifier 32, the RF transmitter 36, the RF receiver 38, and the transmission and reception switch 34, for example, may include information about strength, an application time, and an application timing of a pulse signal applied to the gradient coil 24.

The operating unit 60 requests the system control unit 50 to transmit pulse sequence information while controlling an overall operation of the general MRI system.

The operating unit 60 may include an image processor 62 for processing an MR signal received from the RF receiver 38, an output unit 64 (e.g., an output device, etc.), and an input unit 66 (e.g., an input device, etc.).

The image processor 62 processes an MR signal received from the RF receiver 38 so as to generate MR image data of the object 10.

The image processor 62 performs any one of various signal processes, such as amplification, frequency transformation, phase detection, low frequency amplification, and filtering, on an MR signal received by the RF receiver 38.

The image processor 62 may arrange digital data in a k space of a memory and rearrange the digital data into image data via 2D or 3D Fourier transformation.

The image processor 62 may perform a composition process or difference calculation process on image data if required. The composition process may include an addition process on a pixel or a maximum intensity projection (MIP) process. The image processor 62 may not only store rearranged image data but also image data on which a composition process or difference calculation process is performed, in a memory (not shown) or an external server.

Signal processes applied to MR signals by the image processor 62 may be performed in parallel. For example, a signal process may be performed on a plurality of MR signals received by a multi-channel RF coil in parallel so as to rearrange the plurality of MR signals as image data.

The output unit 64 may output image data generated or rearranged by the image processor 62 to the user. The output unit 64 may output information required for the user to manipulate the MRI system, such as user interface (UI), user information, or object information. The output unit 64 may include a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a PFD display, a 3-dimensional (3D) display, or a transparent display, or any one of various output devices that are well known to one of ordinary skill in the art.

The user may input object information, parameter information, a scan condition, a pulse sequence, or information about image composition or difference calculation by using the input unit 66. The input unit 66 may include a keyboard, a mouse, a track ball, a voice recognizer, a gesture recognizer, or a touch screen, or may include any one of other various input devices that are well known to one of ordinary skill in the art.

The signal transceiver 30, the monitoring unit 40, the system control unit 50, and the operating unit 60 are separate components in FIG. 1, but it is obvious to one of ordinary skill in the art that functions of the signal transceiver 30, the monitoring unit 40, the system control unit 50, and the operating unit 60 may be performed by another component. For example, the image processor 62 converts an MR signal received by the RF receiver 38 into a digital signal, but such a conversion to a digital signal may be directly performed by the RF receiver 38 or the RF coil 26.

The gantry 20, the RF coil 26, the signal transceiver 30, the monitoring unit 40, the system control unit 50, and the operating unit 60 may be connected to each other via wires or wirelessly, and when they are connected wirelessly, the general MRI system may further include an apparatus (not shown) for synchronizing clocks therebetween. Communication between the gantry 20, the RF coil 26, the signal transceiver 30, the monitoring unit 40, the system control unit 50, and the operating unit 60 may be performed by using a high-speed digital interface, such as low voltage differential signaling (LVDS), asynchronous serial communication, such as universal asynchronous receiver transmitter (UART), a low-delay network protocol, such as an error synchronous serial communication or controller area network (CAN), or optical communication, or any other communication method that is well known to one of ordinary skill in the art.

Figure 2:
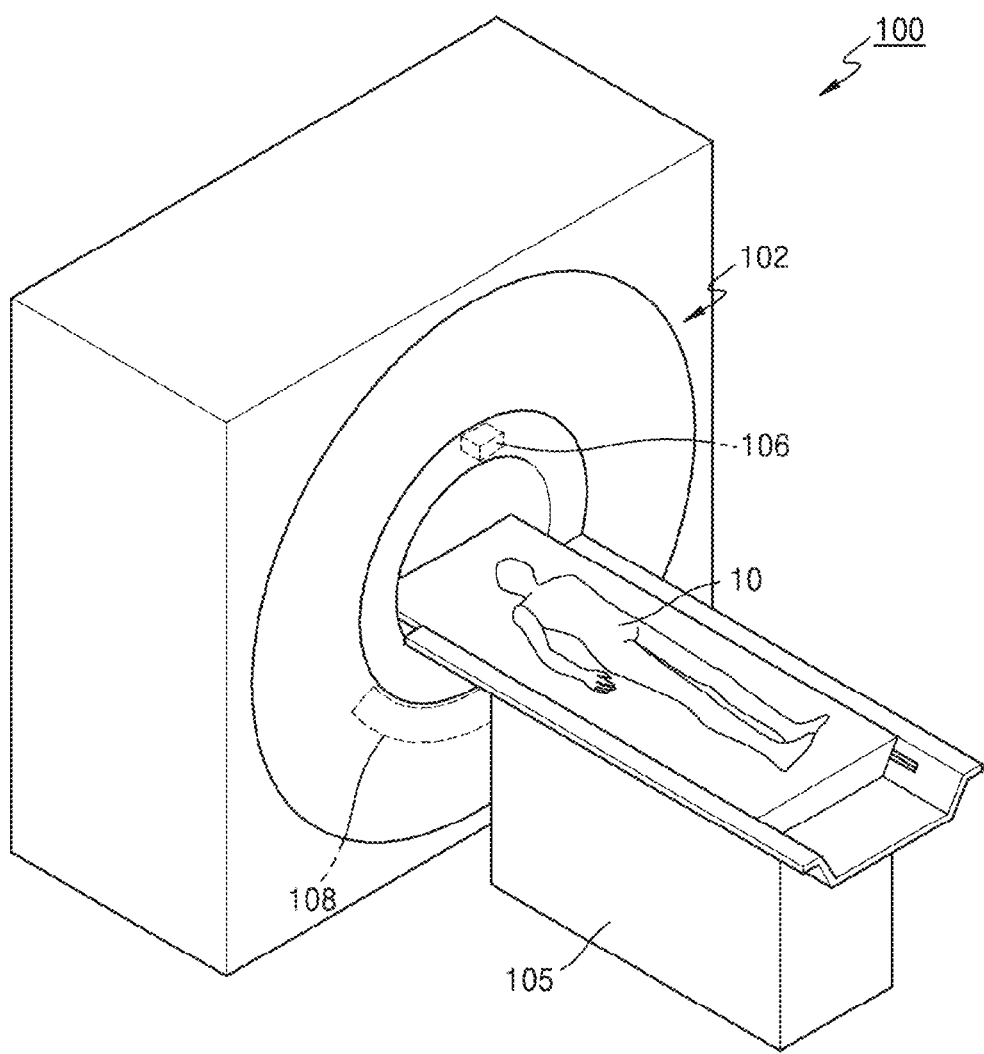
FIG. 2 is a general schematic diagram of a computed tomography (CT) system.

FIG. 2 is a schematic diagram of a general CT system 100. Referring to FIG. 2, the CT system 100 may include a gantry 102, a table 105, an X-ray generating unit 106 (e.g., a ray generator, etc.), and an X-ray detecting unit 108 (e.g., an x-ray detector, etc.).

Since a tomography system, such as a CT system, is capable of providing a cross-sectional image of an object, the CT system may express an inner structure (e.g., an organ such as a kidney, a lung, etc.) of the object without an overlap therebetween, compared to a general X-ray capturing apparatus.

In detail, the tomography system may include any tomography apparatus, such as a CT apparatus, an optical coherence tomography (OCT) apparatus, or a positron emission tomography (PET)-CT apparatus.

Herein, a "tomography image" may be an image that is obtained by a tomography apparatus by scanning an object, and formed by using data projected after irradiating a beam, such as an X-ray, on the object. In detail, a "CT image" may be a composite image of a plurality of X-ray images obtained by capturing an object while rotating around at least one axis with respect to the object.

Hereinafter, the CT system 100 of FIGS. 2 and 3 will be described as an example of the tomography system.

The CT system 100 may obtain a plurality of pieces of image data with a thickness not more than 2 mm for several tens to several hundreds of times per second and then may process the plurality of pieces of image data, so that the CT system 100 may provide a relatively accurate cross-sectional image of the object. According to the related art, only a horizontal cross-sectional image of the object can be obtained, but this issue has been overcome due to various image reconstruction methods. Examples of 3D image reconstruction methods are:

A shade surface display (SSD) method: The SSD method is an initial 3D imaging method that displays only voxels having a predetermined Hounsfield Units (HU) value.

A maximum intensity projection (MIP)/minimum intensity projection (MinIP) method: The MIP/MinIP method is a 3D imaging method that displays only voxels having the greatest or smallest HU value from among voxels that construct an image.

A volume rendering (VR) method: The VR method is an imaging method capable of adjusting a color and transmittance of voxels that construct an image, according to interest areas.

A virtual endoscopy method: This method allows an endoscopy observation in a 3D image that is reconstructed by using the VR method or the SSD method.

A multi-planar reformation (MPR) method: The MPR method is used to reconstruct an image into a different cross-sectional image. A user may reconstruct an image in every desired direction.

An editing method: This method involves editing adjacent voxels so as to allow a user to easily observe an interest area in volume rendering.

A voxel of interest (VOI) method: The VOI method displays only a selected area in volume rendering.

The CT system 100 according to an exemplary embodiment will now be described with reference to FIG. 3. The CT system 100 may include devices having various forms.

The gantry 102 may include the X-ray generating unit 106 and the X-ray detecting unit 108.

An object 10 may be positioned on the table 105.

The table 105 may move in a predetermined direction (e.g., at least one of up, down, right, and left directions) during a CT imaging procedure. The table 105 may tilt or rotate by a predetermined degree in a predetermined direction.

The gantry 102 may also tilt by a predetermined degree in a predetermined direction.

Figure 3:
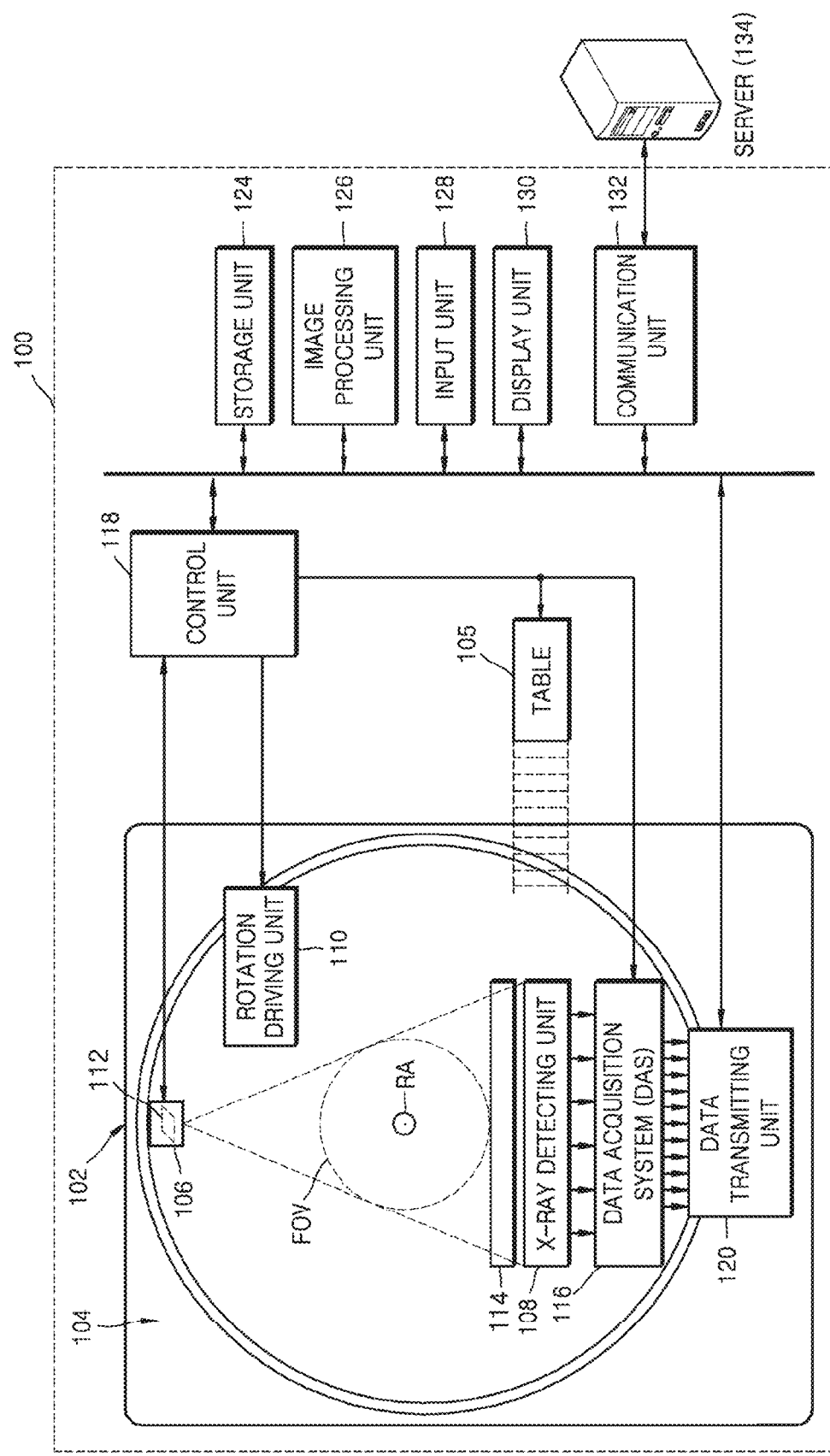
FIG. 3 is a diagram of a structure of the CT system, according to an exemplary embodiment.

FIG. 3 is a diagram of a structure of the CT system 100, according to an exemplary embodiment.

The CT system 100 may include the gantry 102, the table 105, a control unit 118 (e.g., a controller, etc.), a storage unit 124 (e.g., a storage, a memory, etc.), an image processing unit 126 (e.g., an image processor, etc.), a UI unit 128 (e.g., a user interface, etc.), a display unit 130 (e.g. a display, etc.), and a communication unit 132 (e.g., a transceiver, etc.).

As described above, the object 10 may be positioned on the table 105. In the present exemplary embodiment, the table 105 may move in a predetermined direction (e.g., at least one of up, down, right, and left directions), and movement of the table 105 may be controlled by the control unit 118.

The gantry 102 may include a rotating frame 104, the X-ray generating unit 106, the X-ray detecting unit 108, a rotation driving unit 110, a data acquisition system (DAS) 116, and a data transmitting unit 120.

The gantry 102 may include the rotating frame 104 having a loop shape capable of rotating with respect to a predetermined rotation axis RA. The rotating frame 104 may have a disc shape.

The rotating frame 104 may include the X-ray generating unit 106 and the X-ray detecting unit 108 that face each other so as to have predetermined field of views FOVs. The rotating frame 104 may also include an anti-scatter grid 114. The anti-scatter grid 114 may be positioned between the X-ray generating unit 106 and the X-ray detecting unit 108.

In a medical imaging system, X-ray radiation that reaches a detector (or a photosensitive film) includes not only attenuated primary radiation that forms a valuable image but also includes scattered radiation that deteriorates a quality of an image. In order to transmit the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detecting unit 108 by a predetermined rotation speed. The rotating frame 104 may receive the driving signal and power from the rotation driving unit 110 while the rotating frame 104 contacts the rotation driving unit 110 via a slip ring (not shown). The rotating frame 104 may receive the driving signal and power from the rotation driving unit 110 via wireless communication.

The X-ray generating unit 106 may receive a voltage and current from a power distribution unit (PDU) (not shown) via a slip ring (not shown) and then a high voltage generating unit (not shown), and then may generate and emit an X-ray. When the high voltage generating unit applies a predetermined voltage (hereinafter, referred as the tube voltage) to the X-ray generating unit 106, the X-ray generating unit 106 may generate X-rays having a plurality of energy spectrums that correspond to the tube voltage.

The X-ray generated by the X-ray generating unit 106 may have a predetermined form due to a collimator 112 and then may be emitted.

The X-ray detecting unit 108 may be positioned facing the X-ray generating unit 106. The X-ray detecting unit 108 may include a plurality of X-ray detecting devices. Each of the plurality of X-ray detecting devices may establish one channel but one or more exemplary embodiments are not limited thereto.

The X-ray detecting unit 108 may detect the X-ray that is generated by the X-ray generating unit 106 and that is transmitted via the object 10, and may generate an electrical signal corresponding to the intensity of the detected X-ray.

The X-ray detecting unit 108 may include an indirect-type X-ray detector for detecting radiation after converting the radiation into light, and a direct-type X-ray detector for detecting radiation after directly converting the radiation into electric charges. The indirect-type X-ray detector may use a scintillator. The direct-type X-ray detector may use a photon counting detector. The DAS 116 may be connected to the X-ray detecting unit 108. The electrical signal generated by the X-ray detecting unit 108 may be collected via a wired or wireless connection by the DAS 116. The electrical signal generated by the X-ray detecting unit 108 may also be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data.

The digital signal may be provided to the image processing unit 126 via the data transmitting unit 120. The digital signal may be via wires or wirelessly provided to the image processing unit 126.

The control unit 118 may control an operation of each module in the CT system 100. For example, the control unit 118 may control operations of the table 105, the rotation driving unit 110 (e.g., a rotation driver, etc.), the collimator 112, the DAS 116, the storage unit 124, the image processing unit 126, the UI unit 128, the display unit 130, the communication unit 132, or the like.

The image processing unit 126 may receive data (e.g., pure data before a processing operation), which is obtained from the DAS 116, via the data transmitting unit 120 (e.g., a data transmitter, etc.), and may perform pre-processing.

The pre-processing may include a process of correcting sensitivity irregularity between channels, a process of correcting a signal loss due to a rapid decrease of signal strength or due to an X-ray absorbing material such as metal, or the like.

Data output from the image processing unit 126 may be referred as raw data or projection data. The projection data and image-capturing conditions (e.g., the tube voltage, an image-capturing angle, etc.) when obtaining the data may be stored together in the storage unit 124.

The projection data may be a group of data values that correspond to the intensity of the X-ray that passes through the object 10. For convenience of description, it is assumed that a group of a plurality of pieces of projection data that are simultaneously obtained from all channels by a same image-capturing degree is referred as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM), Programmable Read-Only Memory (PROM) magnetic memory, a magnetic disc, and an optical disc.

The image processing unit 126 may reconstruct a cross-sectional image with respect to the object 10 by using the projection data set. The cross-sectional image may be a 3D image. In other words, the image processing unit 126 may reconstruct the 3D image of the object 10 by using a cone beam reconstruction method or the like, based on the projection data set.

The UI unit 128 may receive an external input with respect to an X-ray tomography imaging condition, an image processing condition, or the like. For example, the X-ray tomography imaging condition may include tube voltages, energy value setting with respect to a plurality of X-rays, selection of an image-capturing protocol, selection of an image reconstruction method, setting of a field of view (FOV) area, the number of slices, a slice thickness, parameter setting with respect to image post-processing, or the like. The image processing condition may include the resolution of an image, attenuation coefficient setting with respect to the image, setting of an image combining ratio, or the like.

The UI unit 128 may include a device for receiving a predetermined input from an external source. For example, the UI unit 128 may include a microphone, a keyboard, a mouse, a joystick, a touch pad, a touch pen, a voice recognition device, a gesture recognition device, or the like.

The display unit 130 may display an X-ray tomography image reconstructed by the image processing unit 126.

Exchanges of data, power, or the like between the aforementioned elements may be performed by using at least one of wired communication, wireless communication, and optical communication.

The communication unit 132 may perform communication with an external device, an external medical apparatus, etc. via a server 134 or the like. The communication will now be described with reference to FIG. 4.

Figure 4:
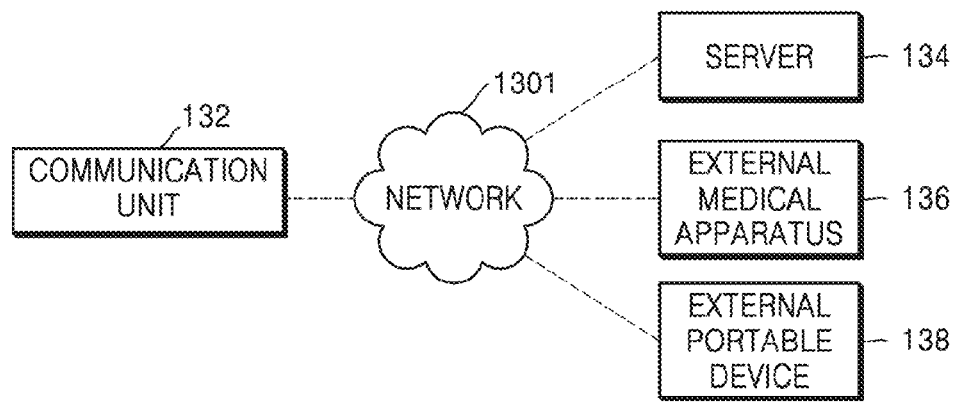
FIG. 4 is a block diagram of a communication unit according to an exemplary embodiment.

FIG. 4 is a block diagram of the communication unit 132 according to an exemplary embodiment.

The communication unit 132 of FIG. 4 may be connected to at least one of the gantry 20, the signal transceiver 30, the monitoring unit 40, the system control unit 50, and the operating unit 60 of FIG. 1. The communication unit 132 may exchange data with a hospital server or other medical apparatuses in a hospital connected via a picture archiving and communication system (PACS), according to a digital imaging and communications in medicine (DICOM) standard.

As shown in FIG. 4, the communication unit 132 may communicate with the server 134, an external medical apparatus 136, or an external portable device 138 by being connected to a network 301 wirelessly or via wires.

In detail, the communication unit 132 may transmit or receive data related to diagnosing an object, via the network 301, and may also transmit or receive a medical image captured by the external medical apparatus 136, such as a CT, an ultrasonic apparatus, or an X-ray apparatus.

The communication unit 132 of FIG. 4 may be included in the CT system 100 of FIG. 3. In this case, the communication unit 132 of FIG. 4 and the communication unit 132 of FIG. 3 are the same.

When the communication unit 132 is included in the CT system 100, the communication unit 132 may operate as follows.

The communication unit 132 may be connected to the network 301 wirelessly or via wires and therefore may perform communication with the server 134, the external medical apparatus 136, or the external portable device 138. The communication unit 132 may exchange data with a hospital server or other medical apparatuses in a hospital connected via PACS. The communication unit 132 may also perform data communication with the external portable device 138 or the like, according to a DICOM standard.

The communication unit 132 may transmit or receive data related to diagnosing the object 10, via the network 301. The communication unit 132 may also transmit or receive a medical image obtained from the external medical apparatus 136 such as an MRI apparatus, an X-ray apparatus, or the like.

Furthermore, the communication unit 132 may receive a diagnosis history or a medical treatment schedule about a patient from the server 134 and may use the diagnosis history or the medical treatment schedule in a clinical diagnosis for the patient. The communication unit 132 may also perform data communication with not only the server 134 or the external medical apparatus 136 in a hospital but also with the external portable device 138 of a user or patient.

The communication unit 132 may also transmit information about a device error, information about a quality control status, or the like to a system manager or a service manager via the network 301, and may receive feedback corresponding to the information.

As described above, medical images obtained by various medical image providing apparatuses express an object in various methods according to types and photographing methods of the medical image providing apparatuses. Characteristics of the medical images differ according to the types and photographing methods of the medical image providing apparatuses. For example, cancer tissue may be easily determined in one medical image and blood vessels may be easily determined in another medical image.

Accordingly, an apparatus for providing a medical image suitable to an intention of a user may be provided by considering a region to be read from the medical image.

Hereinafter, a medical image providing apparatus for providing, when a predetermined region is selected from a medical image, a medical image suitable to an intention of a user in the selected predetermined region, according to one or more exemplary embodiments will be described with reference to FIGS. 5 through 23.

A medical image providing apparatus according to one or more exemplary embodiments may be any image processing apparatus that is capable of displaying, storing, and/or processing a medical image.

In detail, the medical image providing apparatus according to one or more exemplary embodiments may be included in a tomography system, such as the general MRI system or the CT system 100 described above with reference to FIGS. 1 through 4. Alternatively, the medical image providing apparatus may be included in the server 134, the external medical apparatus 136, or the external portable device 138 connected to at least one tomography system, such as the MRI system of FIG. 1 and the CT system 100, via the network 301. Here, the server 134, the external medical apparatus 136, or the external portable device 138 may be an image processing apparatus capable of displaying, storing, or processing at least one of an MRI image and a tomography image. For example, the medical image providing apparatus according to one or more exemplary embodiment may be in a form of the server 134, the external medical apparatus 136, or the external portable device 138, and may be a picture archiving and communication system (PACS) capable of displaying, storing, or processing at least one of an MRI image and a tomography image.

Alternatively, the medical image providing apparatus may be included in any medical imaging system for reconstructing an image by using data obtained by scanning an object, aside from the MRI system or the CT system 100, or may be connected to any medical imaging system.

Figure 5:
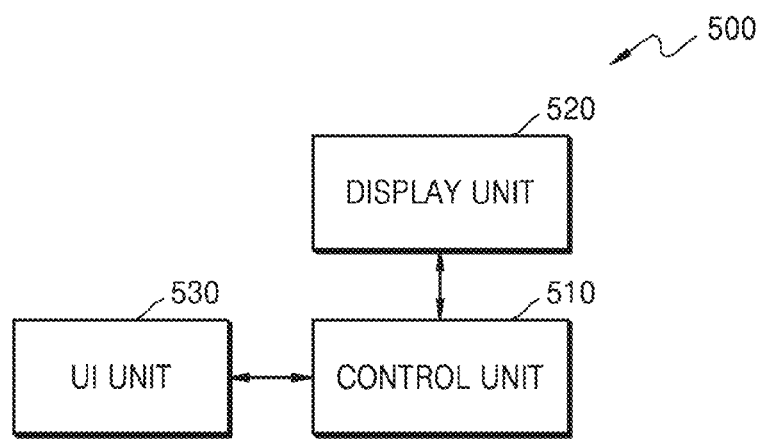
FIG. 5 is a block diagram of a medical image providing apparatus according to an exemplary embodiment.

FIG. 5 is a block diagram of a medical image providing apparatus 500 according to an exemplary embodiment.

Referring to FIG. 5, the medical image providing apparatus 500 includes a control unit 510 (e.g., a controller, etc.), a display unit 520 (e.g., a display), and a UI unit 530 (e.g., a user interface, etc.).

When the medical image providing apparatus 500 is included in the general MRI system of FIG. 1, the medical imaging apparatus 500 may equally correspond to the operating unit 60. In detail, the control unit 510, the display unit 520, and the UI unit 530 may respectively correspond to the image processor 62, the output unit 64, and the input unit 66 of FIG. 1. Accordingly, descriptions of the medical image providing apparatus 500 that are the same as those made with respect to FIG. 1 are not repeated.

Alternatively, when the medical image providing apparatus 500 is included in the CT system 100 of FIG. 3, the control unit 510, the display unit 520, and the UI unit 530 may respectively correspond to the image processing unit 126 or the control unit 118, the display unit 130, and the UI unit 128 of FIG. 3. Accordingly descriptions of the medical image providing apparatus 500 that are the same as those made with respect to FIG. 3 are not repeated.

Alternatively, the medical image providing apparatus 500 may be included in the server 134, the external medical apparatus 136, or the external portable device 138 of FIG. 4.

The display unit 520 displays a first image including an object. Here, the first image is a medical image of the object and may be any medical image captured to diagnose a disease, such as a tomography image like an MRI image or a CT image, an X-ray image, or an ultrasound image. Hereinafter, it is assumed that the first image is an MRI image of a head of a patient.

When a first region in the first image is selected, the UI unit 530 outputs a first list including at least one protocol applied while scanning the object, and receives a selection on a first protocol included in the first list. Here, the first list output by the UI unit 530 is displayed through the display unit 520. In detail, the first list may include at least one CT protocol. Alternatively, the first list may include at least one MRI protocol. Alternatively, the first list may include at least one MRI protocol and at least one CT protocol.

Alternatively, the first list may include a list of images corresponding to a protocol applied while scanning the object.

In detail, the UI unit 530 generates a UI screen including the first list and outputs the UI screen to the display unit 520. Then, the display unit 520 may display the UI screen. A user may see the first list displayed through the display unit 520 and select a predetermined protocol through the UI unit 530.

In detail, the UI unit 530 may receive a predetermined request, a predetermined command, or other data from the user.

For example, the UI unit 530 may include an input device including a mouse, a keyboard, or hard keys for a data input. For example, the user may select the first region in the first image by manipulating at least one of the mouse, the keyboard, or another input device included in the UI unit 530.

Alternatively, the UI unit 530 may be a touch pad. In detail, the UI unit 530 may include a touch pad (not shown) combined to a display panel (not shown) included in the display unit 520, such that the UI screen is output on the display panel. Then, when a predetermined command is input through the UI screen, the touch pad detects the predetermined command to recognize the predetermined command input by the user.

In detail, when the UI unit 530 is a touch pad and the user touches a predetermined point of the UI screen, the UI unit 530 detects the touched point. Then, the UI unit 530 may transmit information about the touched point to the control unit 510. The control unit 510 may recognize a request or command of the user corresponding to a menu option displayed on the touched point, and perform the recognized request or command.

A first example of a method of imaging a medical image includes a method of photographing an object by irradiating a beam, such as an X-ray, on the object, like an imaging method of an X-ray image. Here, the object is imaged regardless of a photographing technique or a scan mode. Here, the method may image the object without having to perform a separate restoring or calculating operation to reconstruct an image.

A second example includes a method of imaging an object by variously applying photographing techniques or scan modes while photographing the object, such as an MRI or CT image.

In the second example, images having different characteristics may be obtained even when the same region of a body is photographed, by using various variables considerable while scanning the object. In other words, an image suitable to a purpose may be obtained by changing a scan mode according to uses or purposes. Here, the method may perform a separate restoring or calculating operation to reconstruct a target image.

Here, a technique applied while capturing a medical image by scanning an object is referred to as a 'scan protocol' or a 'protocol', and will now be referred to as a 'protocol' herein. Image data may be obtained by applying a protocol may be used to generate a medical image that is a reconstructed image via image reconstruction. Alternatively, calculated or post-processed data or image may be generated by using image data obtained by applying a protocol.

In an MRI system, an object is scanned by applying various protocols, and an image of the object is reconstructed by using an MR signal obtained accordingly. Hereinafter, data obtained by scanning the object, for example, an MR signal or K-space data, will be referred to as image data, and an image of the object, which is reconstructed by using image data, will be referred to as a reconstructed image.

In a CT system, an object may be scanned by applying different protocols based on whether a contrast medium is administered. Also, in the CT system, obtained image data may be sinogram or projection data, and a reconstructed image may be generated by using the obtained image data.

A protocol will be described in detail later with reference to FIGS. 7A and 7B.

The control unit 510 may control a second image reconstructed by using image data obtained by applying the first protocol to be overlaid and displayed on the first region of the first image.

Alternatively, a plurality of partial regions may be selected from the first image. In this case, a predetermined protocol may be individually selected for the partial regions. Then, the control unit 510 may overlay and display reconstructed images corresponding to the individual protocols selected for the partial regions, on the first region of the first image.

The control unit 510, the display unit 520, and the UI unit 530 may be connected to each other wirelessly or via wires, and may exchange data therebetween.

Figure 6:
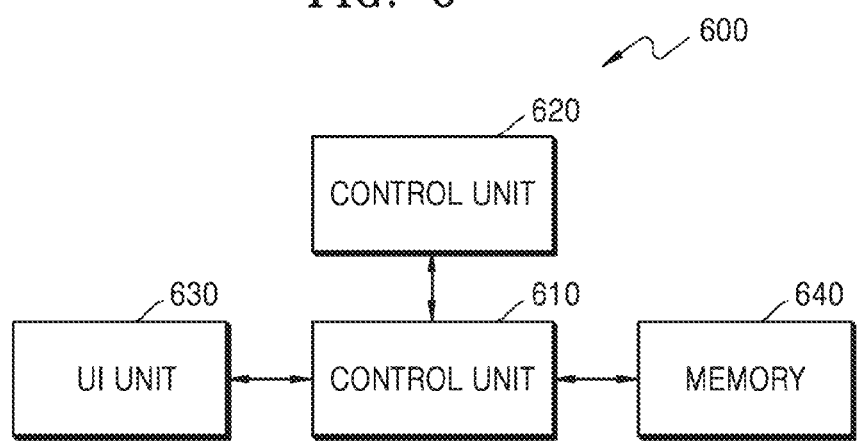
FIG. 6 is a block diagram of a medical image providing apparatus according to another exemplary embodiment.

FIG. 6 is a block diagram of a medical image providing apparatus 600 according to another exemplary embodiment. The medical image providing apparatus 600 of FIG. 6 further includes a memory 640, compared to the medical image providing apparatus 500.

In detail, a control unit 610, a display unit 620, and a UI unit 630 of the medical image providing apparatus 600 respectively correspond to the control unit 510, the display unit 520, and the UI unit 530 of the medical image providing apparatus 500. Accordingly, descriptions about the medical image providing apparatus 600 that are the same as those of the medical image providing apparatus 500 of FIG. 5 are not repeated.

The memory 640 may store various types of data related to a medical image. In detail, the memory 640 may store at least one piece of image data obtained by applying at least one protocol.

The memory 640 may also store at least one reconstructed image that is reconstructed by using at least one piece of image data obtained by applying at least one protocol.

The medical image providing apparatuses 500 and 600 will now be described in detail with reference to FIGS. 7A through 23.

Figure 7A:
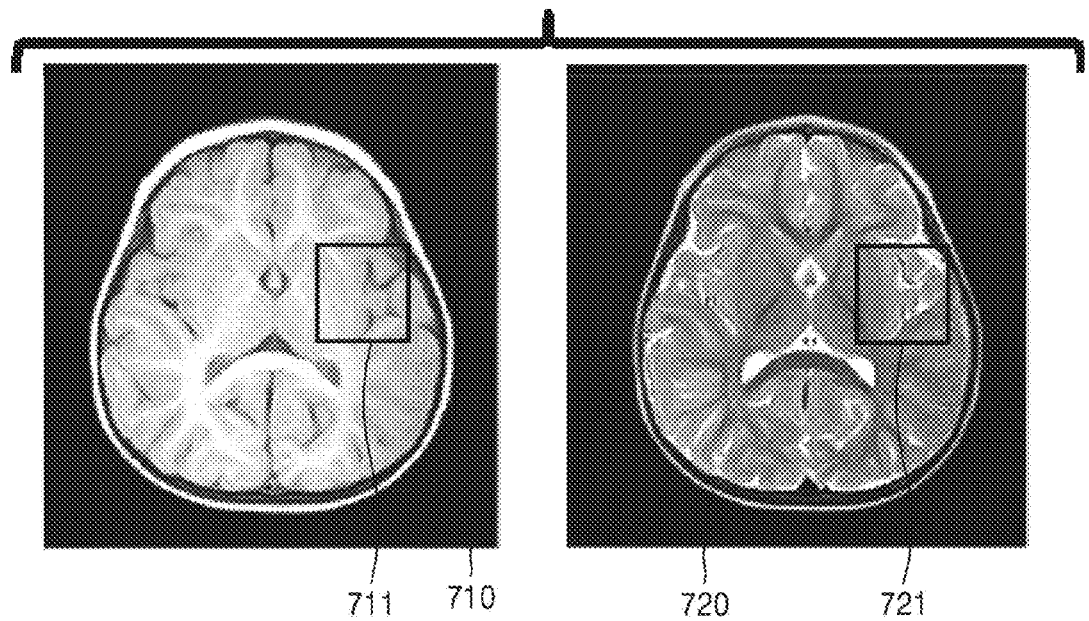
FIG. 7A illustrates a plurality of magnetic resonance (MR) images reconstructed by scanning an object according to different protocols.

FIG. 7A illustrates a plurality of MR images reconstructed by scanning an object according to different protocols.

An MRI protocol is a protocol related to a pulse sequence of an MR signal. In detail, a protocol for obtaining an MRI reconstructed image is related to a pulse sequence of a signal applied to an object while scanning the object, or a signal generated correspondingly to an applied pulse sequence, and may be classified according to a predetermined period of a pulse sequence.

For example, an MR signal is generated correspondingly to an RF signal applied to an object through the RF coil 26 included in the MRI system, while scanning the object.

In a pulse sequence of an RF signal, a time consumed by a nuclear spin to return back up to 63% of original magnetization is referred to as a T1 relaxation time, and a time consumed by the nuclear spin to discharge down to 37% of the original magnetization is referred to as a T2 relaxation time. The MRI protocol is related to at least one of the T1 relaxation time and the T2 relaxation time. Hereinafter, the T1 relaxation time is referred to as a 'T1 period' and the T2 relaxation time is referred to as a 'T2 period'.

In detail, a protocol for obtaining an MRI reconstructed image may be largely classified into a T1 period-related protocol, a T2 period-related protocol, and a T1 and T2 period-related protocol. In detail, examples of the protocol include a protocol for obtaining a T1-weighted image (hereinafter, referred to as a T1W protocol), a protocol for obtaining a T2-weighted image (hereinafter, referred to as a T2W protocol), a protocol for obtaining a T1 flair image (hereinafter, referred to as a T1W flair protocol), a protocol for obtaining a T2 flair image (hereinafter, referred to as a T2W flair protocol), a protocol for obtaining a diffusion image (hereinafter, referred to as a diffusion protocol), and a protocol for obtaining a perfusion image (hereinafter, referred to as a perfusion protocol).

Examples of information that is post-processed or calculated by using image data obtained by applying a protocol include a cerebral blood volume (CBV) map, a cerebral blood flow (CBF) map, histogram equalization information, an apparent diffusion coefficient (ADC) map, a trace map, a perfusion map, an fMRI map showing brain functions, an MRI property map, such as a T1 map or a T2 map, a fractional anisotropy map, and a diffusion tractography map.

In addition, there are various protocols used to generate an MRI image, and the protocols may slightly vary according to product specifications of the MRI system. Information may be obtained by using image data obtained by applying the various protocols may vary.

An image reconstructed by using image data obtained by applying a T1W protocol is referred to as a T1-weighted image, and an image reconstructed by using image data obtained by applying a T2W protocol is referred to as a T2-weighted image. An image reconstructed by using image data obtained by applying a T1W flair protocol is referred to as a T1W flair image, and an image reconstructed by using image data obtained by applying a T2W flair protocol is referred to as a T2W flair image. An image reconstructed by using image data obtained by applying a diffusion protocol is referred to as a diffusion image, and an image reconstructed by using image data obtained by applying a perfusion protocol is referred to as a perfusion image. In addition, there are other various types of MRI images. Also, at least one of different images may be generated by using image data obtained by applying the same protocol. For example, a CBV map, a CBF map, and a mean transit time (MTT) map may be obtained by applying a perfusion protocol. In other words, perfusion images obtained by applying a perfusion protocol may include a CBV map, a CBF map, and an MTT map.

MRI images may be classified into anatomical images and functional images.

An anatomical image is an image reconstructed by directly sampling an MR signal received from an object, when an MR image is captured by setting and applying an acquisition parameter as a predetermined value in the general MRI system of FIG. 1. In other words, the anatomical image may be obtained without having to perform a separate post-process or calculation, by using data obtained by driving the MRI system.

Here, acquisition parameters are values of scan conditions applied while performing MRI photographing, and include a repetition time TR, an echo time TE, and a flip angle FA. The acquisition parameters may further include a band width, a slice gap, a slice thickness, and the number of excitations NEX, and other various acquisition parameters according to models or production specifications of the MRI system.

Here, an echo time TE is a time from when a 90° RF signal is applied to an object to when an echo signal is received, and affects a contrast of a T2-weighted image. A repetition time TR is a time from when a 90° RF signal is applied to obtain a signal about a selected cross section to when a 90° RF signal is applied to obtain a next signal, and affects a contrast of a T1-weighted image.

A flip angle FA is a value indicating an angle of longitudinal magnetization generated by using an RF signal. Here, a T1 weighted effect is obtained when the flip angle FA is large, and a T2 weighted effect is obtained when the flip angle FA is small.

A slice gap indicates a gap between two slices, and is set to a predetermined value to obtain a 2-dimensional (2D) image and is not set to obtain a 3D image. A slice thickness denotes a width of a voxel in which a signal is generated on a cross section of an object to be examined. When the slice thickness is low, space resolution is high but a signal to noise ratio (SNR) is low.

The number of excitations NEX is a value indicating the number of times an image signal emitted from each voxel of a tissue is excited to prepare one image. When the number of excitations NEX is high, an SNR is high.

For example, when a repetition time TR and an echo time TE are set to be short, a T1-weighted image may be obtained by increasing a contrast between tissues having a fast T1 relaxation time and tissues having a slow T1 relaxation time, and reducing a T2 time difference according to traverse relaxation.

Alternatively, when a repetition time TR and an echo time TE are set to be long, a T2-weighted image may be obtained by increasing a difference of traverse relaxation as much as possible to increase a contrast between tissues, and reducing a longitudinal relaxation difference between tissues.

As described above, an anatomical image is an image obtained as the MRI system to which acquisition parameters set to predetermined values are applied directly scans an object. In detail, examples of the anatomical image include a T1-weighted image, a T2-weighted image, a T1 flair image, a T2 flair image, and a diffusion image.

A functional image is an image generated by using information extracted from the anatomical image described above, or information calculated by using image data obtained by applying a predetermined protocol. In detail, the functional image is an image generated by using information that is post-processed by using a data set obtained to restore an anatomical image, or calculated by using a data set obtained by applying a predetermined protocol. In other words, the functional image cannot be directly reconstructed by using image data obtained by applying a predetermined protocol, but is obtained via a post-process or calculation.

In detail, examples of the functional image include an ADC map indicating tissue viability about whether tissues are alive or dead, CBF and CBV maps indicating blood-related information, an fMRI map indicating brain functions, T1 and T2 maps indicating properties of an MRI sequence, a fractional anisotropy map, and a diffusion tractography image.

Examples of a functional image generated by using information calculated using image data obtained by applying a diffusion protocol include an ADC map, a trace map, and a diffusion tractography image. Examples of a functional image generated by using information calculated using image data obtained by applying a perfusion protocol include a mean transit time (MTT) map, a CBV map, and a CBF map. A T1 map may be obtained by using image data obtained by applying a T1W protocol, and a T2 map may be obtained by using image data obtained by applying a T2W protocol. Other various types of functional images may be obtained according to protocols.

In a CT system, a protocol for generating a CT image may be largely classified into a case when CT photographing is performed by using a contrast medium and a case when a contrast medium is not used. In detail, an example of a protocol for scanning a CT image by using a contrast medium includes a perfusion protocol. An example of a protocol for scanning a CT image without using a contrast medium includes a digital subtraction angiography (DSA) image protocol (hereinafter, referred to as a DSA protocol). Other various protocols may be used to capture a CT image, and may differ according to product specifications of a CT system.

FIG. 7A illustrates images that are scanned and reconstructed by applying MRI protocols. In detail, FIG. 7A illustrates a T1-weighted image 710 and a T2-weighted image 720 obtained by respectively applying the T1W protocol and the T2W protocol from among MRI images.

Referring to FIG. 7A, the T1-weighted image 710 is an MRI image having an excellent contrast between soft tissues and satisfactorily showing an anatomical structure. In the T1-weighted image 710, fat is shown in white due to high signal strength. A fast blood flow, a structure filled with fluid, and cerebrospinal fluid are shown in black due to low signal strength.

Referring to FIG. 7A, the T2-weighted image 720 is an MRI image satisfactorily showing a pathological lesion, and may be used to diagnose cancer. In the T2-weighted image 720, cerebrospinal fluid is shown in white, and fat and muscles are shown relatively dark due to low or medium signal strength.

Figure 7B:
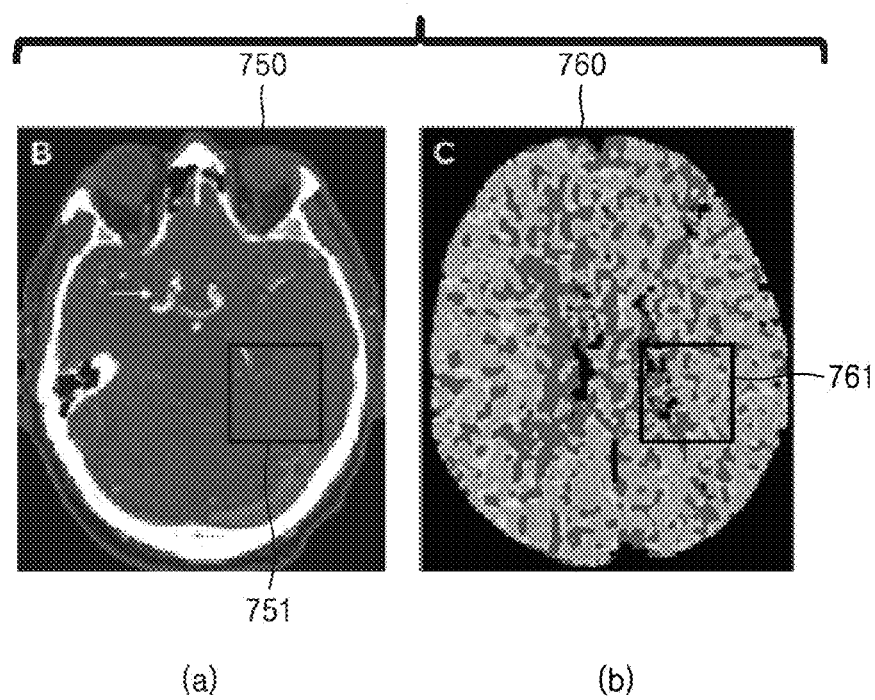
FIG. 7B illustrates a plurality of tomography images reconstructed by scanning an object according to different protocols.

FIG. 7B illustrates images that are scanned and reconstructed by applying CT protocols. In detail, when an object is a brain, FIG. 7B illustrates a CT angiography image 750 obtained according to a DSA protocol that does not use a contrast medium, and a CT perfusion image 760 captured by using a contrast medium.

FIG. 7B (a) shows the CT angiography image 750 obtained by applying the DSA protocol that does not use a contrast medium. The CT angiography image 750 is a CT image that clearly shows blood vessels.

FIG. 7B (b) shows the CT perfusion image 760 obtained by applying a perfusion protocol that performs scanning by using a contrast medium.

As described above with reference to FIGS. 7A and 7B, images reconstructed by using image data obtained by applying different protocols differently express an object and have different image characteristics.

The UI screens output from the medical image providing apparatuses 500 and 600, according to one or more exemplary embodiments, will now be described in detail with reference to FIGS. 8A through 37. Here, FIGS. 8A through 37 will be described with reference to the medical image providing apparatus 600.

Figure 8A:
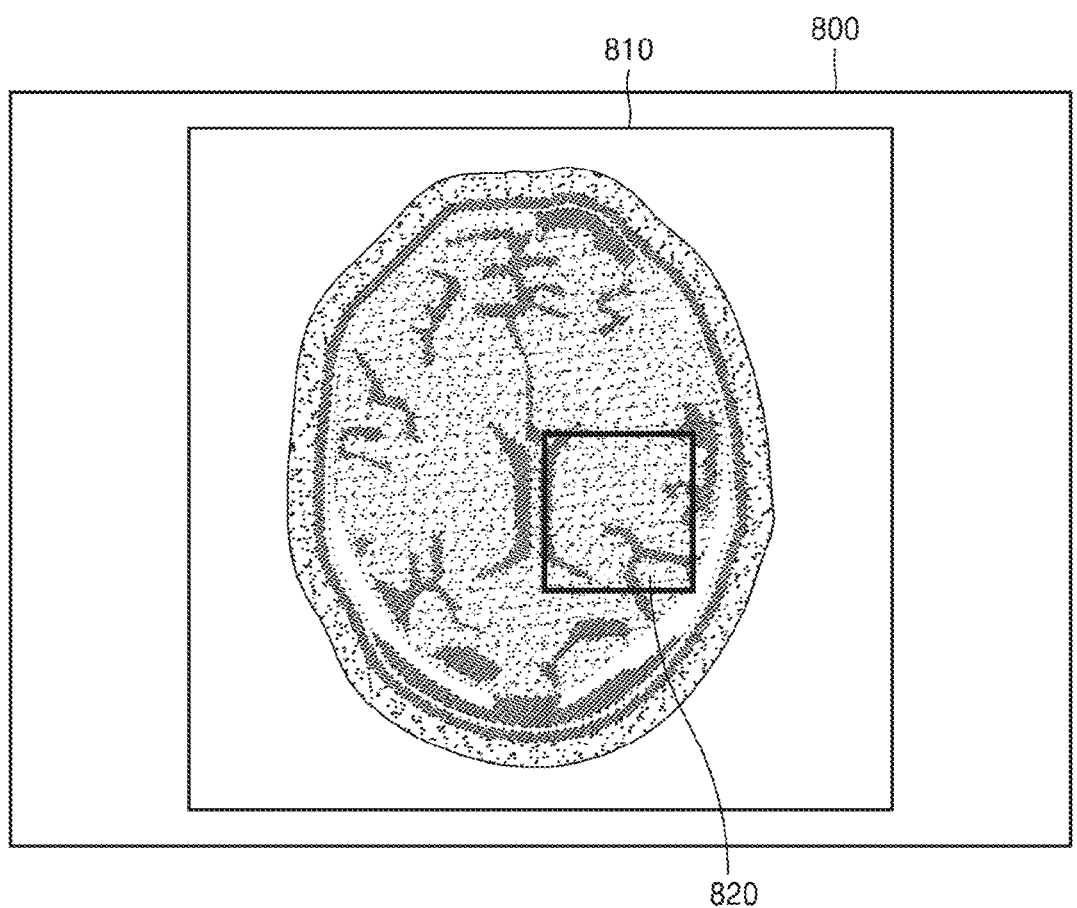
FIG. 8A is an image for describing operations of a medical image providing apparatus, according to an exemplary embodiment.

FIG. 8A is a diagram for describing operations of the medical image providing apparatus 600, according to an exemplary embodiment.

FIG. 8A illustrates an example of an image displayed on the display unit 620. In detail, the display unit 620 displays a screen 800 including a first image 810 through a display panel included in the display unit 620. The first image 810 included in the screen 800 displayed by the display unit 620 may be any medical image of an object. In FIG. 8A, a brain MRI image is shown as the first image 810. In detail, the first image 810 is an anatomical image of the brain MRI image to represent anatomical structure of a brain.

When a first region 820 in the first image 810 is selected, the UI unit 630 outputs a first list including at least one protocol applied while scanning an object. In detail, the first list may include at least one item corresponding to at least one of the plurality of MRI protocols and the plurality of CT protocols described above.

In FIG. 8A, one region, i.e., the first region 820, is selected, but alternatively, a plurality of partial regions may be selected from the first image 810.

In detail, the UI unit 630 may receive a selection on a region of interest (ROI) in the first image 810 from a user. For example, when the user selects a predetermined region by using a mouse, the UI unit 630 may set the selected predetermined region as an ROI. Here, the ROI is the first region 820.

One ROI is set in FIG. 8A, but alternatively, a plurality of ROIs may be set.

For example, when the user selects a predetermined point on the first image 810 while setting an ROI, an ROI having a predetermined size around the predetermined point may be automatically set. In detail, when the UI unit 630 includes a mouse and the user clicks a predetermined point on the first image 810, a rectangular ROI having a predetermined size around the predetermined point may be set. Here, a size of an ROI may be pre-set by the user or may be set by the control unit 610.

Alternatively, when the UI unit 630 includes a touch pad and the user touches a predetermined point on the first image 810 a predetermined number of times, a rectangular ROI having a predetermined size around the touched predetermined point may be set.

Alternatively, while setting an ROI, the user may adjust a size of an ROI through the UI unit 630 to set the first region 820. For example, when the UI unit 630 includes a mouse and the user clicks a predetermined point on the first image 810, a quadrangle for setting the first image 810 may be displayed and the user may adjust a size of the displayed quadrangle to adjust the size of the first region 820.

Furthermore, the user may adjust at least one of the size, location, and shape of the first region 820 by using any one of various input devices in the UI unit 630.

The first region 820 may be automatically selected by the control unit 610, without having to be selected by the user. In other words, the control unit 610 may automatically select or extract the first region 820 from the first image 810.

In detail, the control unit 610 may automatically extract a diagnosis target region from the first image 810 and select the extracted diagnosis target region as the first region 820. Here, the diagnosis target region is an object for diagnosing a disease of a patient, for example, a body organ, a body tissue, or a certain region of a body.

For example, when the user wants to diagnose an abnormality of a certain brain blood vessel or a certain brain region, the user may input the diagnosis target region through the UI unit 630. Then, the control unit 610 may automatically extract the input diagnosis target region.

The control unit 610 may automatically perform an organ segmentation on a medical image displayed on the display unit 530. Then, a segmented region may be selected as the first region 820. For example, when a chest MRI image is captured and the user wants to determine whether a tumor is generated in a certain organ, the control unit 610 may segment organs in the chest MRI image.

Here, when a plurality of organs are segmented, the UI unit 630 generates a UI screen for selecting at least one of the plurality of segmented organs, and the display unit 620 displays the UI screen. Then, the user selects at least one organ through the displayed UI screen, and a region corresponding to the selected organ may be set as the first region 820.

Alternatively, when a plurality of organs are segmented, the control unit 610 may set a plurality of partial regions including the plurality of organs as the first regions 820.

Alternatively, the control unit 610 may automatically extract a disease suspected region from the first image 810 and select the disease suspected region as the first region 820. In detail, the control unit 610 examines whether an abnormal tissue, an abnormal organ structure, or a lesion is generated in the first image 810. Then, the control unit 610 may extract a region including the lesion, the abnormal tissue, or the abnormal organ structure as a disease suspected region, and select the disease suspected region as the first region 820.

After the first region 820 is selected, the size of the first region 820 may be expanded or reduced by using an edit menu (not shown) for the first region 820. In addition, even after the first region 820 is selected, the location of the first region 820 may be changed and reset.

For example, a shape of a cell may be deformed as a previous step of a tumor. In this case, a deformed cell tissue may be determined as a disease suspected region, and the control unit 610 extracts the deformed cell tissue as the disease suspected region. Then, the control unit 610 may select a region including the extracted disease suspected region as the first region 820.

When the memory 640 stores at least one piece of image data obtained by applying at least one protocol and a predetermined protocol is selected from the first list, the control unit 610 reads predetermined image data corresponding to the predetermined protocol stored in the memory 640. Then, a second image may be reconstructed in real-time by using the read predetermined image data.

When the memory 640 stores a reconstructed image corresponding to a protocol and a predetermined protocol is selected from the first list, the control unit 610 may generate a second image corresponding to the first region 820 in real-time by using the stored reconstructed image.

When a predetermined protocol is selected, the control unit 610 may obtain image data in real-time by operating a medical image system, such as an MRI system, for capturing a medical image by applying the predetermined protocol. Then, the control unit 610 may reconstruct a second image by using the obtained image data.

Figure 8B:
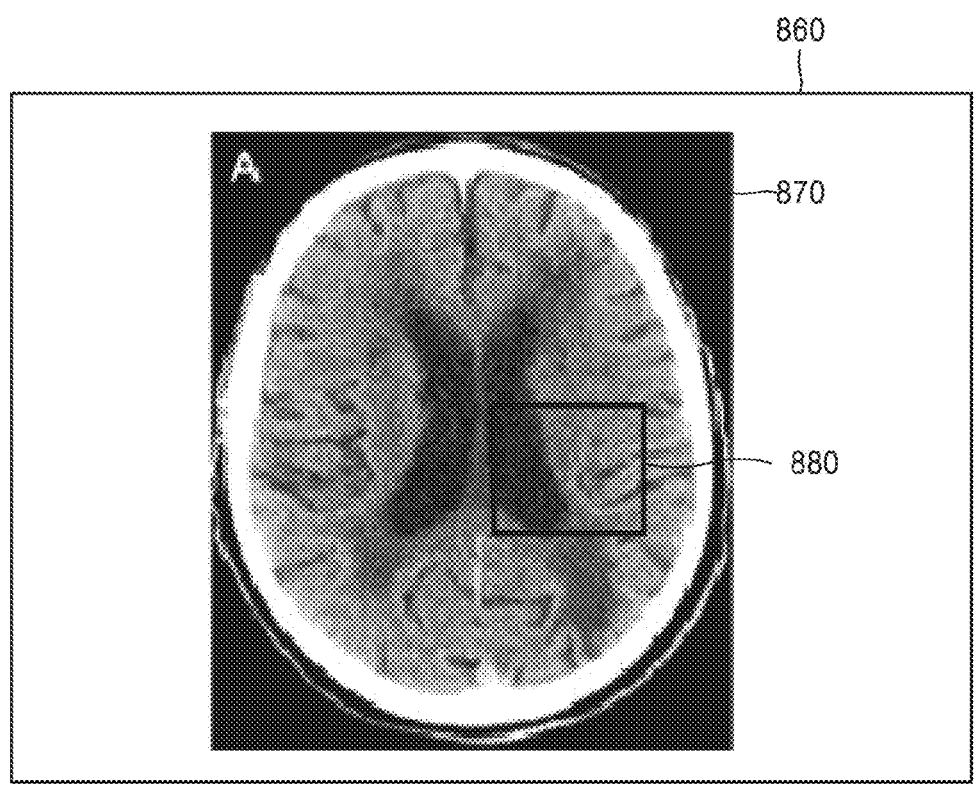
FIG. 8B is an image for describing operations of a medical image providing apparatus, according to an exemplary embodiment.

FIG. 8B is a diagram for describing operations of a medical image providing apparatus, according to an exemplary embodiment. In FIG. 8A, the first image 810 included in the screen 800 displayed by the display unit 620 is an MRI image, but in FIG. 8B, a first image 870 included in a screen 860 displayed by the display unit 620 is a CT image. In detail, in FIG. 8B, the first image 870 is an anatomical image of a brain CT image to represent anatomical structure of a brain.

Figure 9A:
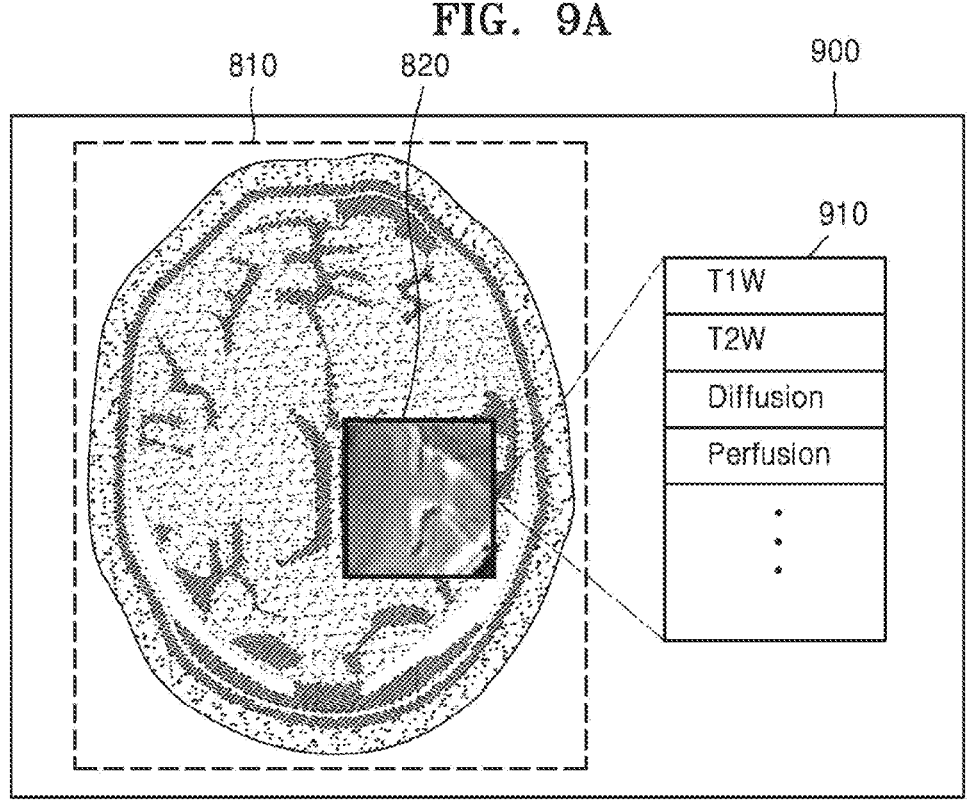
FIGS. 9A and 9B show diagrams for describing operations of a medical image providing apparatus, according to another exemplary embodiment.
Figure 9B:
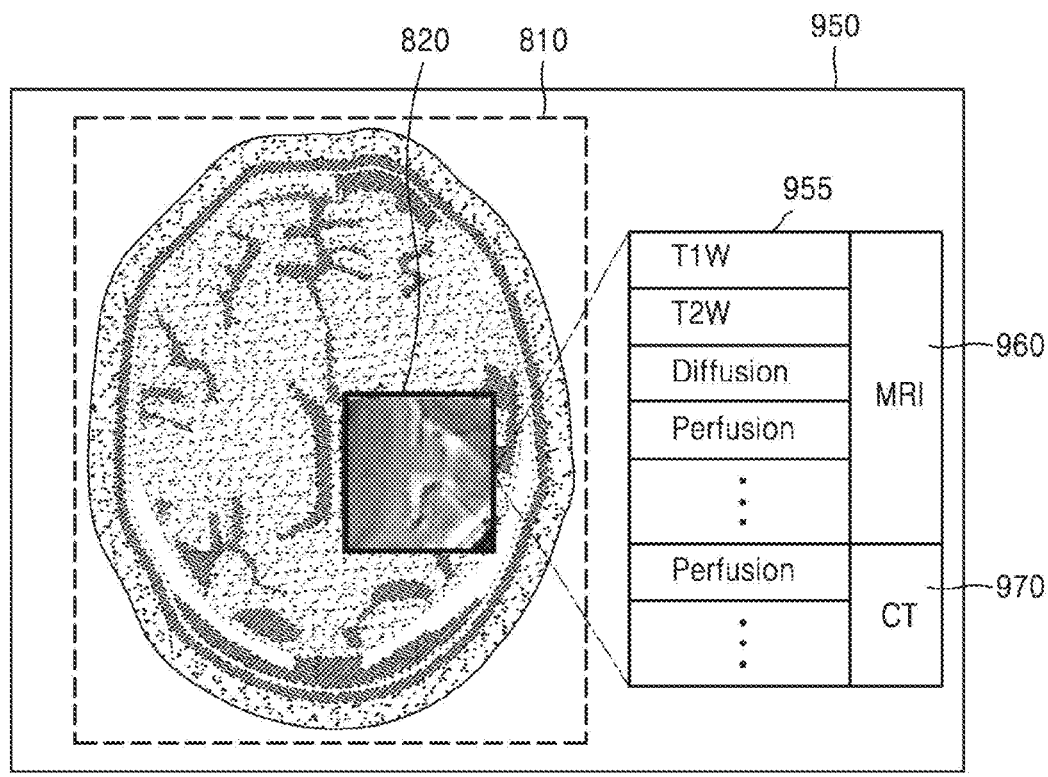

FIGS. 9A and 9B show diagrams for describing operations of the medical image providing apparatus 600, according to another exemplary embodiment. In detail, FIG. 9A illustrates an example of a first list 910 output on the display unit 620. FIG. 9B illustrates another example of a first list 955 output on the display unit 620.

Referring to FIG. 9A, a screen 900 displayed on the display unit 620 includes the first image 810 and the first list 910.

Referring to FIG. 9A, when the first region 820 is selected, the medical image providing apparatus 600 may automatically output the first list 910 including at least one protocol.

Here, the first list 910 may include at least one protocol described above. In detail, the first list 910 includes at least one protocol applied while scanning an object. Here, the at least one protocol is used to obtain images of the same body region having different characteristics, and as described above, may include at least one of MRI protocols and CT protocols.

The first list 910 may also include image lists according to protocols applied while scanning an object. In FIG. 9A, a 'T1W' item in the first list 910 may denote a 'T1W protocol' or a 'T1-weighted image' scanned and reconstructed by applying the 'T1W protocol'. Hereinafter, it is assumed that items in a first list denote protocols.

When the user manipulates the UI unit 630 to input a predetermined command after the first region 820 is selected, the control unit 610 may output the first list 910. For example, when the UI unit 630 includes a mouse and the user right-clicks the mouse after the first region 820 is selected, the first list 910 may be output. Alternatively, when the user double-clicks the mouse after the first region 820 is selected, the first list 910 may be output. As another example, when the UI unit 630 includes a touch pad and the user touches the first region 820 on the screen 900 after the first region 820 is selected, the first list 910 may be output.

Alternatively, the control unit 610 may output the first list 910 when the user manipulates the UI unit 630 in any one of various methods.

Referring to FIG. 9A, the first list 910 includes a T1W protocol, a T2W protocol, a diffusion protocol, perfusion protocol, etc., which are MRI protocols.

The first list 910 of FIG. 9A may include other various protocols.

The user may select a predetermined protocol in the first list 910. For example, the user may select the T1W protocol through the UI unit 630.

When the T1W protocol is selected, the control unit 610 may overlay and display on the first region 820, a T1-weighted image that is a second image reconstructed by using image data obtained by applying the T1W protocol. In other words, the display unit 620 may display the screen 900 of FIG. 9A according to a control of the control unit 610.

Here, the second image displayed on the first region 820 may be a partial image corresponding to a predetermined region of the object included in the first region 820 with respect to an image obtained by applying a selected protocol.

For example, when the T1W protocol is selected, the control unit 610 overlays and displays on the first region 820 of the first image 810, a region 711 of FIG. 7 of the T1-weighted image 710, which equally corresponds to the first region 820.

In detail, when the user wants to view an anatomical structure of the first region 820 in detail, the user may select a T1W protocol for generating a T1-weighted image that satisfactorily shows an anatomical structure, through the UI unit 630. Then, the control unit 610 overlays and displays on the first region 820, the T1-weighted image reconstructed by using image data obtained by the T1W protocol.

Alternatively, when it is suspected that a tumor is generated in the first region 820 by reading the first image 810, the user may select a T2W protocol for generating a T2-weighted image that satisfactorily shows a tumor, through the UI unit 630. Then, the control unit 510 overlays and displays on the first region 820, a T2-weighted image reconstructed by using image data obtained by the T2W protocol.

Each item of the first list 910 may include a reconstructed image corresponding to a protocol. Here, a reconstructed image included in each item of the first list 910 may be a whole image of an object or a partial image corresponding to the first region 820.

Referring to FIG. 9B, a screen 950 displayed on the display unit 620 may include the first image 810 and the first list 955. Referring to FIG. 9B, when the first region 820 is selected, the medical image providing apparatus 600 may output the first list 955 including at least one protocol.

Here, the first list 955 may include at least one protocol described above. Here, a plurality of protocols are used to obtain images of the same body region having different characteristics, and as described above, may include at least one of MRI protocols and CT protocols.

Referring to FIG. 9B, the first list 955 includes a T1W protocol, a T2W protocol, a diffusion protocol, and a perfusion protocol, which are MRI protocols 960, and a perfusion protocol that is a CT protocol 970. Also, the first list 955 may separately include the MRI protocol 960 and the CT protocol 970, as shown in FIG. 9B.

As described above, reconstructed images corresponding to protocols have different characteristics according to protocols. Accordingly, a protocol may be selected by considering a detailed region of an object to be diagnosed, and a disease to be diagnosed in the detailed region.

As such, the medical image providing apparatuses 500 and 600 according to the exemplary embodiments output a list of protocols, and overlay and display an image of a predetermined protocol in an ROI to output a medical image suitable to an intention of the user.

Figure 10A:
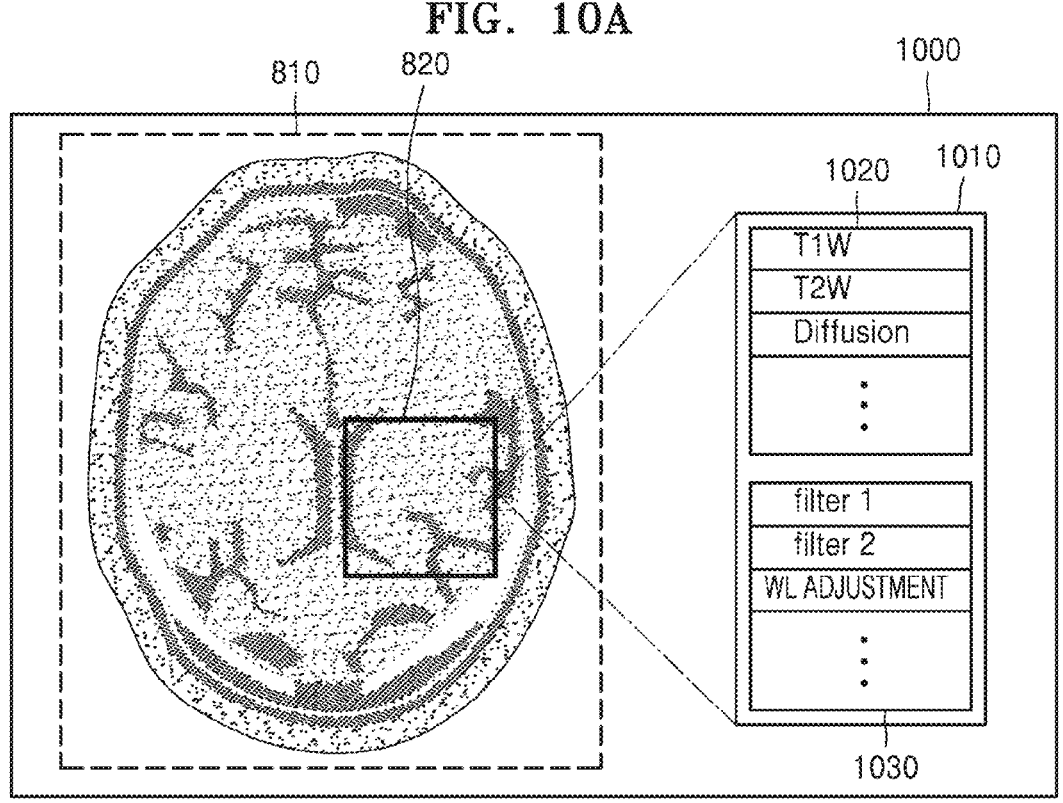
FIGS. 10A and 10B show diagrams for describing operations of a medical image providing apparatus, according to another exemplary embodiment.
Figure 10B:
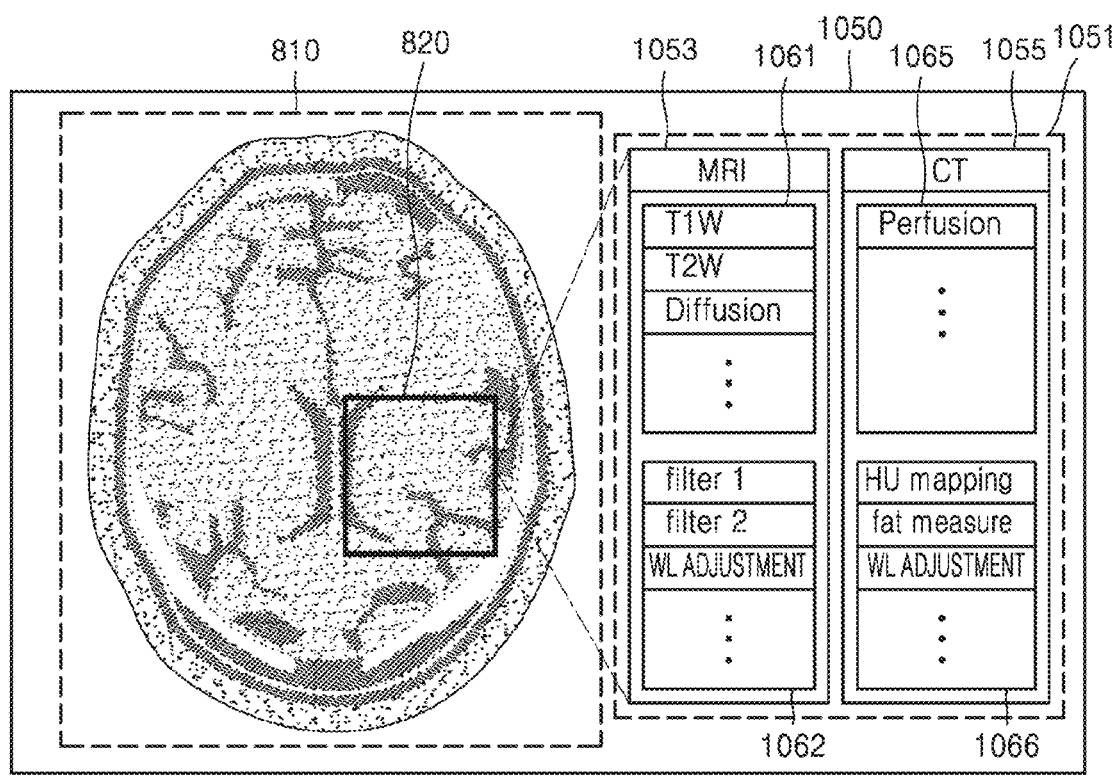

FIGS. 10A and 10B show diagrams for describing operations of the medical image providing apparatus 600, according to another exemplary embodiment.

Referring to FIG. 10A, a screen 1000 displayed on the display unit 620 may include the first image 810 and a first list 1010. In detail, when the first region 820 is selected, the medical image providing apparatus 600 may output the first list 1010.

Referring to FIG. 10A, the first list 1010 may include at least one protocol described above, and at least one manipulation menu item. In detail, the first list 1010 may include a first sub-list 1020 including at least one protocol, and a second sub-list 1030 including at least one manipulation menu item. Here, a manipulation menu item is a menu option for manipulating characteristics of an image included in the first region 820 of the first image 810. Examples of the manipulation menu item include a menu option for filtering an image of the first region 820 by using a predetermined filter, a menu option for adjusting a window level (WL) of the image of the first region 820, and a menu option for adjusting a contrast of the image of the first region 820.

In FIG. 10A, the second sub-list 1030 including the at least one manipulation menu item includes a first filter (filter 1), a second filter (filter 2), and a WL adjusting item (WL adjustment).

For example, when the user selects the filter 1 from the first list 1010, the control unit 510 may filter an image of the first region 820 by using the filter 1, and overlay and display the filtered image on the first region 820.

Alternatively, when the user selects the WL adjustment from the first list 1010, the control unit 510 may adjust a WL of the image of the first region 820, and overlay and display the adjusted image on the first region 820.

The at least one protocol and the at least one manipulation menu item included in the first list 1010 may be included in one list.

Alternatively, as shown in FIG. 10A, the first sub-list 1020 including the at least one protocol and the second sub-list 1030 including the at least one manipulation menu item may be separately included in the first list 1010.

When a first item is selected from the first sub-list 1020 and a second item is continuously selected from the second sub-list 1030, an image corresponding to a protocol included in the first item may be changed according to a manipulation menu option included in the second item. Then, the changed image may be displayed on the first region 820.

For example, when a T1W protocol is selected from the first sub-list 1020 and the filter 1 is continuously selected from the second sub-list 1030 through the UI unit 630, the control unit 610 may display an image obtained by filtering a T1-weighted image corresponding to the T1W protocol by using the filter 1, on the first region 820.

Referring to FIG. 10B, a screen 1050 displayed on the display unit 620 may include the first image 810 and a first list 1051. In detail, when the first region 820 is selected, the medical image providing apparatus 600 may output the first list 1051.

Referring to FIG. 10B, the first list 1051 may include a plurality of sub-lists according to types of a medical imaging system. In FIG. 10B, the first list 1051 includes a first sub-list 1053 corresponding to an MRI system, and a second sub-list 1055 corresponding to a CT system.

Referring to FIG. 10B, the first sub-list 1053 includes at least one of a plurality of MRI protocols 1061 and manipulation menu items 1062 of an MRI image.

As shown in FIG. 10B, a plurality of sub-lists corresponding to a plurality of medical imaging systems may each include protocols and manipulation menu items. For example, the MRI protocols 1061 and the manipulation menu items 1062 may be distinguishably included in the first sub-list 1053, as shown in FIG. 10B. Alternatively, the MRI protocols 1061 and the manipulation menu items 1062 may not be distinguishably included in the first sub-list 1053.

The second sub-list 1055 includes at least one of CT protocols 1065 and manipulation menu items 1066 of a CT image. Examples of the manipulation menu items 1066 include an HU mapping menu and a fat measure menu.

Figure 11:
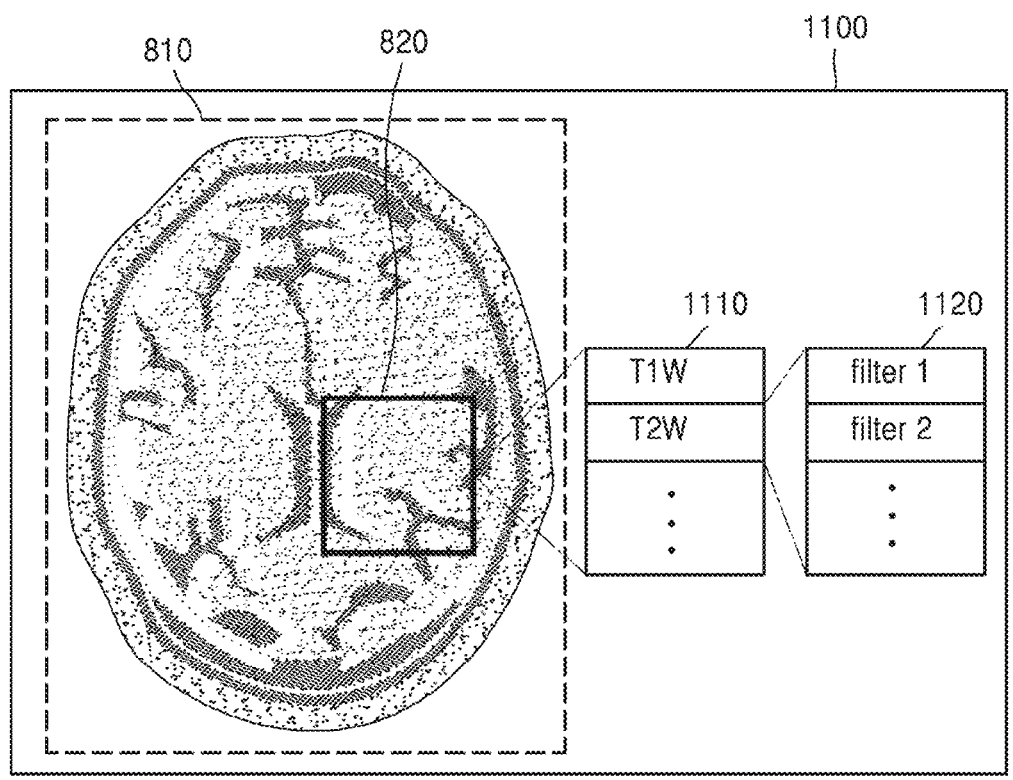
FIG. 11 is a diagram for describing operations of a medical image providing apparatus, according to another exemplary embodiment.

FIG. 11 is a diagram for describing operations of the medical image providing apparatus 600, according to another exemplary embodiment. A list included in a screen 1100 may be in a multistage form.

Referring to FIG. 11, the screen 1100 displayed on the display unit 620 may include the first image 810 and a first list 1110. In detail, when the first region 820 is selected, the medical image providing apparatus 600 may output the first list 1110.

Also, when a predetermined item included in the first list 1110 is activated, at least one manipulation menu item 1120 corresponding to the activated predetermined item is output. Here, the predetermined item is activated by selecting the predetermined item or assigning the predetermined item to select the predetermined item. For example, when a cursor (not shown) is located on the predetermined item by using a mouse to select the predetermined item, the predetermined item may be activated.

In detail, when the predetermined item, for example, a T2W protocol item, included in the first list 1110 is activated, the UI unit 630 may output the manipulation menu item 1120 depending on the T2W protocol item.

Alternatively, when a predetermined item is selected, the predetermined item may be activated. In detail, when a predetermined protocol is selected from the first list 1110, the display unit 620 may display the sub-list 1120 associated with the selected predetermined protocol. For example, when a T2W protocol is selected, the sub-list 1120 associated with the T2W protocol may be displayed through a pop-up window.

Accordingly, the user may additionally select a predetermined manipulation menu item for manipulating a T2-weighted image. For example, when a filter 1 is selected from the sub-list 1120, the control unit 510 may filter a T2-weighted image reconstructed by using image data obtained according to a T2W protocol, and overlay and display the filtered T2-weighted image on the first region 820.

A sub-list including at least one manipulation menu item may be added to each of the protocols included in the first list 1110. In this case, the user may be able to directly select a predetermined manipulation menu item associated with a predetermined protocol without having to first select the predetermined protocol. In other words, the UI unit 630 may output the plurality of protocols included in the first list 1110 after adding the sub-list including the manipulation menu item 1120 to each of the plurality of protocols. In other words, even if a predetermined item included in the first list 1110 is not activated, the manipulation menu item 1120 may be added and output to each of the plurality of items included in the first list 1110.

Figure 12:
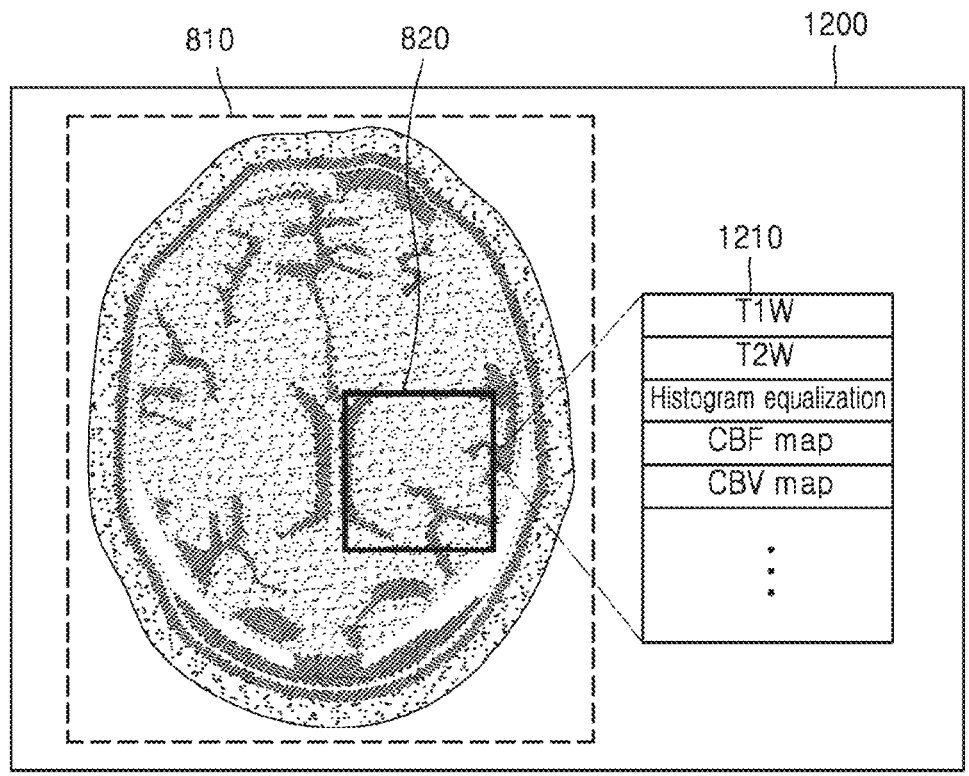
FIG. 12 is a diagram for describing operations of a medical image providing apparatus, according to another exemplary embodiment.

FIG. 12 is a diagram for describing operations of the medical image providing apparatus 600, according to another exemplary embodiment.

Referring to FIG. 12, a screen 1200 displayed on the display unit 620 may include the first image 810 and a first list 1210. In detail, when the first region 820 is selected, the medical image providing apparatus 600 may output the first list 1210.

The first list 1210 may include at least one additional item calculated by using at least one piece of image data obtained by applying at least one protocol.

In detail, an MTT map, a CBV map, and a CBF map may be calculated by using image data obtained by applying a perfusion protocol. An ADC map and a trace map may be calculated by using image data obtained by applying a diffusion protocol.

Accordingly, the first list 1210 includes a plurality of protocols, such as a T1W protocol and a T2W protocol, and a plurality of additional items, such as histogram equalization, a CBF map, and a CBV map, which are calculated by using image data obtained by applying a predetermined protocol.

For example, when a CBF map is selected through the UI unit 630, a CBV map of a region included in the first region 820 may be overlaid and displayed on the first region 820.

Figure 13A:
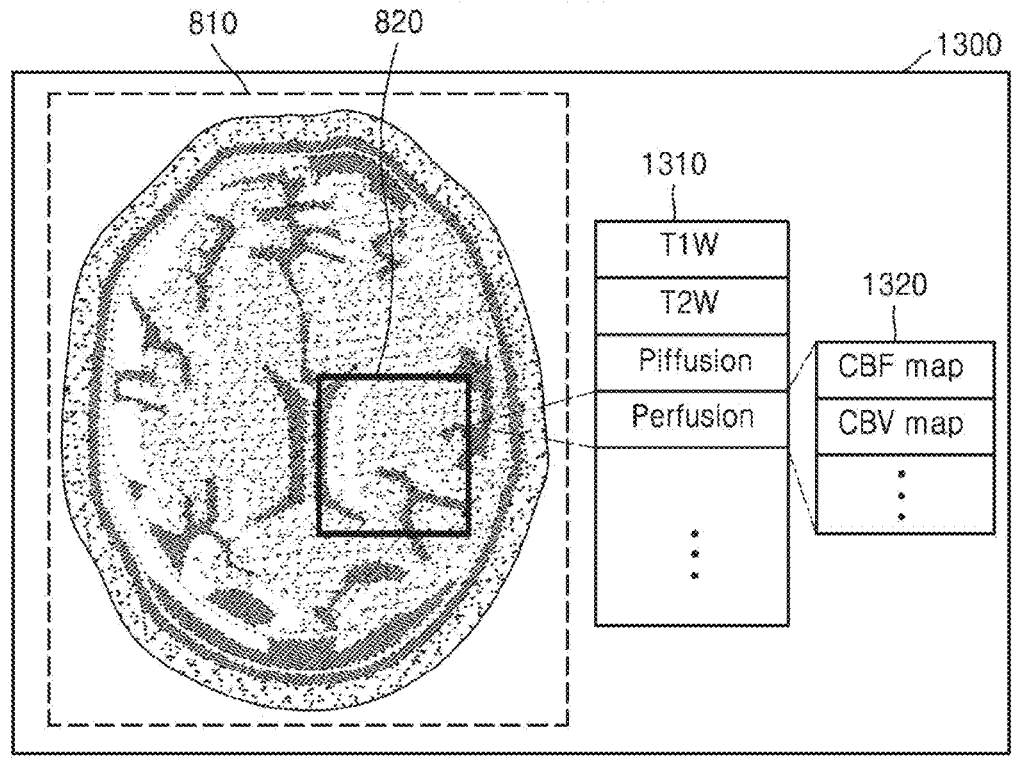
FIG. 13A is a diagram for describing operations of a medical image providing apparatus, according to another exemplary embodiment.

FIG. 13A is a diagram for describing operations of the medical image providing apparatus 600, according to another exemplary embodiment.

Referring to FIG. 13A, a screen 1300 displayed on the display unit 620 may include the first image 810 and a first list 1310. In detail, when the first region 820 is selected, the medical image providing apparatus 600 may output the first list 1310.

In detail, referring to FIG. 13A, the first list 1310 includes at least one protocol. When a predetermined protocol is selected from the first list 1310, an additional item list 1320 including an additional item calculated by using image data obtained by applying the selected predetermined protocol may be output.

For example, when a perfusion protocol is selected, the control unit 610 may display the additional item list 1320 including a CBV map and a CBF map calculated by using image data obtained by scanning an object by applying the perfusion protocol. When the user selected a CBV map from the additional item list 1320, the control unit 610 may overlay and display a CBV map corresponding to a region included in the first region 820, on the first region 820.

Figure 13B:
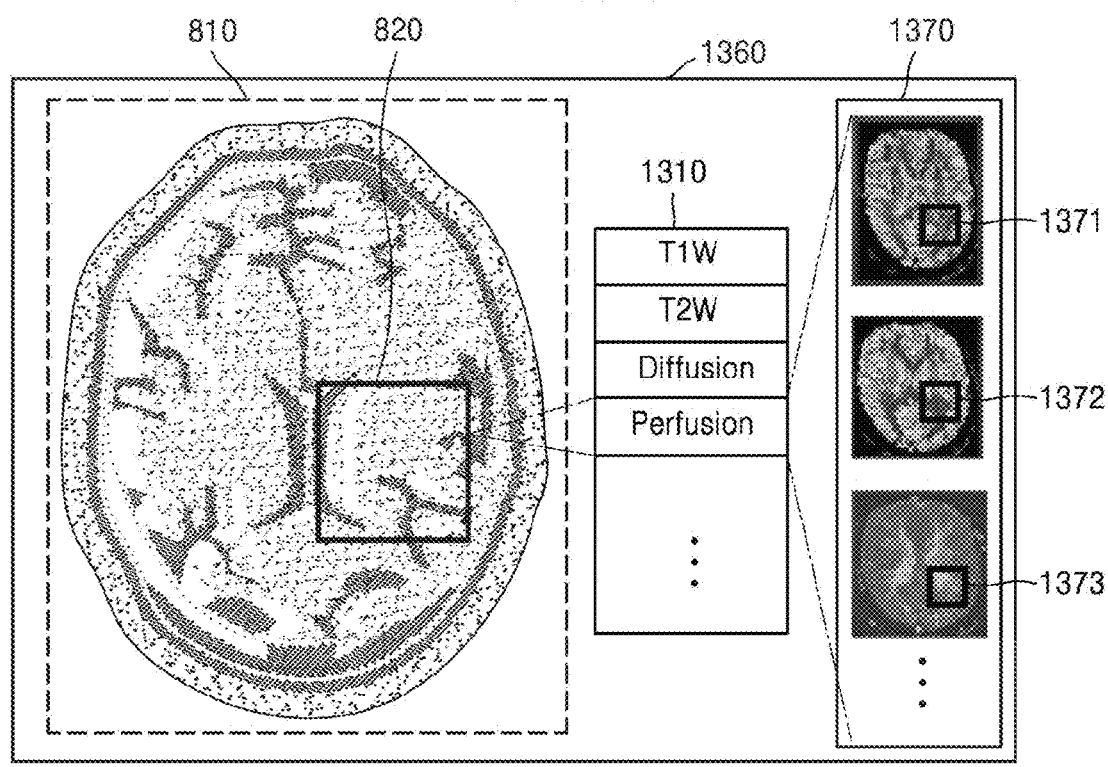
FIG. 13B is a diagram for describing operations of a medical image providing apparatus, according to another exemplary embodiment.

FIG. 13B is a diagram for describing operations of the medical image providing apparatus 600, according to another exemplary embodiment. While describing a screen 1360 of FIG. 13B, descriptions thereof that are the same as those of the screen 1300 of FIG. 13A are not provided.

Referring to FIG. 13B, the screen 1360 displayed by the display unit 620 may include the first image 810 and the first list 1310. In detail, when the first region 820 is selected, the medical image providing apparatus 600 may output the first list 1310. When a predetermined protocol is activated from the first list 1310, a sub-list 1370 including at least one image reconstructed, processed, or calculated by using image data obtained by applying the selected predetermined protocol may be output. In other words, when a predetermined item is selected or is assigned to select the predetermined item from the first list 1310, a protocol included in the predetermined item is activated. Then, the sub-list 1370 including at least one image corresponding to the activated protocol included in the predetermined item is output.

Referring to FIG. 13B, when a perfusion protocol is activated from the first list 1310, the control unit 610 may control the sub-list 1370 including a CBV map 1371, a CBF map 1372, an MTT map 1373, which are calculated by using image data obtained by scanning an object by applying the perfusion protocol, to be displayed. For example, when a user selects the CBV map 1371 from the sub-list 1370, the control unit 610 may overlay and display a partial region included in the first region 820 of the CBV map on the first region 820 of the first image 810.

Figure 14:
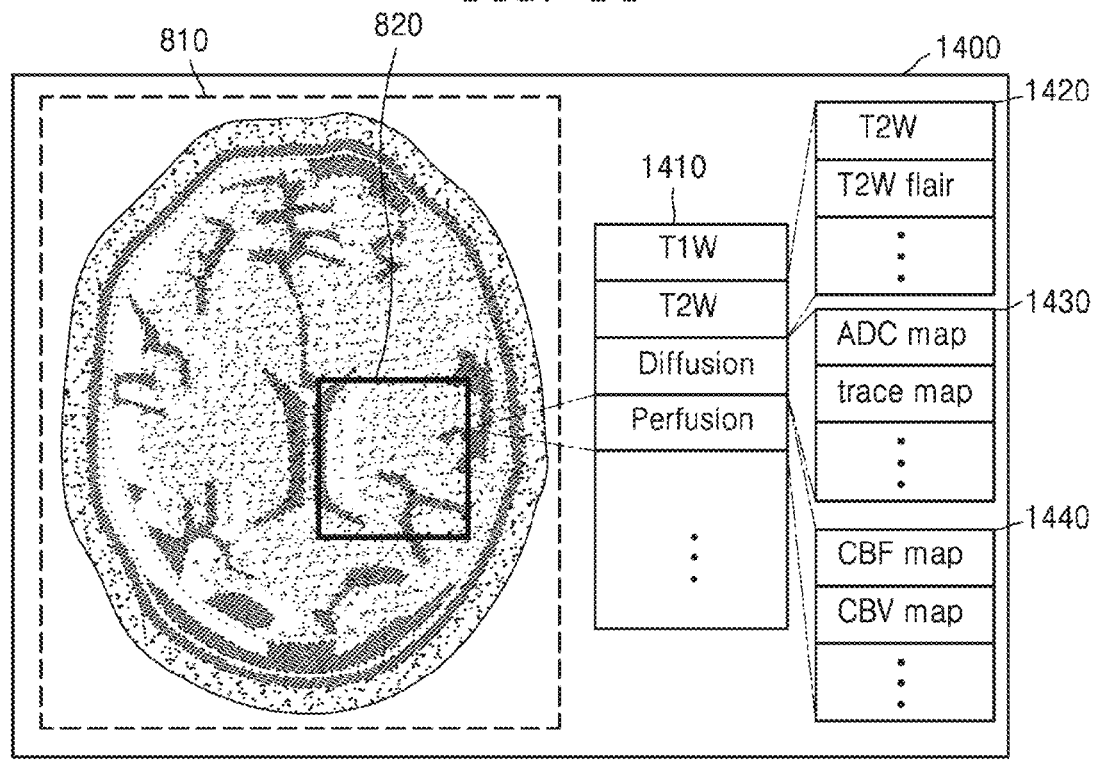
FIG. 14 is a diagram for describing operations of a medical image providing apparatus, according to another exemplary embodiment.

FIG. 14 is a diagram for describing operations of the medical image providing apparatus 600, according to another exemplary embodiment.

Referring to FIG. 14, a screen 1400 displayed on the display unit 620 may include the first image 810 and a first list 1410. In detail, when the first region 820 is selected, the medical image providing apparatus 600 may output the first list 141.

Referring to FIG. 14, sub-lists 1420, 1430, and 1440 including additional items obtained, processed, or calculated by using image data obtained by applying a relevant protocol may be added to the first list 141 according to protocol items, and then the first list 141 may be displayed. In detail, a T2W protocol item and the sub-list 1420 including a T2W flair protocol item may be added to a T2W protocol item. The sub-list 1430 including an ADC map item and a trace map item may be added to a diffusion protocol item, and the sub-list 1440 including a CBF map item and a CBV map item may be added to a perfusion protocol item.

In detail, an ADC map or a trace map may be calculated by using image data obtained by applying a diffusion protocol. Accordingly, an ADC map and a trace map may be added to the sub-list 1430 corresponding to a diffusion protocol item.

Figure 15:
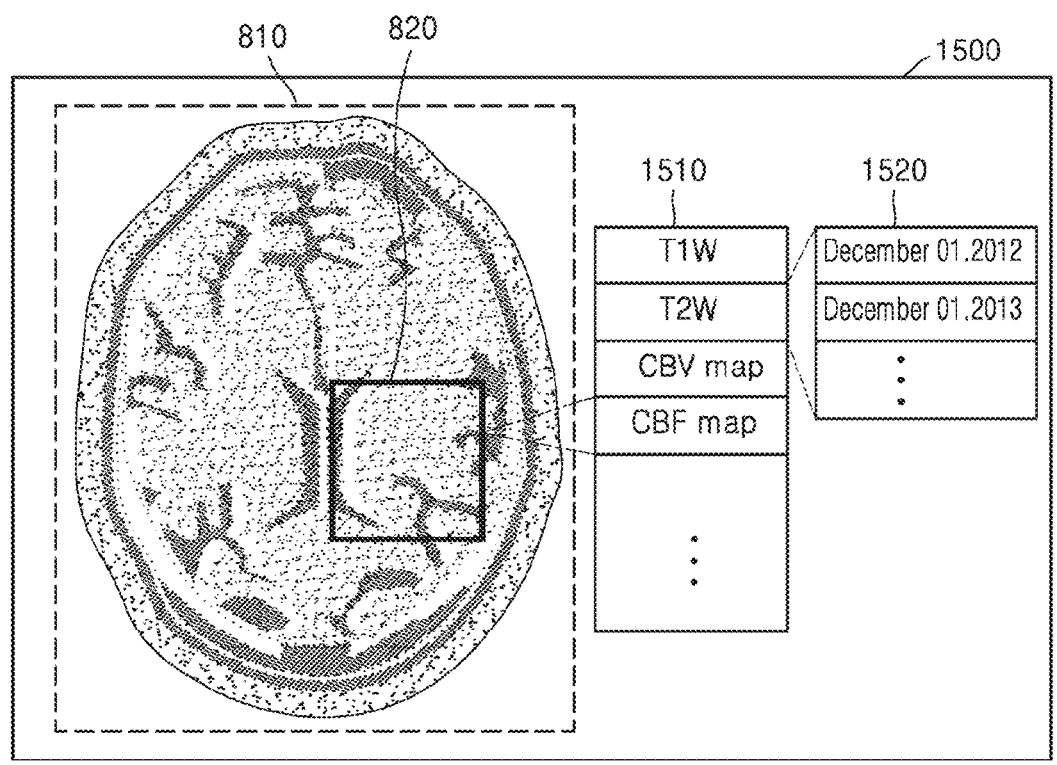
FIG. 15 is a diagram for describing operations of a medical image providing apparatus, according to another exemplary embodiment.

FIG. 15 is a diagram for describing operations of the medical image providing apparatus 600, according to another exemplary embodiment.

Referring to FIG. 15, a screen 1500 displayed on the display unit 620 may include the first image 810 and a first list 1510. In detail, when the first region 820 is selected, the medical image providing apparatus 600 may output the first list 1510. Here, the first list 1510 may include at least one protocol described above. The first list 1510 may further include at least one additional item described above with reference to FIGS. 12 through 14.

The UI unit 630 may output a sub-list 1520 including a plurality of points of time after adding the sub-list 1520 to each of the items included in the first list 1510. In detail, when a predetermined item is selected from the items included in the first list 1510, the UI unit 630 may output the sub-list 1520 including at least one point of time item indicating a point of time when image data or a reconstructed image corresponding to the selected predetermined item is obtained.

For example, let's assume that image data obtained on 1 Dec. 2012 by applying a T2W protocol and image data obtained on 1 Dec. 2013 by applying a T2W protocol are stored in the memory 640, or an image reconstructed by using the image data obtained on 1 Dec. 2012 and an image reconstructed by using the image data obtained on 1 Dec. 2013 are stored in the memory 640. In this case, when a T2W protocol item in the first list 1510 is selected, the UI unit 630 may output the sub-list 1520 including a '1 Dec. 2013' item and a '1 Dec. 2013' item, which are points of time when the image data corresponding to the T2W protocol items are obtained. When the user selects the '1 Dec. 2012' item, the control unit 610 may overlay and display a T2-weighted image reconstructed by using the image data obtained on 1 Dec. 2012, on the first region 820.

Alternatively, when a plurality of points of time items are selected from the sub-list 1520, a plurality of reconstructed images corresponding to the selected plurality of points of time items may be all displayed on the first image 810. In this case, the user may easily determine a disease history of a patient in the first region 820.

Alternatively, a sub-list including at least one point of time item may be added to each item included in the first list 1510. In this case, the user may be able to directly select a point of time item associated with a predetermined item without having to first select the predetermined item in the first list 1510.

The UI unit 630 may add an image display menu including a reconstructed image according to at least one point of time to each item of the first list 1510.

Then, when a predetermined item is selected from the items in the first list 1510, the UI unit 630 may add and output an image display menu including a reconstructed image according to points of time corresponding to the selected predetermined item. In other words, each item of the sub-list 1520 may include a reconstructed image obtained at a point of time displayed on each item. Here, a reconstructed image included in each item of the sub-list 1520 may be a whole image of an object or a partial image corresponding to the first region 820.

Figure 16:
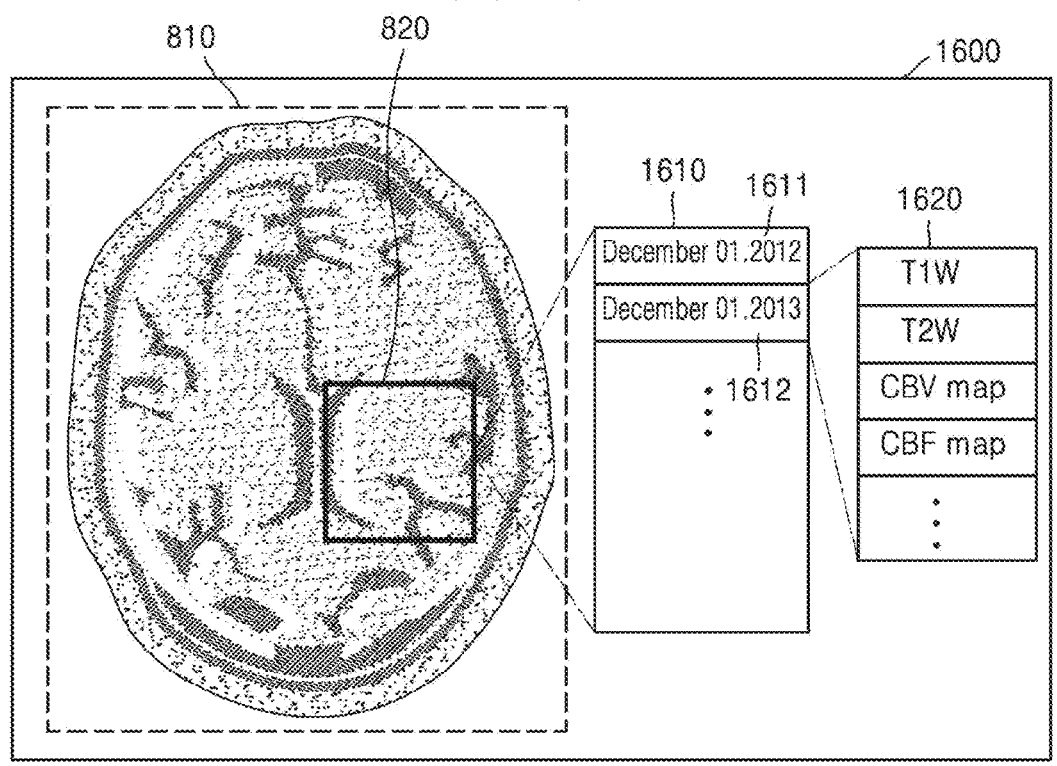
FIG. 16 is a diagram for describing operations of a medical image providing apparatus, according to another exemplary embodiment.

FIG. 16 is a diagram for describing operations of the medical image providing apparatus 600, according to another exemplary embodiment.

Referring to FIG. 16, a screen 1600 displayed on the display unit 620 may include the first image 810 and a first list 1610. In detail, when the first region 820 is selected, the medical image providing apparatus 600 may output the first list 1610.

Referring to FIG. 16, the first list 1610 may include at least one item indicating a point of time when image data or reconstructed image obtained by applying at least one protocol is obtained. Here, at least one point of time item included in the first list 1610 is related to a medical image of the same patient and the same region.

For example, a first item 1611 in the first list 1610 is related to a medical image captured on 1 Dec. 2012, and a second item 1612 is related to a medical image captured on 1 Dec. 2013.

In detail, when the second item 1612 is selected through the UI unit 630, the second item 1612 may include a sub-list 1620 including image data or a reconstructed image obtained by applying a predetermined protocol on 1 Dec. 2013. When the user selects a 'T2W' item from the sub-list 1620, the control unit 610 overlays and displays a T2-weighted image on the first region 820 photographed on 1 Dec. 2013.

In detail, when the memory 640 distinguishably stores image data corresponding to medical images or protocols regarding the same body region of the same patient according to photographing points of time, the control unit 610 may read information about a photographing point of time and a protocol from the memory 640. Then, the UI unit 630 may output the first list 1610 and the sub-list 1620, as shown in FIG. 16, by using the information read by the control unit 610.

Figure 17:
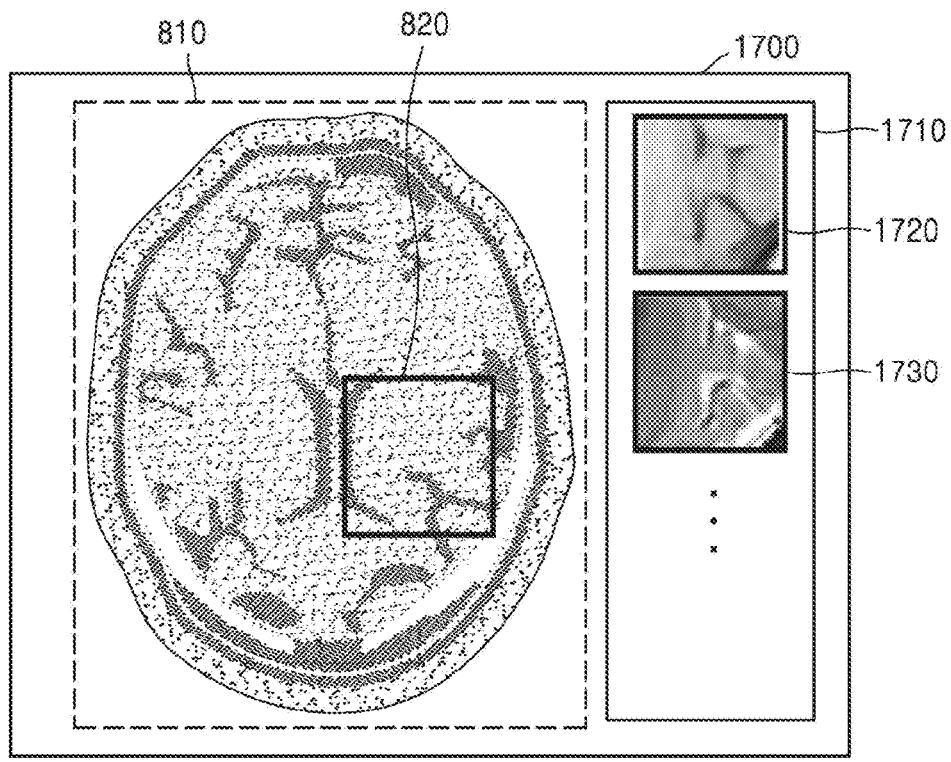
FIG. 17 is a diagram for describing operations of a medical image providing apparatus, according to another exemplary embodiment.

FIG. 17 is a diagram for describing operations of the medical image providing apparatus 600, according to another exemplary embodiment.

Referring to FIG. 17, a screen 1700 displayed on the display unit 620 may include the first image 810 and a second list 1710. In detail, when the first region 820 is selected, the medical image providing apparatus 600 may output the second list 1710.

In the medical image providing apparatus 600, when the first region 820 included in the first image 810 is selected, the UI unit 630 may output the second list 1710 including at least one reconstructed image corresponding to a protocol. Hereinafter, a list including a reconstructed image according to at least one protocol will be referred to as the second list 1710.

The UI unit 630 may receive a selection on a predetermined reconstructed image included in the second list 1710. It is assumed that the selected predetermined reconstructed image is a first reconstructed image. Then, the control unit 610 may overlay and display a second image on the first region 820 of the first image 810, by using the first reconstructed image.

In detail, the second image overlaid on the first region 820 is an image included in an area corresponding to a predetermined region of an object included in the first region 820, with respect to the first reconstructed image.

Referring to FIG. 17, reconstructed images 1720 and 1730 included in the second list 1710 may be partial images corresponding to the first region 820. In detail, the reconstructed images 1720 and 1730 may equally correspond to the regions 711 and 721 described above with reference to FIG. 7A, respectively.

In detail, when the user selects any one of the reconstructed images 1720 and 1730 included in the second list 1710, the selected reconstructed image 1720 or 1730 is overlaid and displayed on the first region 820.

For example, the user may select a first reconstructed image by clicking and dragging any one of the reconstructed images 1720 and 1730 included in the second list 1710. Alternatively, the user may select a first reconstructed image by doubling clicking any one of the reconstructed images 1720 and 1730. A method of selecting one of the reconstructed images 1720 and 1730 may differ based on an input device included in the UI unit 630, examples of the input device including a keyboard, a mouse, and a touch pad.

In FIG. 17, the first region 820 that is one partial region is selected, but alternatively, a plurality of partial regions may be selected from the first image 810. In this case, a reconstructed image to be overlaid may be individually selected according to the selected plurality of partial regions.

The second list 1710 may include at least one manipulation menu item (not shown) for manipulating at least one reconstructed image or the first region 820 of the first image 810. Since the manipulation menu item has been described above with reference to FIG. 10A, details thereof are not repeated here.

Alternatively, the second list 1710 may include a first sub-list (not shown) including at least one reconstructed image, and a second sub-list (not shown) including at least one manipulation menu item for manipulating the first region 820. Here, the first and second sub-lists may be distinguishably displayed as shown in FIG. 10A.

Alternatively, the second list 1710 may include at least one additional image (not shown) generated by using at least one piece of image data obtained by applying at least one protocol.

Here, the additional image is information obtained by using image data obtained by applying a protocol as described above, and may be a CBV map, a CBF map, or a histogram equalization image. The additional image that may be included in the second list 1710 equally corresponds to an image corresponding to the additional item described with reference to FIG. 12.

Figure 18A:
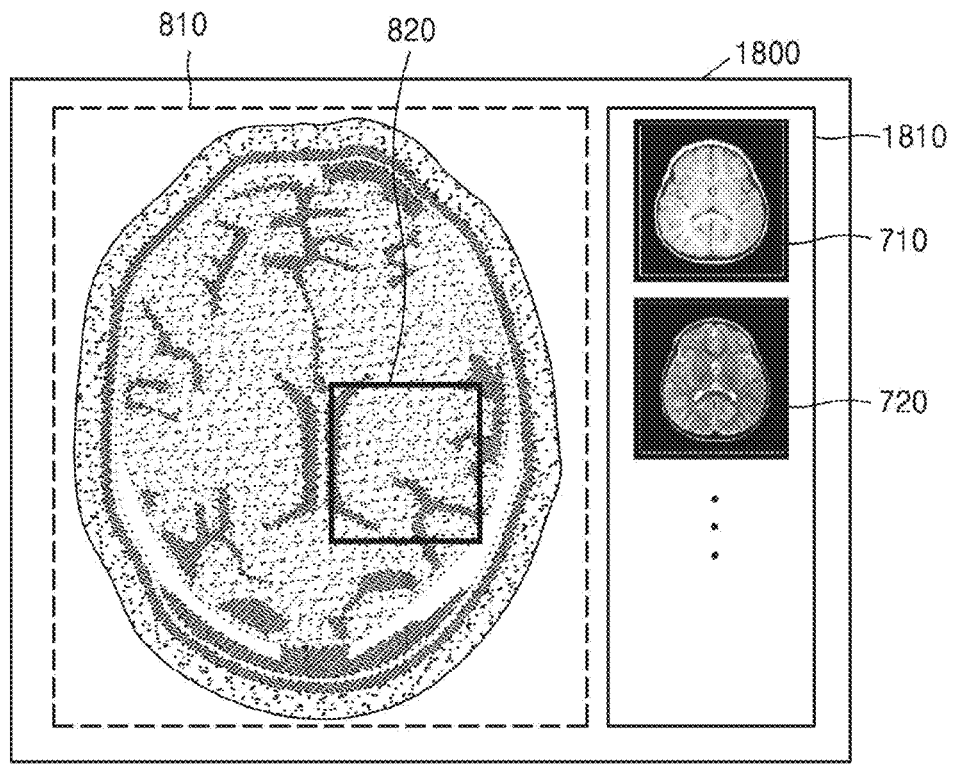
FIGS. 18A and 18B show diagrams for describing operations of a medical image providing apparatus, according to another exemplary embodiment.
Figure 18B:
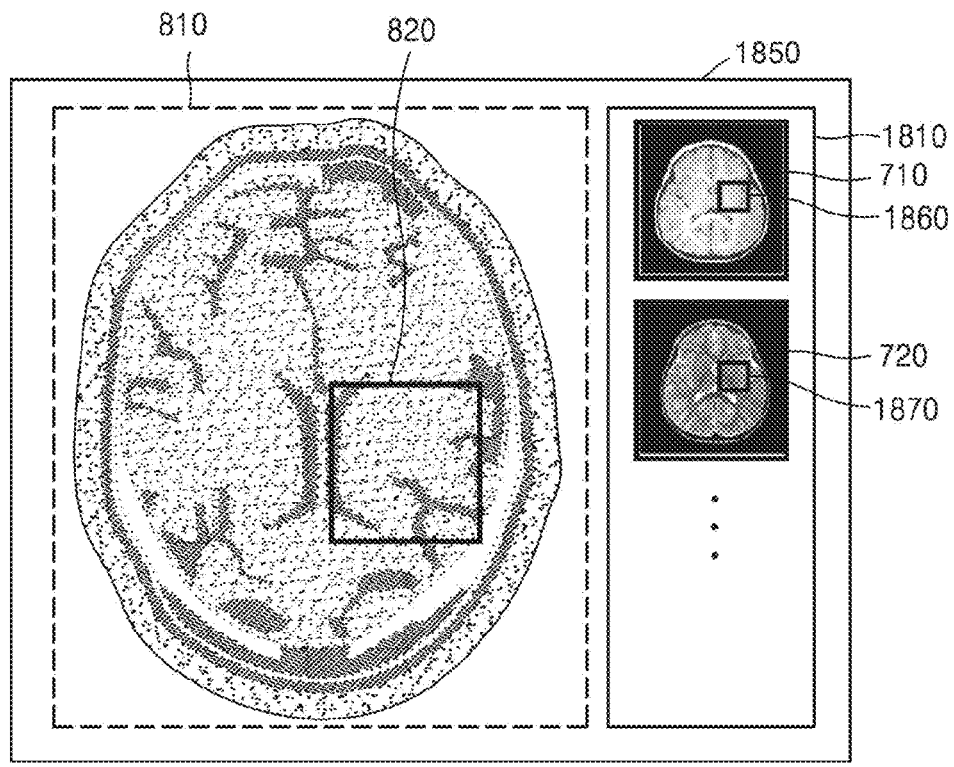

FIGS. 18A and 18B show diagrams for describing operations of the medical image providing apparatus 600, according to another exemplary embodiment.

Referring to FIG. 18A, a screen 1800 displayed on the display unit 620 may include the first image 810 and a second list 1810. In detail, when the first region 820 is selected, the medical image providing apparatus 600 may output the second list 1810.

Referring to FIG. 18A, the second list 1810 may include at least one reconstructed image corresponding to a protocol. Here, the reconstructed image included in the second list 1810 may be a whole image of an object.

In detail, a reconstructed image 1820 and a reconstructed image 1830 included in the second list 1810 may equally correspond to the T1-weighted image 710 and the T2-weighted image 720 of FIG. 7A, respectively.

When the user selects any one of the reconstructed images 1820 and 1830 included in the second list 1810, the control unit 610 may overlay and display a region of the selected reconstructed image 1820 or 1830, which correspond to the first region 820, on the first region 820.

Referring to FIG. 18B, a screen 1850 shows a reconstructed image included in the second list 1810 may be a whole image of an object, and a region corresponding to the first region 820 may be displayed on reconstructed images, i.e., the T1 and T2-weighted images 710 and 720, included in the second list 1810.

Referring to FIG. 18B, a region 1860 corresponding to the first region 820 may be displayed in the T1-weighted image 710, and a region 1870 corresponding to the first region 820 may be displayed in the T2-weighted image 720.

Figure 19:
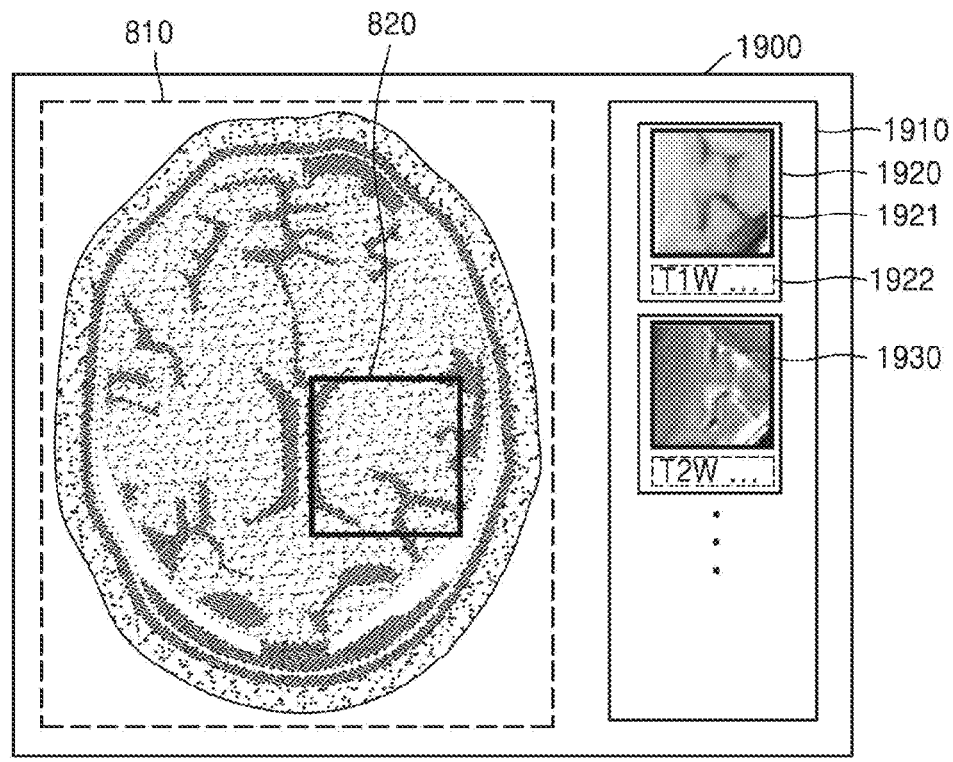
FIG. 19 is a diagram for describing operations of a medical image providing apparatus, according to another exemplary embodiment.

FIG. 19 is a diagram for describing operations of the medical image providing apparatus 600, according to another exemplary embodiment.

Referring to FIG. 19, a screen 1900 displayed on the display unit 620 may include the first image 810 and a second list 1910. In detail, when the first region 820 is selected, the medical image providing apparatus 600 may output the second list 1910.

In the second list 1910, each of items 1920 and 1930 may include a reconstructed image 1921 according to protocols, and information 1922 about the reconstructed image 1921. Here, the information 1922 may include a protocol of the reconstructed image 1921. The information 1922 may further include at least one of a point of time when the reconstructed image 1920 is obtained, and a disease history of a patient. The reconstructed image 1921 may be a whole image or partial image of an object.

Figure 20:
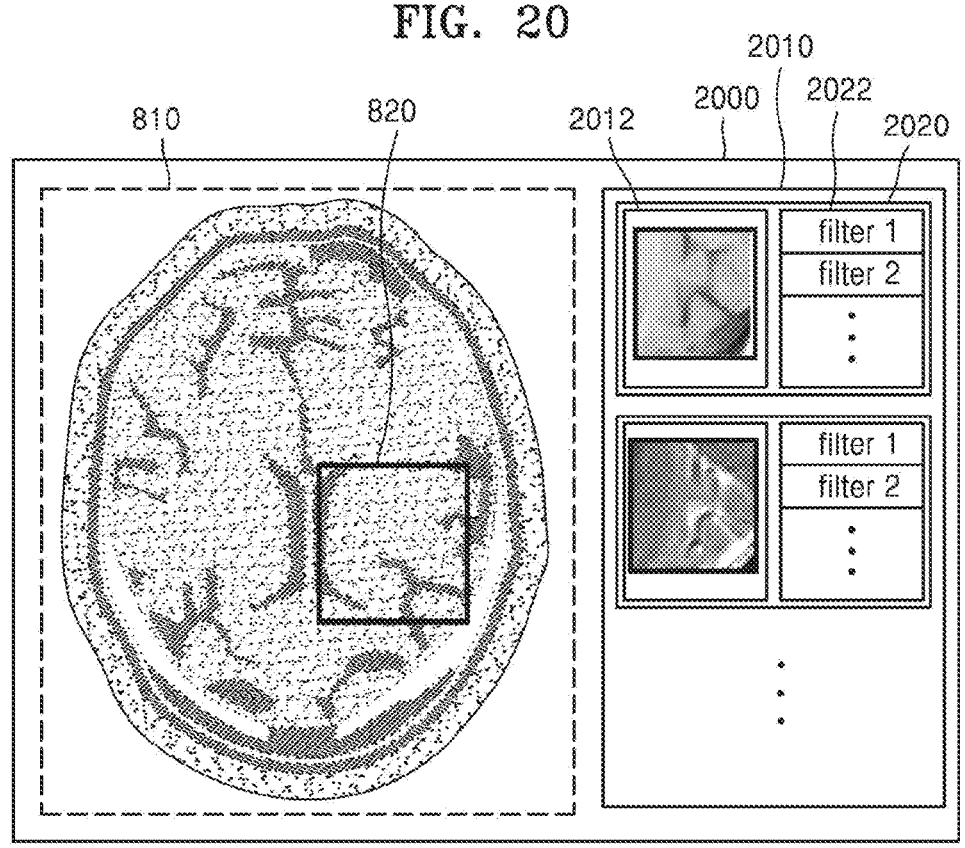
FIG. 20 is a diagram for describing operations of a medical image providing apparatus, according to another exemplary embodiment.

FIG. 20 is a diagram for describing operations of the medical image providing apparatus 600, according to another exemplary embodiment.

Referring to FIG. 20, a screen 2000 displayed on the display unit 620 may include the first image 810 and a second list 2010. In detail, when the first region 820 is selected, the medical image providing apparatus 600 may output the second list 2010.

The UI unit 630 may generate at least one manipulation menu item for manipulating each of at least one reconstructed image, and may add the generated at least one manipulation menu item to each of the at least one reconstructed image included in the second list 2010.

For example, each item, for example, a first item 2020, included in the second list 2010 may include a reconstructed image 2012 and a manipulation menu item 2022.

When the user selects a filter 1 included in the first item 2020, the control unit 610 may filter the reconstructed image 2012 by using the filter 1, and overlay and display the filtered reconstructed image 2012 on the first region 820.

Figure 21:
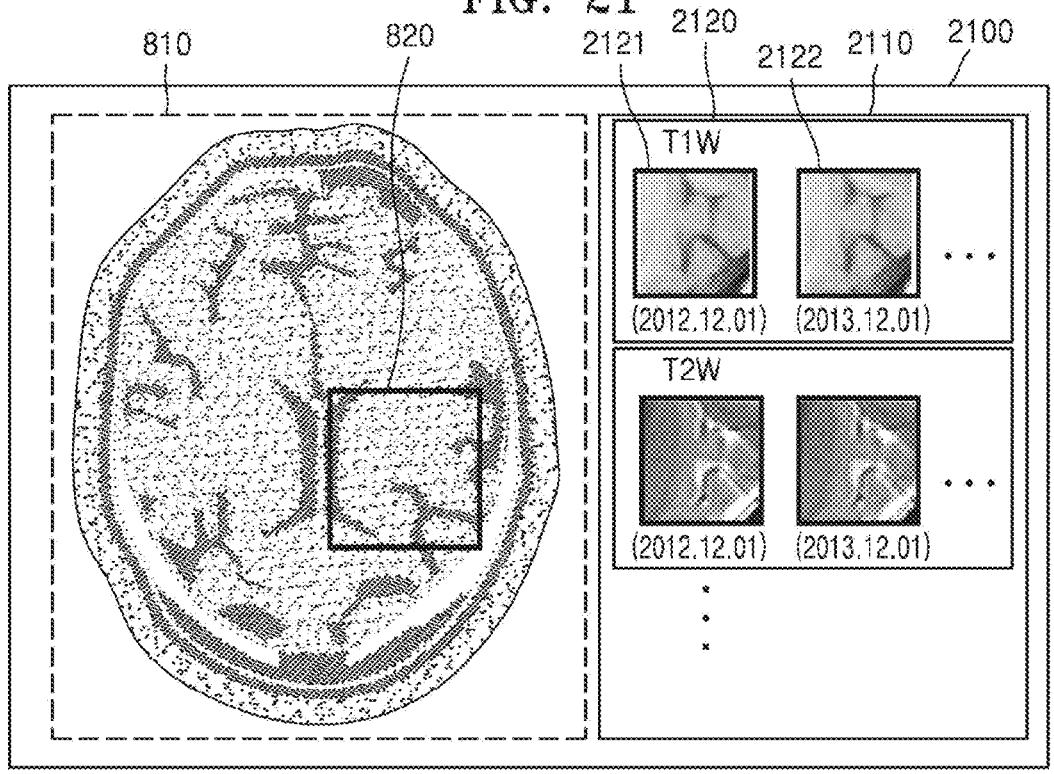
FIG. 21 is a diagram for describing operations of a medical image providing apparatus, according to another exemplary embodiment.

FIG. 21 is a diagram for describing operations of the medical image providing apparatus 600, according to another exemplary embodiment.

Referring to FIG. 21, a screen 2100 displayed on the display unit 620 may include the first image 810 and a second list 2110. In detail, when the first region 820 is selected, the medical image providing apparatus 600 may output the second list 2110.

Referring to FIG. 21, each item of the second list 2110 may include at least one reconstructed image according to points of time corresponding to a protocol. Here, a 'reconstructed image according to points of time' denotes a medical image captured and reconstructed at a predetermined point of time.

For example, a first item 2120 of the second list 2110 may include a plurality of T1-weighted images. In detail, the first item 2120 may include a T1-weighted image 2121 captured on 1 Dec. 2012, and a T1-weighted image 2122 captured on 1 Dec. 2013.

For example, when the user selects the T1-weighted image 2121, the T1-weighted image 2121 captured on 1 Dec. 2012 is overlaid and displayed on the first region 820.

Figure 22A:
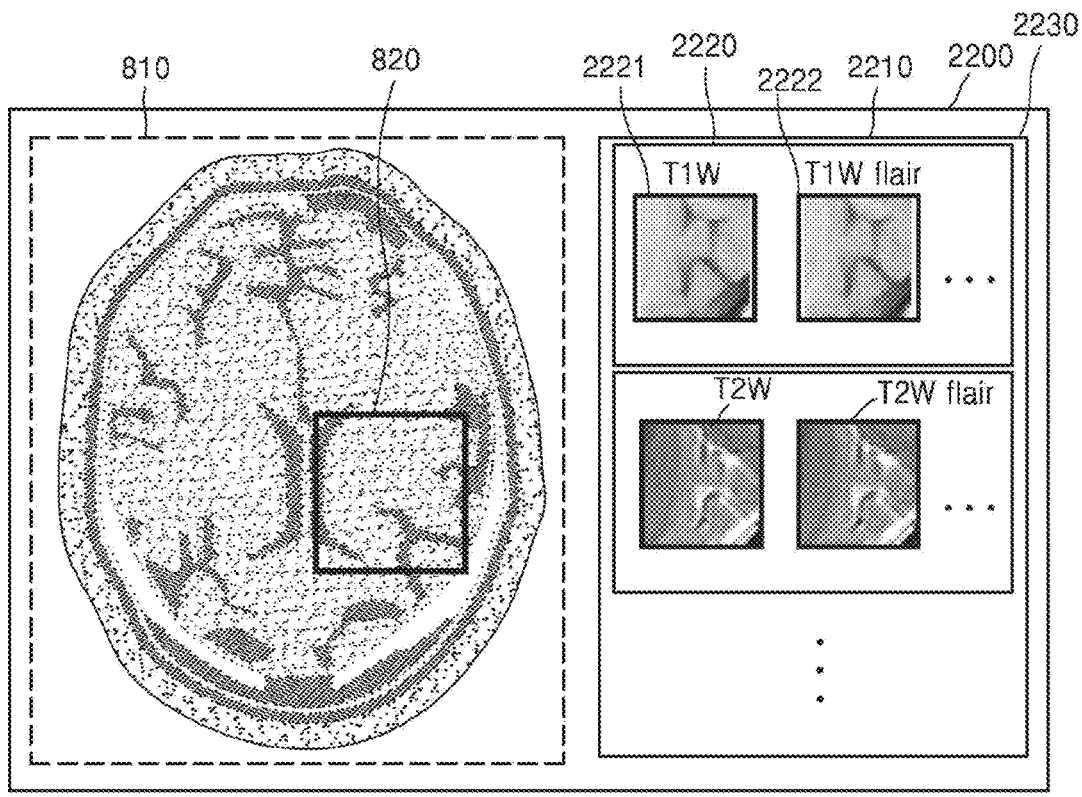
FIG. 22A is a diagram for describing operations of a medical image providing apparatus, according to another exemplary embodiment.

FIG. 22A is a diagram for describing operations of the medical image providing apparatus 600, according to another exemplary embodiment.

Referring to FIG. 22A, a screen 2200 displayed on the display unit 620 may include the first image 810 and a second list 2210. In detail, when the first region 820 is selected, the medical image providing apparatus 600 may output the second list 2210.

Each item included in the second list 2210 may include at least one image corresponding to the same protocol. In detail, each item included in the second list 2210 may include sub-items reconstructed or calculated by using image data obtained by the same protocol. In detail, a first item 2220 of the second list 2210 may include a T1-weighted image 2221 and a T1 weighted flair image 2222, which are reconstructed by using image data obtained by a T1 protocol. A second item 2230 may include a CBF map and a CBV map, which are generated by using image data obtained by a perfusion protocol. Also, an image included in the second list 2210 may be a partial image indicating a region of an object included in the first region 820, or an image indicating the object corresponding to the first image 810. In FIG. 22A, the second list 2210 includes the partial image.

For example, when the user selects the T1-weighted image 2221, the T1-weighted image 2221 may be overlaid and displayed on the first region 820.

The control unit 610 may provide a preview function of a reconstructed image according to protocols, even before a predetermined protocol is selected.

In detail, the control unit 610 may display a preview menu of a reconstructed image corresponding to a predetermined item included in a first list that is focused by using an input device included in the UI unit 630.

A preview function will now be described in detail with reference to FIGS. 23 and 24. It is assumed that a preview menu is a reconstructed image corresponding to a predetermined item that is focused.

Figure 22B:
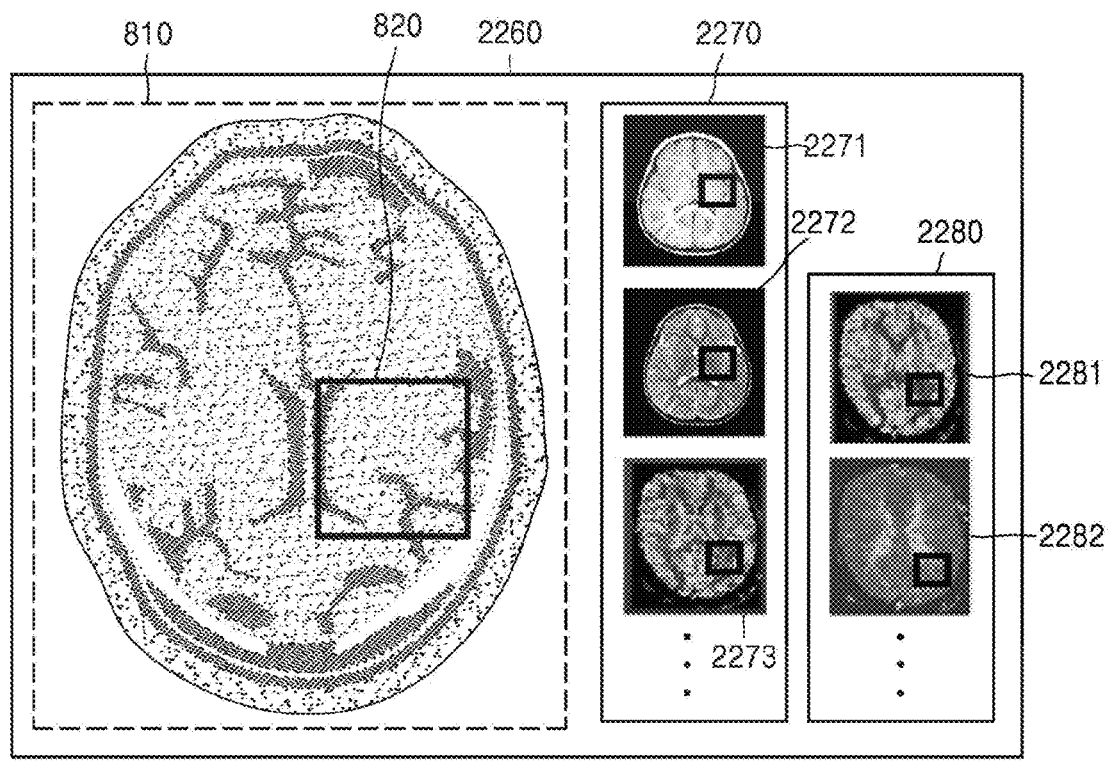
FIG. 22B is a diagram for describing operations of a medical image providing apparatus, according to another exemplary embodiment.

FIG. 22B is a diagram for describing operations of the medical image providing apparatus 600, according to another exemplary embodiment. The control unit 620 may control a list included in a screen 2260 to be output in a multistage form.

Referring to FIG. 22B, the screen 2260 displayed by the display unit 620 may include the first image 810 and a second list 2270. In detail, when the first region 820 is selected, the medical image providing apparatus 600 may output the second list 2270.

The second list 2270 may include a T1-weighted image 2271 obtained according to a T1W protocol, a T2-weighted image 2272 obtained according to a T2W protocol, and a CBV map 2273 obtained according to a perfusion protocol.

Also, when a predetermined item included in the second list 2270 is activated, a sub-list 2280 including at least one image corresponding to at least one of an additional item and a manipulation menu item related to the activated predetermined item may be output.

Referring to FIG. 22B, when the CBV map 2273 obtained according to the perfusion protocol is activated from the second list 2270, the control unit 620 may control the sub-list 2280 including at least one image corresponding to at least one of an additional item and a manipulation menu item related to the perfusion protocol to be output. In FIG. 22B, the sub-list 2280 includes a CBF map 2281 and an mTT map 2282, which are images calculated by using image data obtained by applying the perfusion protocol.

When one of the images included in the second list 2270 or the sub-list 2280 is selected, the control unit 620 may control a partial image corresponding to the first region 820 of the selected image to be overlaid and displayed on the first region 820 of the first image 810.

Figure 23:
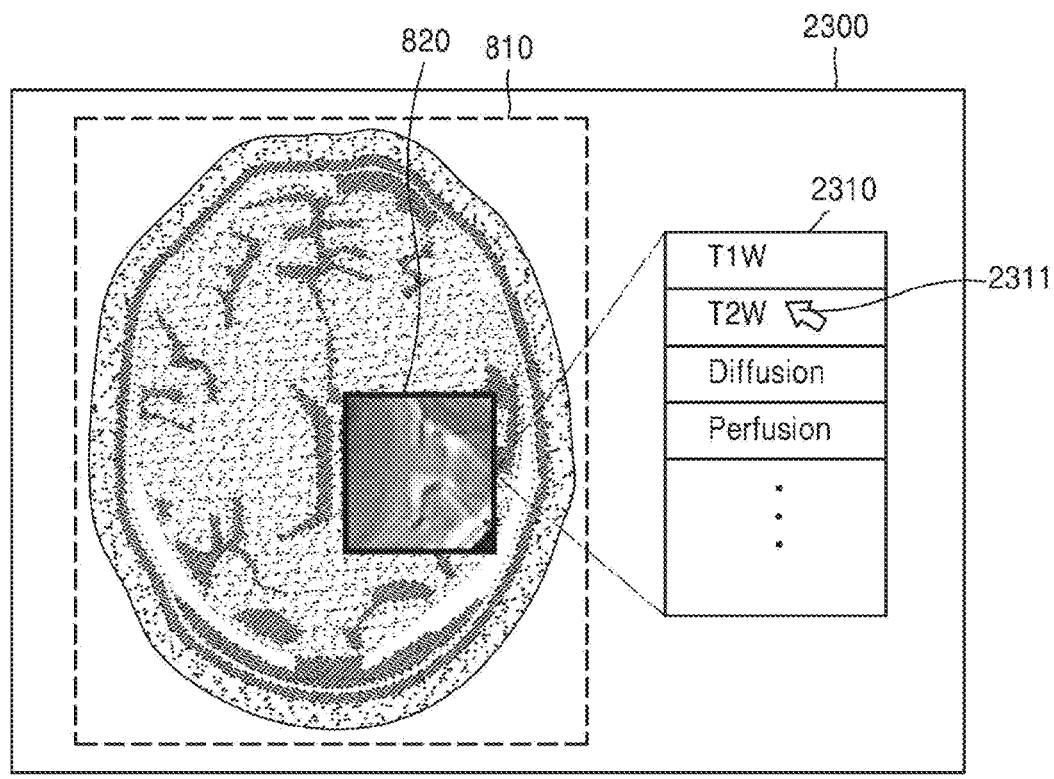
FIG. 23 is a diagram for describing operations of a medical image providing apparatus, according to another exemplary embodiment.

FIG. 23 is a diagram for describing operations of the medical image providing apparatus 600, according to another exemplary embodiment.

Referring to FIG. 23, a screen 2300 displayed on the display unit 620 includes the first image 810 and a first list 2310. In detail, when the first region 820 is selected from the first image 810, the medical image providing apparatus 600 may output the first list 2310 including at least one protocol.

The user may focus a predetermined item of the first list 2310 by using an input device included in the UI unit 630. As described above, when the input device is a mouse, a keyboard, or a touch pad, the user may select the predetermined item by using a cursor 2311 corresponding to manipulation of the input device. In detail, the user may locate the cursor 2311 on the predetermined item, and select the predetermined item through the input device. For example, when the user selects the predetermined item by using a mouse, the user may move the cursor 2311 to a desired location and then double-click the mouse so as to select a 'T2W protocol' item where the cursor 2311 is located.

In this case, referring to FIG. 23, a reconstructed image corresponding to a protocol focused by the user may be displayed even before the first region 820 is selected.

When the user locates the cursor 2311 on the predetermined item of the first list 2310, a reconstructed image corresponding to the predetermined item may be overlaid and displayed on the first region 820 even before the user selects the predetermined item by determining that the predetermined item where the cursor 2311 is located is activated. When the cursor 2311 moves to another item, a reconstructed image overlaid on the first region 820 may correspondingly change.

The user may pre-view an image corresponding to a protocol corresponding to a predetermined item on the first region 820 by locating the cursor 2311 on the predetermined item, and finally select or not select the predetermined item.

Figure 24A:
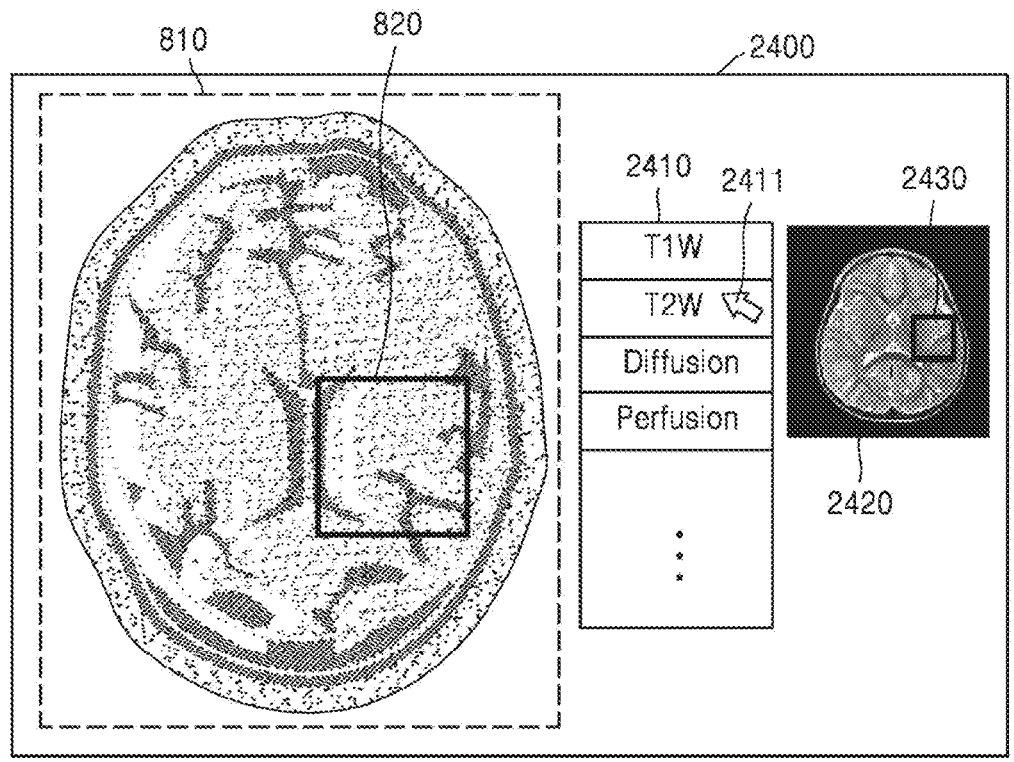
FIGS. 24A and 24B show diagrams for describing operations of a medical image providing apparatus, according to another exemplary embodiment.
Figure 24B:
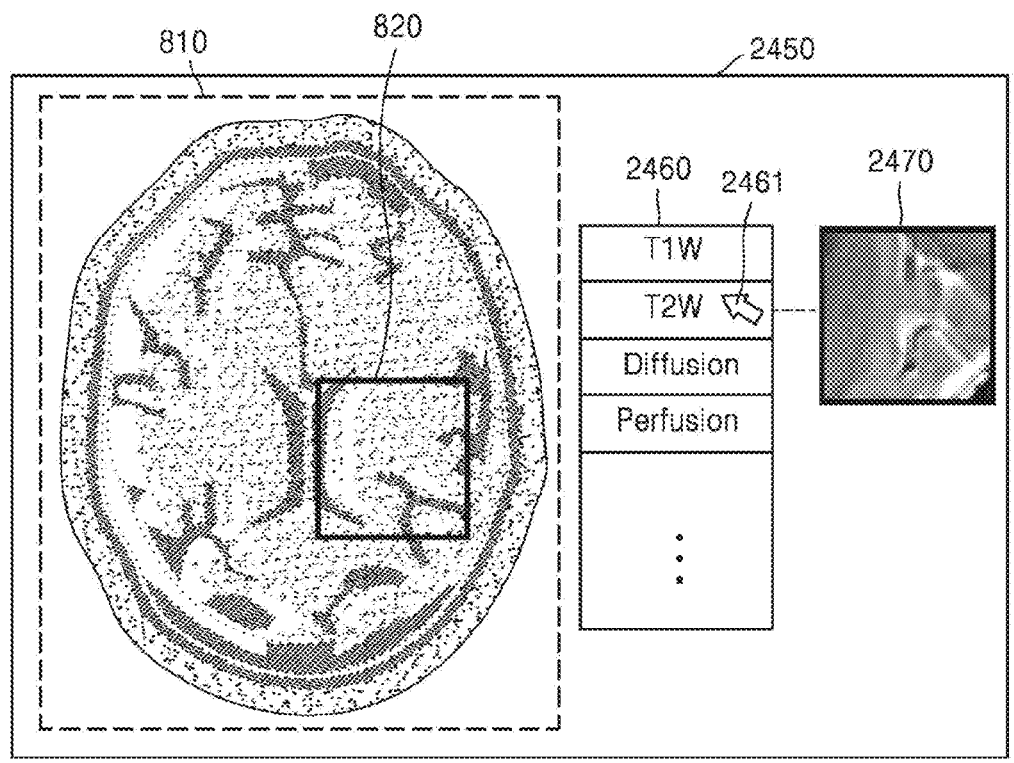

FIGS. 24A and 24B show diagrams for describing operations of the medical image providing apparatus 600, according to another exemplary embodiment.

Referring to FIG. 24A, a screen 2400 displayed on the display unit 620 includes the first image 810 and a first list 2410. In detail, when the first region 820 is selected from the first image 810, the medical image providing apparatus 600 may output the first list 2410 including at least one protocol.

Referring to FIG. 24A, when the user focuses a predetermined item of the first list 2410 by using an input device included in the UI unit 630, the control unit 610 may display a reconstructed image 2420 corresponding to the focused predetermined item. Here, the reconstructed image 2420 may be an image corresponding to the first image 810 or a partial image corresponding to the first region 820. In FIG. 24A, the reconstructed image 2420 is the image corresponding to the first image 810.

In detail, when the user locates a cursor on a predetermined item of the first list 2410 by using a mouse, the control unit 610 may perform a preview function by displaying a reconstructed image corresponding to the predetermined item where the cursor is located, on the screen 2400. When the location of the cursor is changed to another item, a reconstructed image displayed on the screen 2400 may be changed accordingly. Accordingly, in FIG. 24A, the reconstructed image 2420 that is a T2-weighted image corresponding to a 'T2W protocol' where a cursor 2411 is located may be displayed on the screen 2400.

Here, the reconstructed image 2420 may be a whole image corresponding to a predetermined protocol, and a region 2430 corresponding to the first region 820 may be displayed.

Referring to FIG. 24B, when the user focuses a predetermined item of a first list 2460 by using an input device included in the UI unit 630, the control unit 610 may display a reconstructed image 2470 corresponding to the focused predetermined item. Accordingly, the reconstructed image 2470 that is a T2-weighted image corresponding to a 'T2W protocol' where a cursor 2461 is located may be displayed on a screen 2450.

Here, the reconstructed image 2470 is reconstructed by applying the T2W protocol, and may include a region corresponding to the first region 820.

Figure 25A:
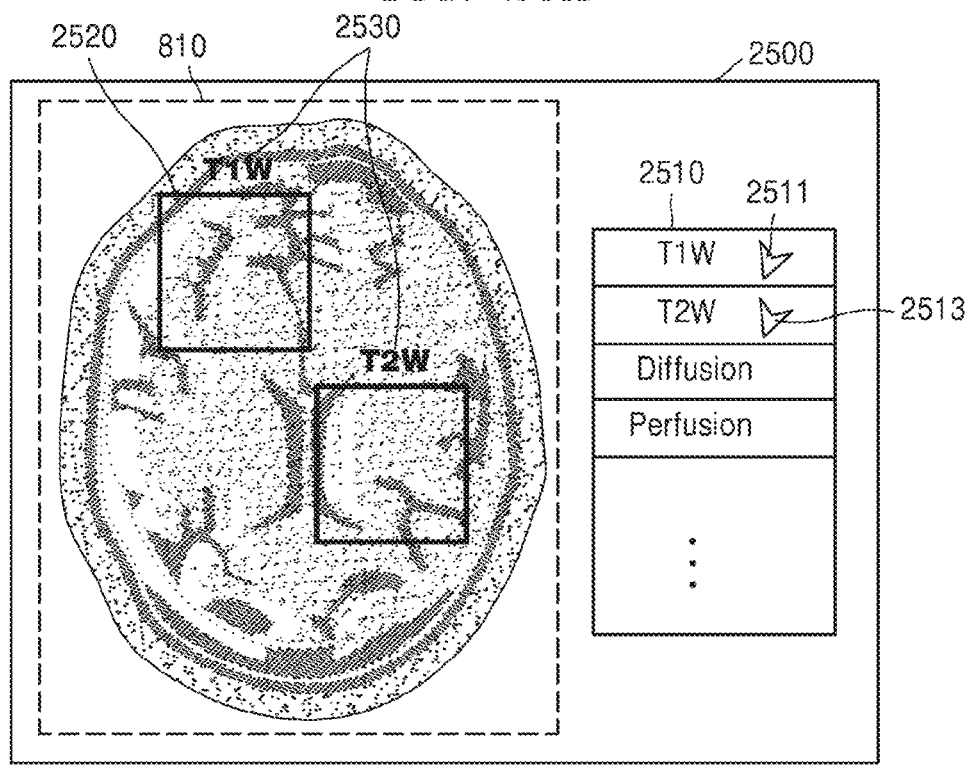
FIGS. 25A and 25B show diagrams for describing operations of a medical image providing apparatus, according to another exemplary embodiment.
Figure 25B:
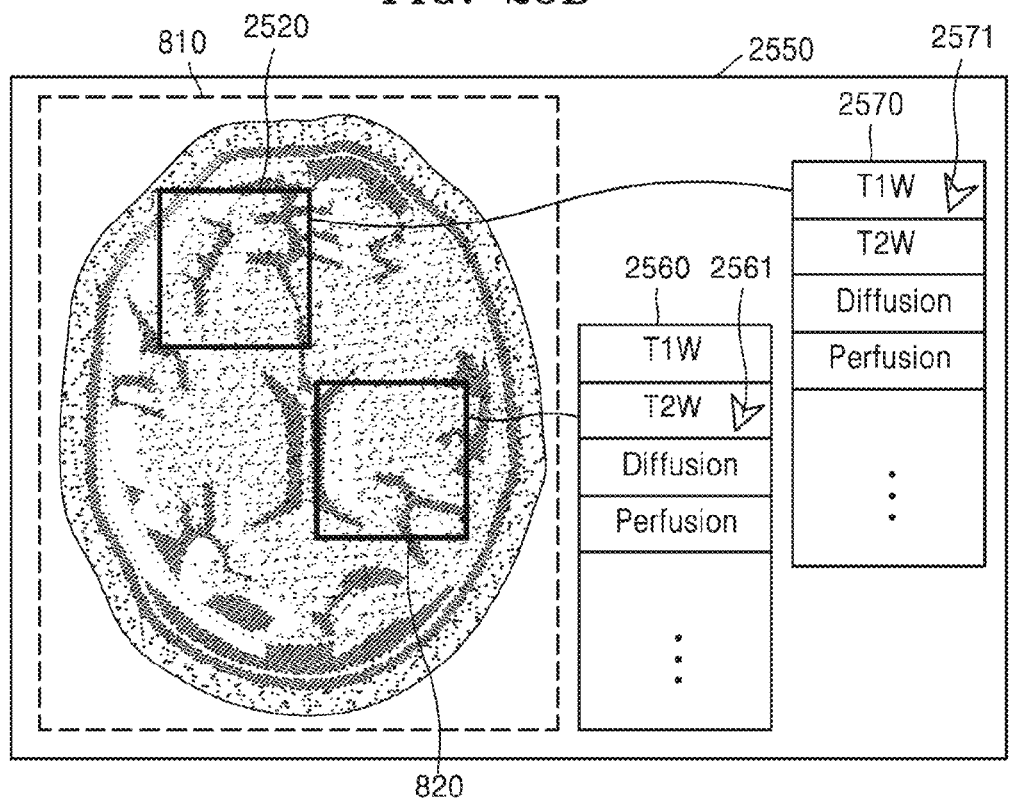

FIGS. 25A and 25B show diagrams for describing operations of the medical image providing apparatus 600, according to another exemplary embodiment.

As described above with reference to FIG. 8A, a plurality of partial regions may be selected from the first image 810 via a user's setting or automatic extraction.

Referring to FIG. 25A, a screen 2500 displayed on the display unit 620 may include the first image 810 and a first list 2510. In detail, when a plurality of first regions 820 and 2520 are selected, the medical image providing apparatus 600 may output the first list 2510 for selecting a protocol corresponding to each of the first regions 820 and 2520.

In order to select protocols respectively corresponding to a plurality of partial regions, the plurality of partial regions may be sequentially highlighted.

In detail, when the first region 2520 on the left is highlighted, a protocol of an image to be overlaid on the first region 2520 may be first selected through the first list 2510. After the protocol corresponding to the first region 2520 on the left is selected, the first region 820 on the right may be continuously highlighted. Then, the user may select a protocol of an image to be overlaid on the first region 820 on the right through the first list 2510.

Referring to FIG. 25A, a T1W protocol is selected as denoted by a reference numeral 2511 correspondingly to the first region 2520 on the left, and a T2W protocol is selected as denoted by a reference numeral 2513 correspondingly to the first region 820 on the right. Here, protocols selected correspondingly to a plurality of partial regions may be displayed as shown in regions 2530 so that the user easily recognizes the selected protocols. After the protocols are selected as such, images according to the protocols corresponding to the plurality of partial regions may be overlaid and displayed on the plurality of partial regions.

Referring to FIG. 25B, a screen 2550 displayed on the display unit 620 may include the first image 810 and the plurality of first lists 2560 and 2570 for respectively selecting the first regions 820 and 2520. In detail, when the first regions 820 and 2520 are selected, the medical image providing apparatus 600 may output the first lists 2560 and 2570 for respectively selecting protocols corresponding to the first regions 820 and 2520.

Referring to FIG. 25B, the screen 2550 may include the first list 2570 for selecting the protocol corresponding to the first region 2520 on the left, and the first list 2560 for selecting the protocol corresponding to the first region 820 on the right.

Referring to FIG. 25B, a T1W protocol is selected as denoted by a reference numeral 2571 correspondingly to the first region 2520 on the left, and a T2W protocol is selected as denoted by a reference numeral 2561 correspondingly to the first region 820 on the right.

Figure 26:
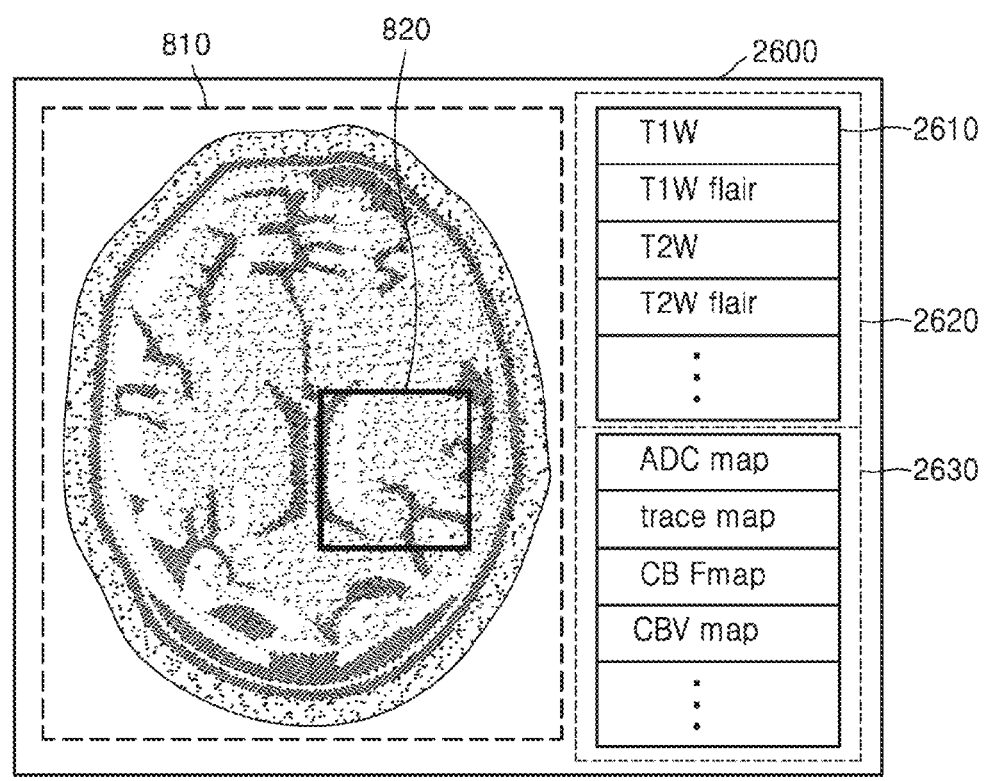
FIG. 26 is a diagram for describing operations of a medical image providing apparatus, according to another exemplary embodiment.

FIG. 26 is a diagram for describing operations of the medical image providing apparatus 600, according to another exemplary embodiment.

Referring to FIG. 26, a screen 2600 displayed on the display unit 620 may include the first image 810 and a first list 2610. In detail, when the first region 820 is selected, the medical image providing apparatus 600 may output the first list 2610. Here, the first list 2610 may include at least one of anatomical image items corresponding to protocols and functional image items corresponding to protocols.

Images corresponding to protocols described above may be classified into anatomical images and functional images.

Referring to FIG. 26, the first list 2610 may include anatomical image items 2620 and functional image items 2630.

As shown in FIG. 26, the anatomical image items 2620 may include a T1-weighted image (T1W), a T1 flair image (T1W flair), a T2-weighted image (T2W), and a T2 flair image (T2W flair). The functional image items 2630 may include an ADC map, a trace map, a CBF map, and a CBV map. Here, the anatomical image items 2620 and the functional image items 2630 may be separated and listed as shown in FIG. 26. Various anatomical image items and various functional image items other than those shown in FIG. 26 may be further included.

Figure 27A:
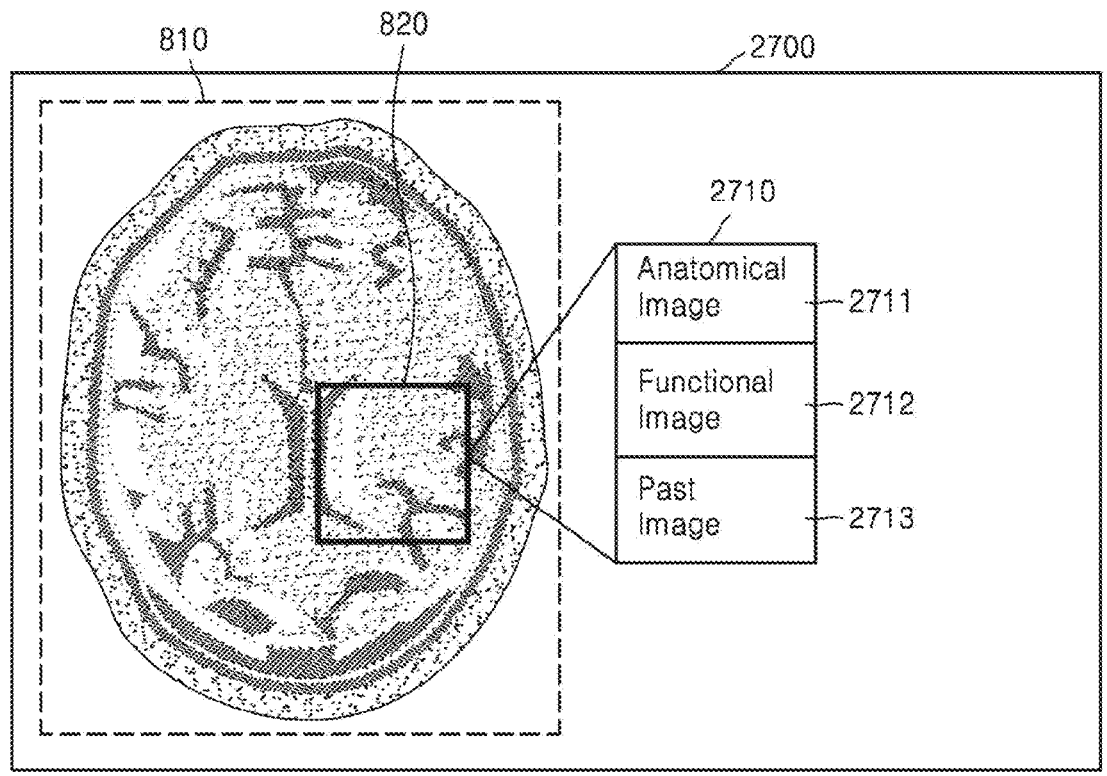
FIGS. 27A and 27B show diagrams for describing operations of a medical image providing apparatus, according to another exemplary embodiment.
Figure 27B:
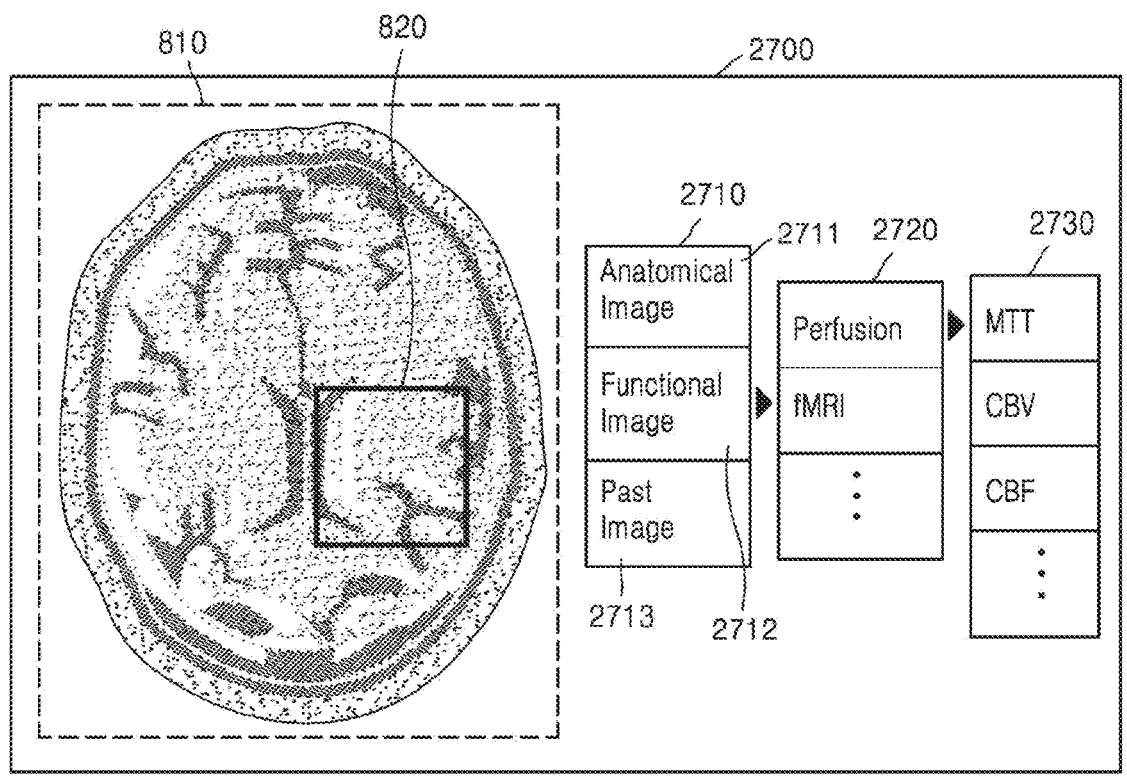

FIGS. 27A and 27B show diagrams for describing operations of the medical image providing apparatus 600, according to another exemplary embodiment.

Referring to FIG. 27A, a screen 2700 displayed on the display unit 620 may include the first image 810 and a first list 2710. Here, the first list 2710 may separately display an anatomical image and a functional image.

In detail, when the first region 820 is selected, the medical image providing apparatus 600 may output the first list 2710. The first list 2710 includes an anatomical image item 2711 corresponding to a protocol, and a functional image item 2712 corresponding to a protocol. The first list 2710 may further include a past medical image item 2713 of the same patient.

In order to receive a selection on an anatomical image and a functional image, the UI unit 630 may output a menu list in stages. For example, when the user selects the functional image item 2712 from the first list 2710, the UI unit 630 outputs a first sub-list 2720 including items of protocols corresponding to the functional image item 2712. Continuously when the user selects a predetermined protocol, for example, a perfusion protocol, from the first sub-list 2720, the UI unit 630 outputs a second sub-list 2730 including functional image items corresponding to the selected predetermined protocol. Referring to FIG. 27B, examples of a functional image obtained by using image data obtained by applying a perfusion protocol include an MTT image, a CBV image, and a CBF image.

FIGS. 28A, 28B, and 28C show diagrams for describing operations of the medical image providing apparatus 600, according to another exemplary embodiment.

Referring to FIG. 28A, a screen 2800, in which a predetermined protocol or a predetermined image item is selected from a first list and a second image corresponding to the selected predetermined protocol is overlaid on a first region 2810, is illustrated. It is assumed that a T2-weighted image is overlaid on the first region 2810 in FIG. 28A.

The second image overlaid on the first region 2810 may be expanded or reduced. In detail, the control unit 610 may control the second image to be expanded or reduced in response to a user's request input through the UI unit 630. Here, a partial image that is overlaid may be simply expanded or reduced. Alternatively, a size of the first region 2810 may be expanded or reduced such that a range of an object included on the first region 2810 is expanded or reduced.

Referring to FIG. 28B, when the size of the first region 2810 is expanded or reduced by using an input device included in the UI unit 630, a size of the second image is also expanded or reduced according to the first region 2810 to be overlaid on the first region 2810.

In detail, as shown in FIG. 28B, the range of the object included in a second image 2860 may be expanded. Accordingly, a screen 2850 of FIG. 28B may be displayed to the user.

Referring to FIG. 28C, an image obtained by expanding or reducing the second image overlaid on the first region 2810 may be displayed.

In detail, as shown in FIG. 28C, a second image 2890 obtained by expanding a second image that was overlaid on the first region 2810 may be displayed. Accordingly, a screen 2880 of FIG. 28C may be displayed to the user.

FIG. 29 is a diagram for describing operations of the medical image providing apparatus 600, according to another exemplary embodiment.

The control unit 610 may switch and display a first region 2910 and a first image 2900, according to a user's request input through the UI unit 630. In detail, an image type of an image displayed in the first region 2910 and an image type of the first image 2900 displayed throughout a screen may be mutually switched.

Referring to FIG. 29, a T2W protocol is selected from a first list, and a T2-weighted image may be overlaid and displayed on the first region 2910. In FIG. 29, the first image 2900 is an MRI scout image.

Referring to FIG. 29, when the user requests the image types of the first region 2910 and first image 2900 to be switched through the UI unit 630, a first image 2950 that is a whole image is switched from an MRI scout image to a T2-weighted image, and a first image 2960 that is a partial image is switched from a T2-weighted image to an MRI scout image.

In detail, in order to change an image type, the UI unit 630 may output a menu including an 'image type changing key' (not shown). Alternatively, an image type may be changed when the user touches or clicks the first image 2900 a predetermined number of times.

Figure 30A:
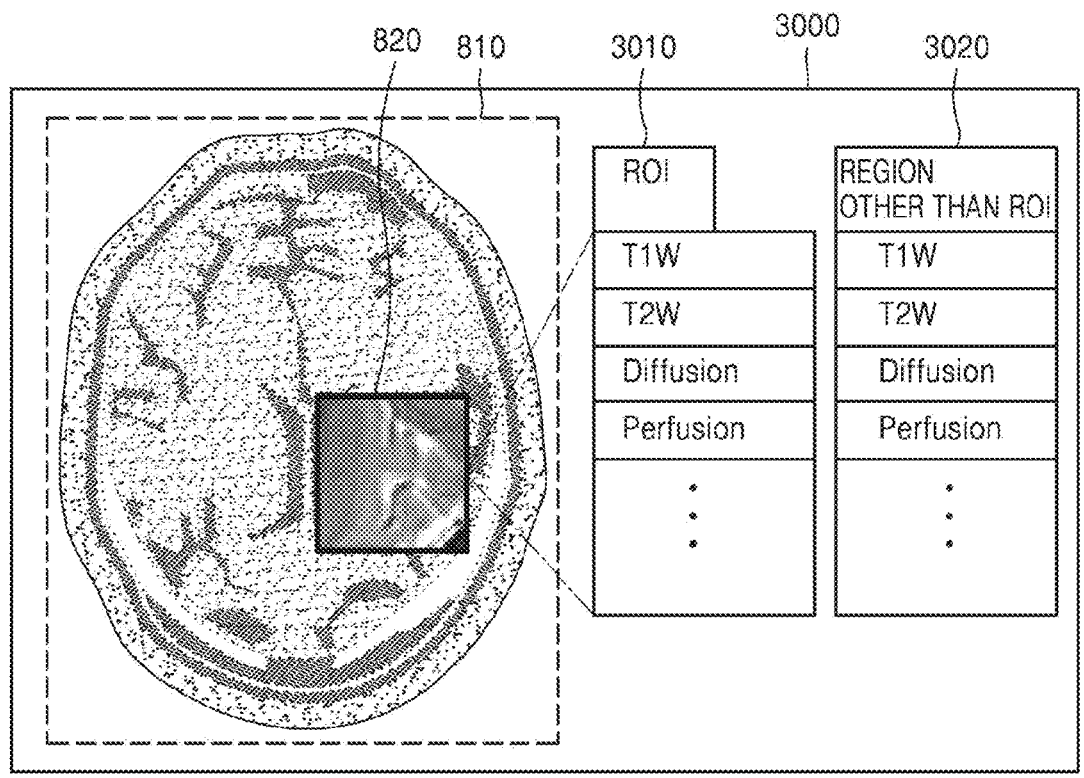
FIGS. 30A and 30B show diagrams for describing operations of a medical image providing apparatus, according to another exemplary embodiment.
Figure 30B:
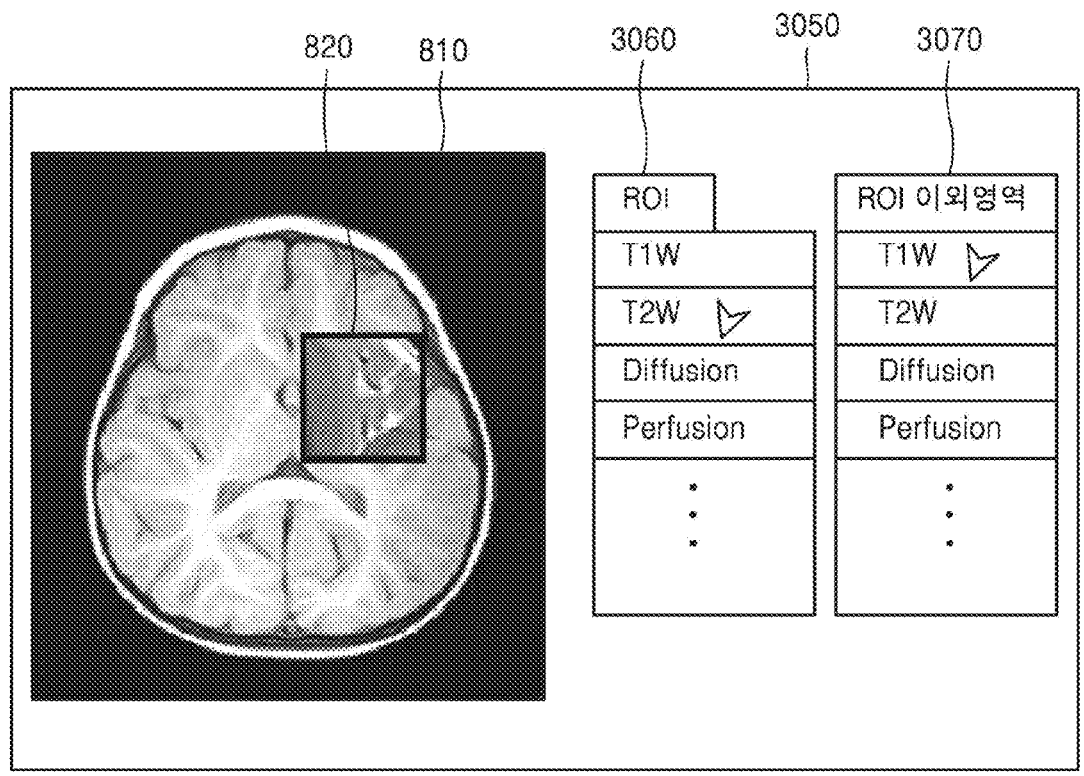

FIGS. 30A and 30B show diagrams for describing operations of the medical image providing apparatus 600, according to another exemplary embodiment.

Referring to FIG. 30A, a screen 3000 displayed on the display unit 620 may include the first image 810, a first list 3010, and a second list 3020. Here, the first list 3010 is used to select a protocol of an image to be displayed on the first region 820. The second list 3020 is used to select a protocol of an image to be displayed on the first image 810 but not on the first region 820.

In other words, when the first region 820 is set as an ROI, protocols corresponding to the inside and outside of the ROI may be individually set.

Referring to FIG. 30B, a protocol of an image to be overlaid on the first region 820 is selected to be a T2W protocol from a first list 3060, and a protocol of the first image 810 but not on the first region 820 is selected to be a T1W protocol from a second list 3070. Accordingly, a T2-weighted image is displayed on the first region 820 and a T1-weighted image is displayed on the first image 810 but not on the first region 820.

Figure 31A:
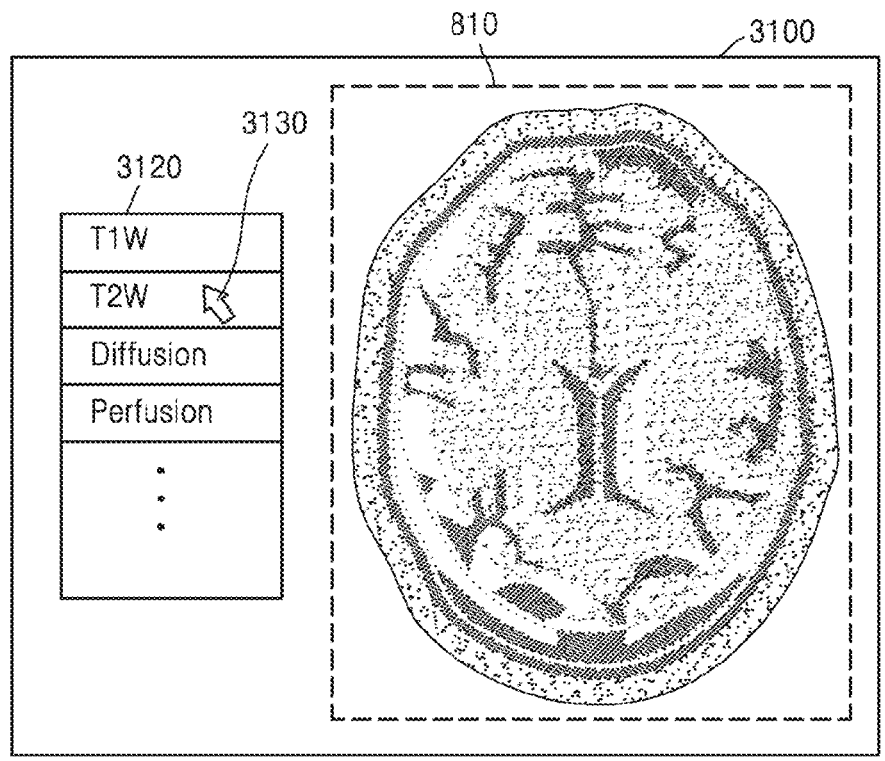
FIGS. 31A and 31B show diagrams for describing operations of a medical image providing apparatus, according to another exemplary embodiment.
Figure 31B:
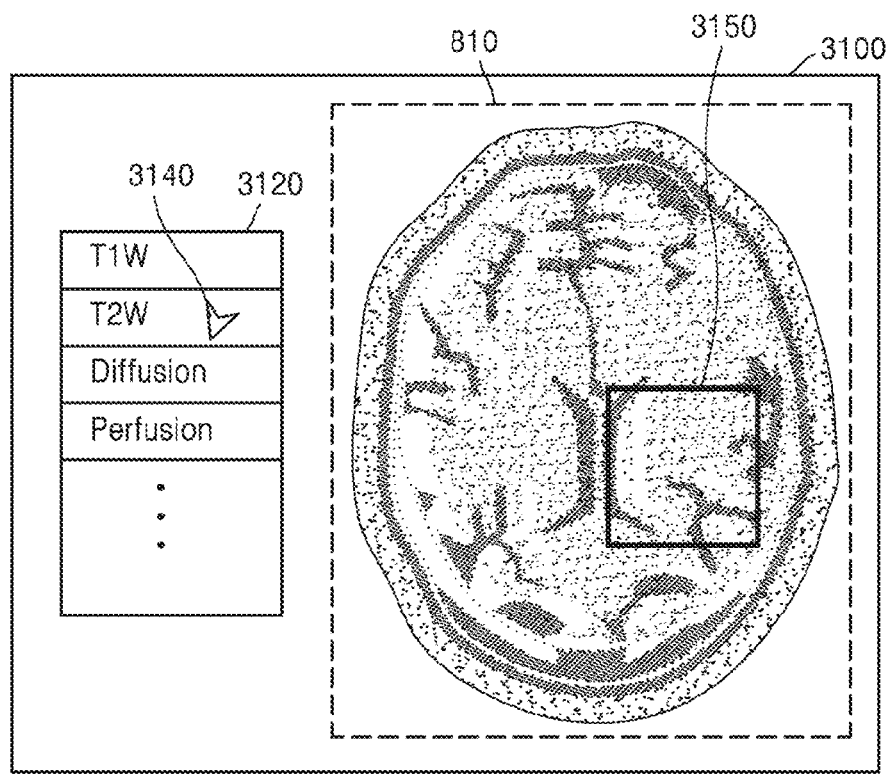

FIGS. 31A and 31B show diagrams for describing operations of the medical image providing apparatus 600, according to another exemplary embodiment.

Here, in the control unit 610, a protocol may be first selected before a first region is selected, and then the first region may be set after the protocol is selected.

Referring to FIG. 31A, the display unit 620 may display a screen 3100 including a first list 3120. The user may select a predetermined item included in the first list 3120 by using a cursor 3130. Here, the first list 3120 may have any one of various shapes shown in FIGS. 9 through 30, as well as a shape shown in FIGS. 31A and 31B. For example, the first list 3120 may include at least one of a plurality of anatomical image items corresponding to a protocol and a plurality of functional image items corresponding to a protocol.

Referring to FIG. 31B, when the user selects a predetermined item, for example, a T2W protocol item, through the UI unit 630 as denoted by a reference numeral 3140, the control unit 610 may then set a first region 3150.

Here, the first region 3150 may be set through the UI unit 630, or may be automatically set by the control unit 610.

In detail, the UI unit 630 may receive a setting on an ROI on the first image 810 included in the screen 3100 from the user. Then, the control unit 610 may set the ROI as the first region 3150. Then, a reconstructed image corresponding to the selected protocol may be overlaid and displayed on the first region 3150.

Alternatively, when a predetermined protocol is selected from the first list 3120, the control unit 610 may extract a region capable of most satisfactorily expressing an image corresponding to the selected predetermined protocol, as the first region 3150. For example, when a CBF map of a perfusion protocol is selected from the first list 3120, the CBF map most satisfactorily shows blood flow. Accordingly, the control unit 610 may set a region including blood vessels where blood mostly flows, as the first region 3150.

Figure 32:
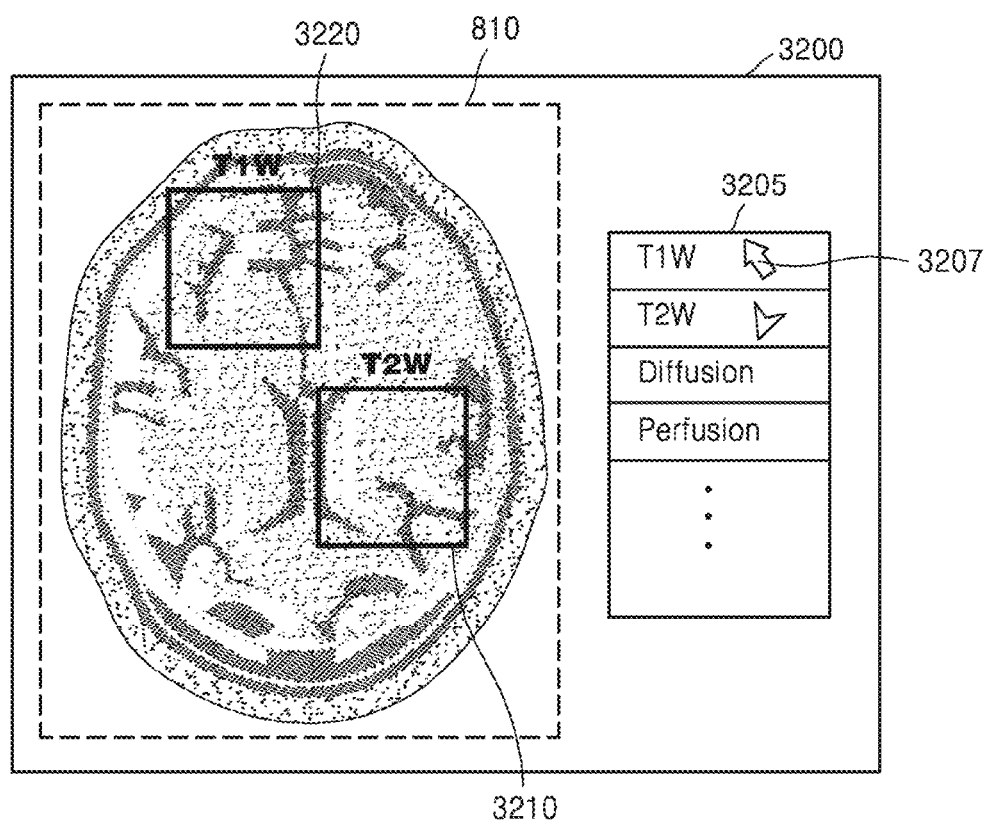
FIG. 32 is a diagram for describing operations of a medical image providing apparatus, according to another exemplary embodiment.

FIG. 32 is a diagram for describing operations of the medical image providing apparatus 600, according to another exemplary embodiment.

In the control unit 610, a protocol may be first selected before a first region is selected, and while setting the first region after the protocol is selected, a plurality of protocols may be selected and then a plurality of first regions corresponding to the selected plurality of protocols may be set. In detail, the user may manipulate an input device of the UI unit 630 to move a location of a cursor 3207 so as to select a plurality of protocols from list 3205.

In detail, referring to FIG. 32, a screen 3200 showing that a T2W protocol is selected first, and then a first region 3210 corresponding to the T2W protocol is set. Then, a T1W protocol is selected, and a first region 3220 corresponding to the T1W protocol is set.

Figure 33:
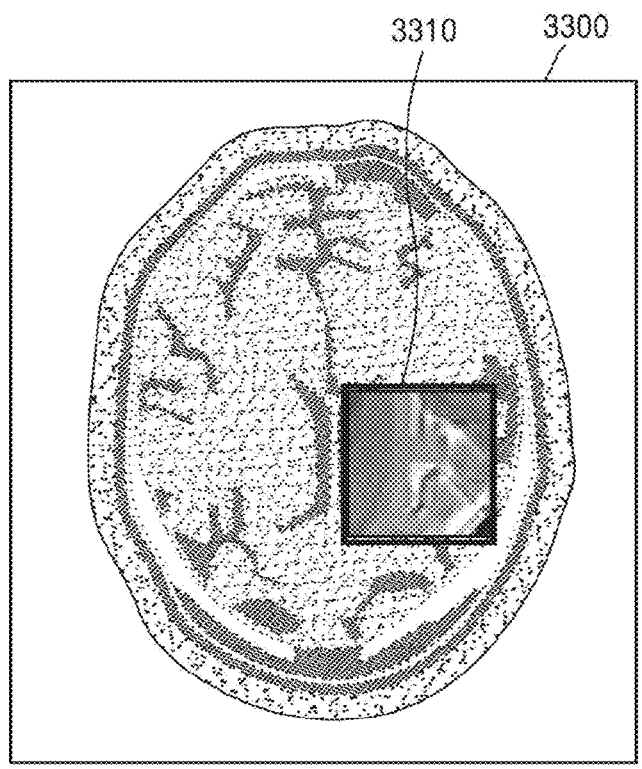
FIG. 33 is a diagram for describing operations of a medical image providing apparatus, according to another exemplary embodiment.

FIG. 33 is a diagram for describing operations of the medical image providing apparatus 600, according to another exemplary embodiment.

FIG. 33 illustrates a screen including a first image 3300 displayed on the display unit 620.

The UI unit 630 may receive a selection on at least one first region 3310 from the first image 3300 including an object. In FIG. 33, one region, i.e., the first region 3310, is selected, but alternatively, a plurality of partial regions may be selected.

The control unit 610 may display a second image reconstructed by using at least one piece of image data obtained by scanning the object by applying at least one protocol, on the first region 3310 of the first image 3300.

In detail, the control unit 610 may obtain image data corresponding to a predetermined protocol and reconstruct a second image by using the obtained image data, based on a region of the object included in the first region 3310.

In detail, the control unit 610 may analyze an image included in the first region 3310 to determine whether the region of the object included in the first region 3310 has a disease or disorder. When there is a disease or disorder, a reconstructed image may be generated according to protocols so as to further accurately read the disease or disorder.

In detail, when it is determined that there is a tumor by analyzing an image included in the first region 3310, the control unit 610 may reconstruct a T2-weighted image for accurately reading the tumor.

Alternatively, for example, when it is determined that blood vessels in an image included in the first region 3310 are abnormal after analyzing the image, for example, when hemadostenosis is found, the control unit 610 may generate a CBV map or CBF map corresponding to a perfusion protocol so as to further accurately read the blood vessels or blood flow. The generated CBV map or CBF map may be overlaid and displayed on the first region 3310.

The control unit 610 may select at least one piece of image data from among a plurality of pieces of image data obtained by scanning an object by applying at least one protocol, and generate a second image by using the selected at least one piece of image data, based on a region of the object included in the first region 3310.

In detail, the memory 640 may include at least one piece of image data corresponding to at least one protocol. Here, when it is determined that there is a disease or disorder after analyzing an image of the region of the object included in the first region 3310, the control unit 610 may read image data for accurately reading the disease or disorder from the memory 640 and reconstruct a second image.

Alternatively, the memory 640 may store at least one reconstructed image reconstructed by using at least one piece of image data corresponding to at least one protocol. Here, when it is determined that there is a disease or disorder after analyzing the partial image indicating the region of the object included in the first region 3310, the control unit 610 may read a reconstructed image for accurately reading the disease or disorder from the memory 640, and overlay and display the reconstructed image on the first region 3310.

In FIG. 33, when it is determined that an anatomical structure of the region of the object included in the first region 3310 is unusual, the control unit 610 may obtain a T1-weighted image for further accurately reading the anatomical structure, and overlay and display the T1-weighted image on the first region 3310.

Figure 34A:
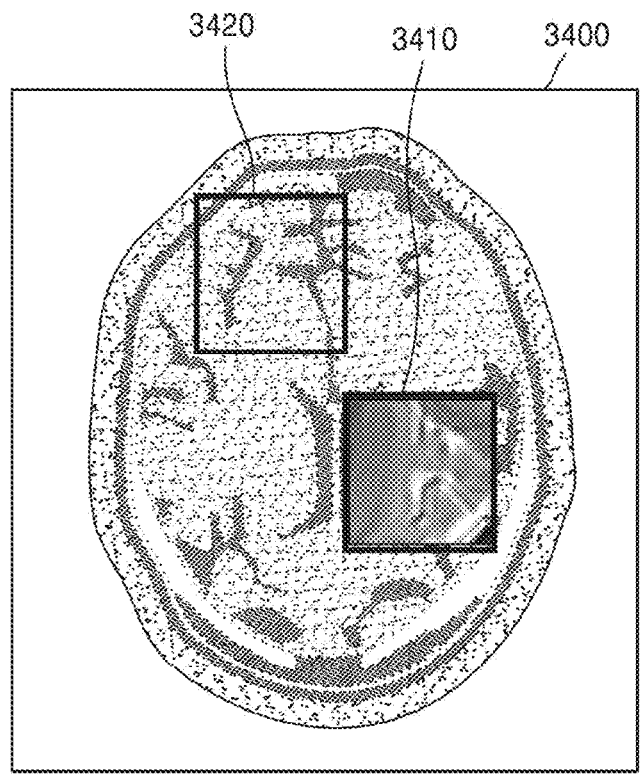
FIGS. 34A and 34B show diagrams for describing operations of a medical image providing apparatus, according to another exemplary embodiment.
Figure 34B:
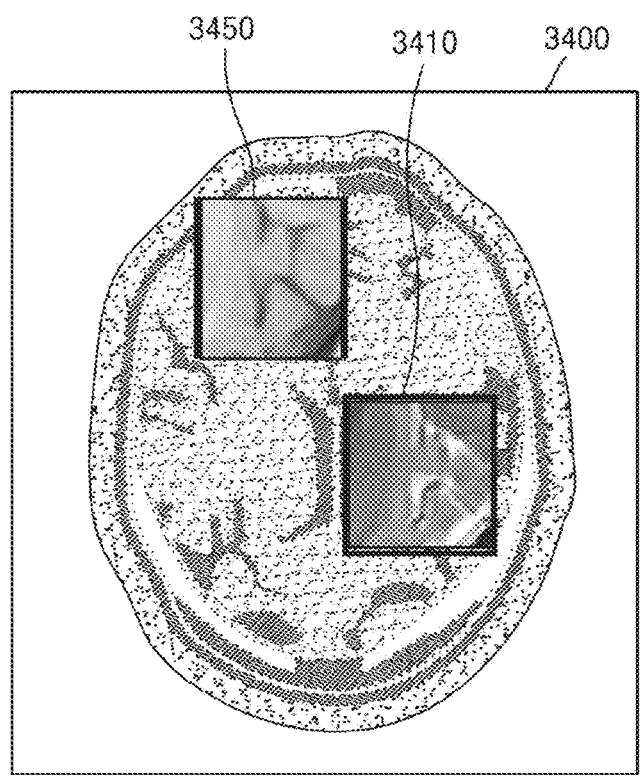

FIGS. 34A and 34B show diagrams for describing operations of the medical image providing apparatus 600, according to another exemplary embodiment.

Here, in the control unit 610, when the user requests to change a location of a first region after a second image corresponding to a selected protocol is overlaid and displayed on the first region of a first image, a type of an image overlaid on the first region having the changed location may be changed.

In detail, referring to FIG. 34A, after the second image corresponding to the selected protocol is overlaid and displayed on a first region 3410 in a first image 3400, the user may request a location of the first region 3410 to be changed to a first region 3420 through the UI unit 630.

Then, the control unit 610 may automatically output a first list according to the changed location of the first region 3410, and receive a selection on a new protocol.

According to the changed location of the first region 3410, the control unit 610 may re-select a predetermined protocol, obtain image data corresponding to the re-selected predetermined protocol, and reconstruct a second image by using the obtained image data, based on a region of an object included in the first region 3420. Next, the control unit 610 may overlay and display an image corresponding to the re-selected protocol on the first region 3420.

Referring to FIG. 34B, an image 3450 corresponding to the re-selected protocol may be overlaid and displayed on the first region 3410 having the changed location, i.e., the first region 3420.

Figure 35A:
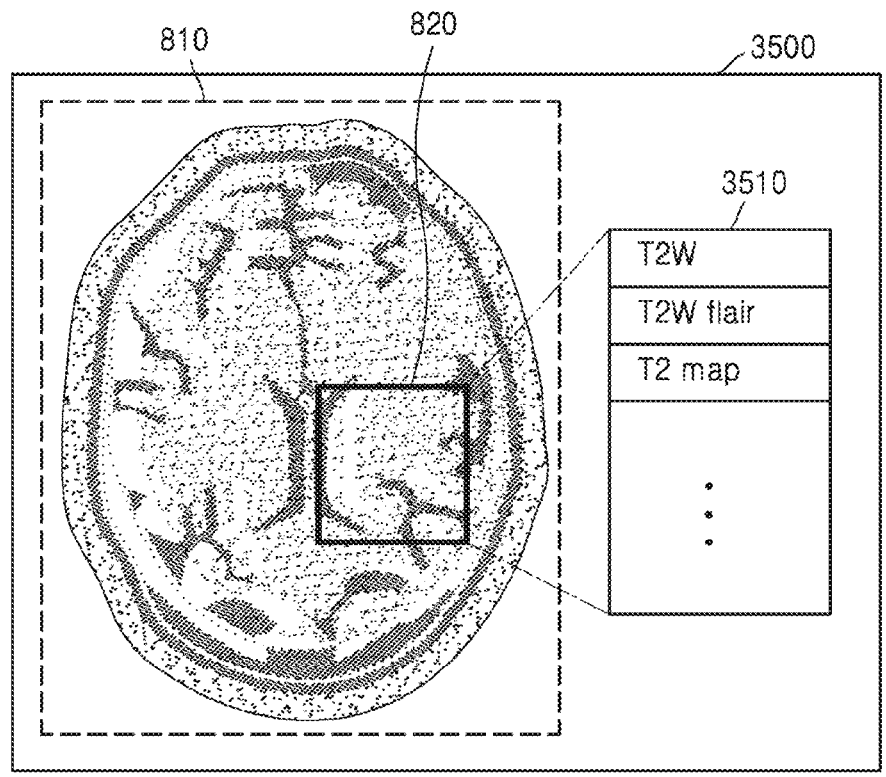
FIGS. 35A and 35B show diagrams for describing operations of a medical image providing apparatus, according to another exemplary embodiment.
Figure 35B:
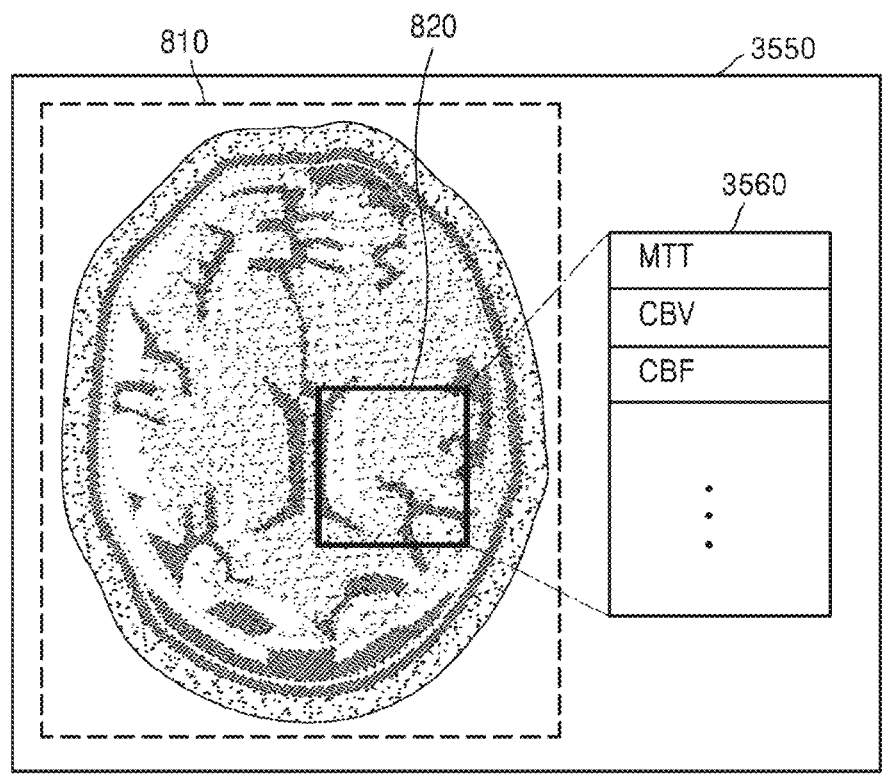

FIGS. 35A and 35B show diagrams for describing operations of the medical image providing apparatus 600, according to another exemplary embodiment.

The display unit 620 may display a first image including an object.

Then, when a first region is selected from the first image, the UI unit 630 may output a first list including at least one image item obtained by using the first image, and receive a selection on a predetermined item from the first list.

The control unit 610 may control a second image corresponding to the predetermined item selected through the UI unit 630 to be overlaid and displayed on the first region.

Referring to FIG. 35A, a screen 3500 displayed on the display unit 620 includes the first image 810 and a first list 3510.

Referring to FIG. 35A, when the first region 820 is selected, the medical image providing apparatus 600 may automatically output the first list 3510.

Here, the first list 3510 includes image items obtained by using the first image 810. In detail, when the first image 810 is an image reconstructed by using image data obtained by applying a predetermined protocol, an image that is reconstructed, calculated, or post-processed by using the image data may be included in the first list 3510.

For example, when the first image 810 is a T2-weighted image obtained by applying a T2W protocol, a T2 flair image or a T2 map may be obtained via a post-process or a separate calculation using image data obtained by applying the T2W protocol. Accordingly, as described above, the first list 3510 may include a T2W item, a T2 flair item, and a T2 map item.

Alternatively, referring to FIG. 35B, when the first image 810 is a perfusion image obtained by applying a perfusion protocol, an MTT map, a CBF map, or a CBV map may be obtained via a post-process or separate calculation using image data obtained by applying the perfusion protocol. Accordingly, a first list 3560 displayed on a screen 3550 may include an MTT map item, a CBF map item, and a CBV map item.

Figure 36:
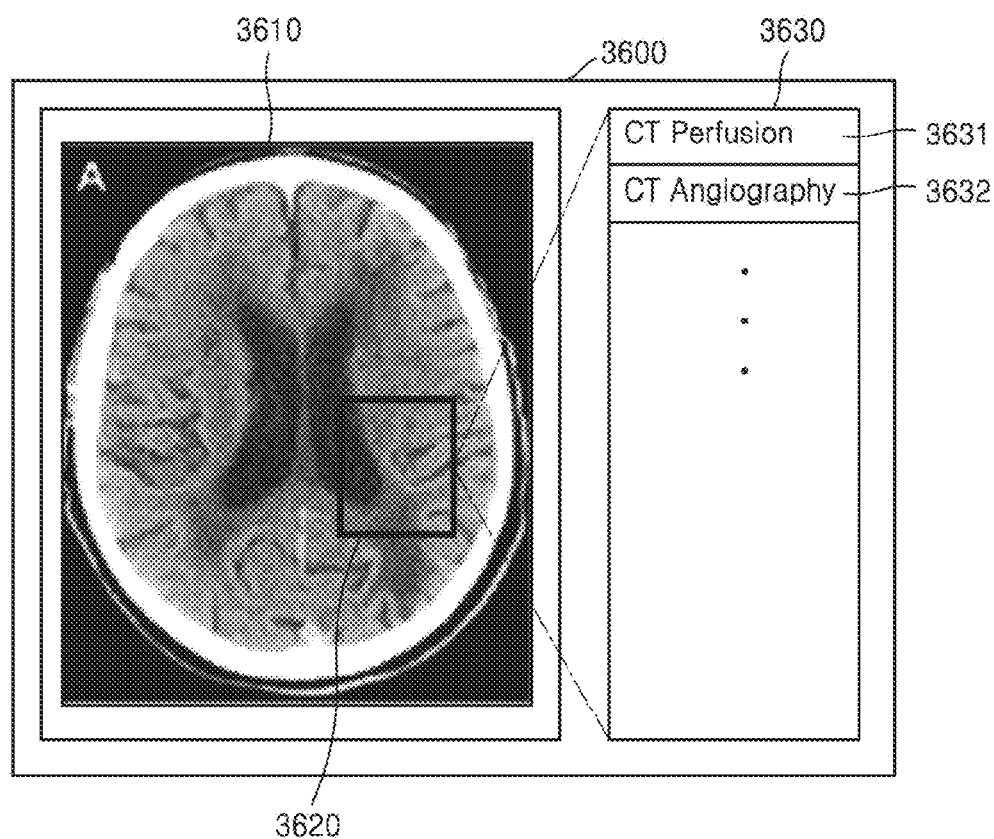
FIG. 36 shows a diagram for describing operations of a medical image providing apparatus, according to another exemplary embodiment.

FIG. 36 shows a diagram for describing operations of the medical image providing apparatus 600, according to another exemplary embodiment.

FIG. 36 illustrates a screen 3600 output by the display unit 620. In FIG. 36, a first image 3610 included in the screen 3600 is a CT image, and a first list 3630 includes CT protocols. For example, the first list 3630 may include protocols applied to CT scan, such as a CT perfusion protocol 3631 and a CT angiography protocol 3632 indicating a 'DSA protocol'. Also, when the CT perfusion protocol 3631 is selected from the first list 3630, the control unit 610 may control an image obtained according to a perfusion protocol to be overlaid and displayed on a first region 3620.

Figure 37:
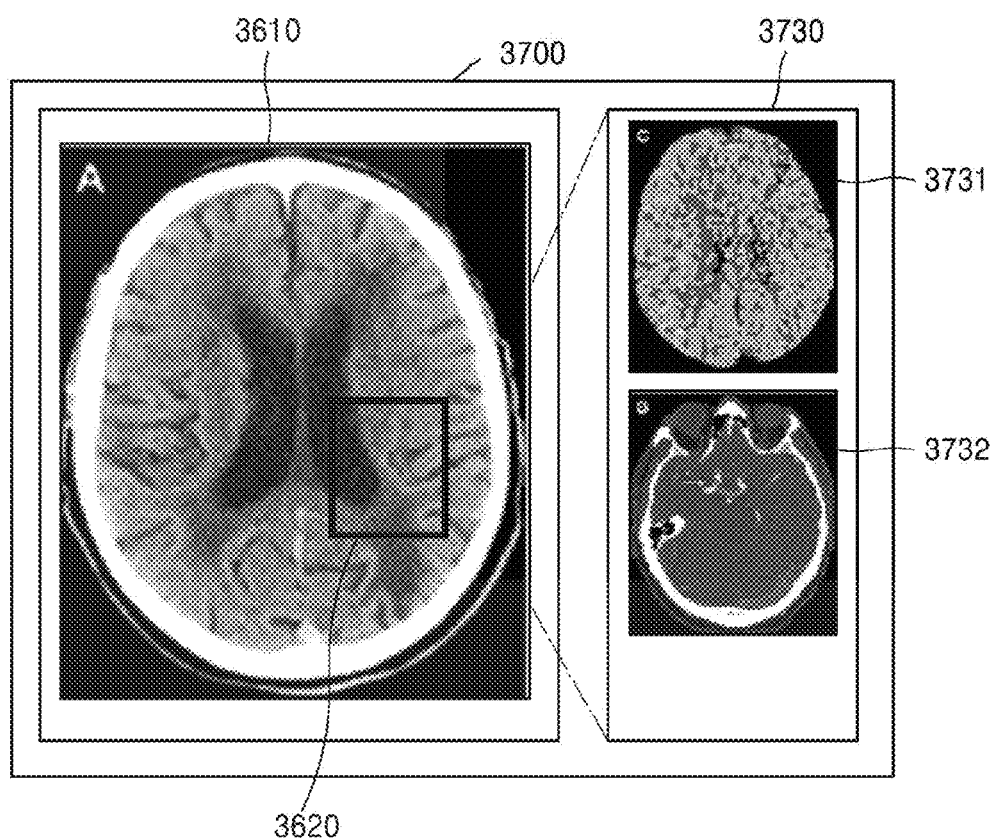
FIG. 37 shows a diagram for describing operations of a medical image providing apparatus, according to another exemplary embodiment.

FIG. 37 shows a diagram for describing operations of the medical image providing apparatus 600, according to another exemplary embodiment.

FIG. 37 illustrates a screen 3700 output by the display unit 620. Since the screen 3700 of FIG. 37 is the same as the screen 3600 of FIG. 36 except for a second list 3730 including at least one image obtained based on image data obtained by applying at least one protocol, descriptions thereof that are the same as those of the screen 3600 of FIG. 36 are not provided here.

Referring to FIG. 37, the second list 3730 includes at least one image obtained based on image data obtained by applying CT protocols. The at least one image included in the second list 3730 may be an image of an object or a partial image indicating a region of the object. In FIG. 37, the second list 3730 includes the image of the object.

In detail, the second list 3730 includes a perfusion image 3731 obtained by applying a CT perfusion protocol, and a CT angiography image 3732 obtained by applying a CT angiography protocol indicating a 'DSA protocol'. When the perfusion image 3731 is selected from the second list 3730, the control unit 610 may control a partial image included in the perfusion image 3731 to be overlaid and displayed on the first region 3620.

Figure 38:
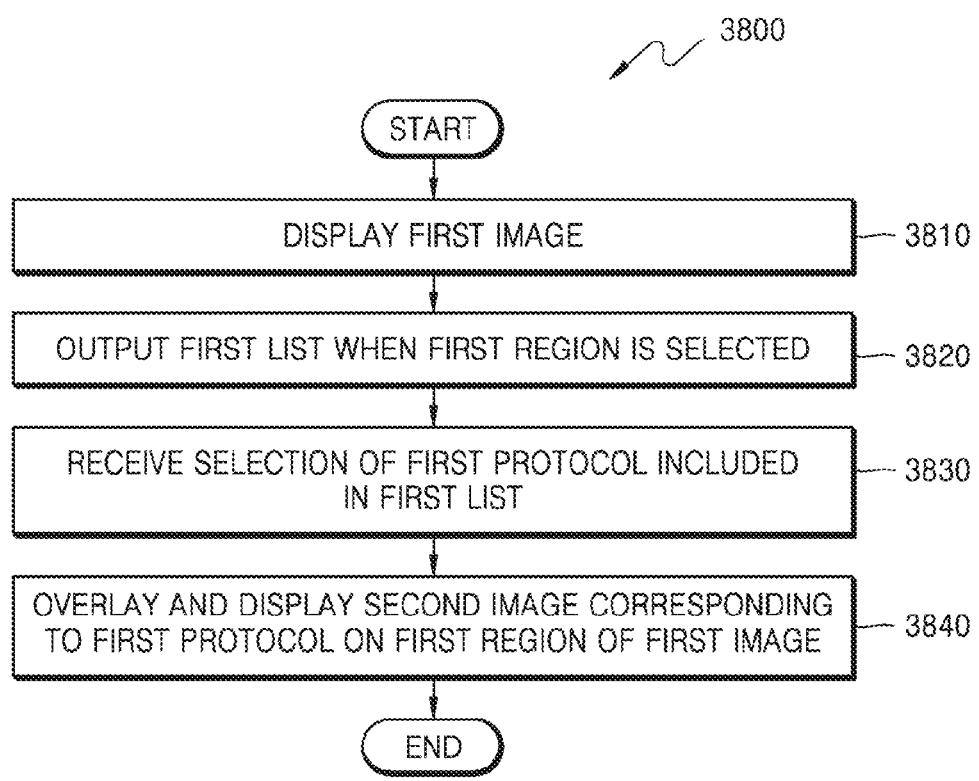
FIG. 38 is a flowchart of a medical image processing method according to an exemplary embodiment.

FIG. 38 is a flowchart of a medical image processing method 3800 according to an exemplary embodiment. The medical image processing method 3800 according to an exemplary embodiment may be performed by the medical image providing apparatus 500 or 600 described above with reference to FIGS. 1 through 37. Also, since operations of the medical image processing method 3800 include the same features as operations of the medical image providing apparatus 500 or 600, descriptions thereof that are the same as those of FIGS. 1 through 37 are not provided again. Hereinafter, a medical imaging processing method according to one or more exemplary embodiments will be described by referring to the medical image providing apparatus 600 of FIG. 6.

According to the medical image processing method 3800, a first image including an object is displayed in operation 3810. Operation 3810 may be performed by the display unit 620 under control of the control unit 610.

When a first region included in the first image is selected, a first list including at least one protocol applied while scanning the object is output in operation 3820. Operation 3820 may be performed by the UI unit 630 under control of the control unit 610.

A selection of a first protocol included in the first list is received through a UI in operation 3830. Operation 3830 may be performed by the UI unit 630 under control of the control unit 610.

A second image reconstructed by using image data obtained by applying the first protocol selected in operation 3830 is overlaid and displayed on the first region of the first image in operation 3840. Operation 3840 may be performed by the display unit 620 under control of the control unit 610. In detail, the second image is an image corresponding to a region of the object included in the first region.

Figure 39:
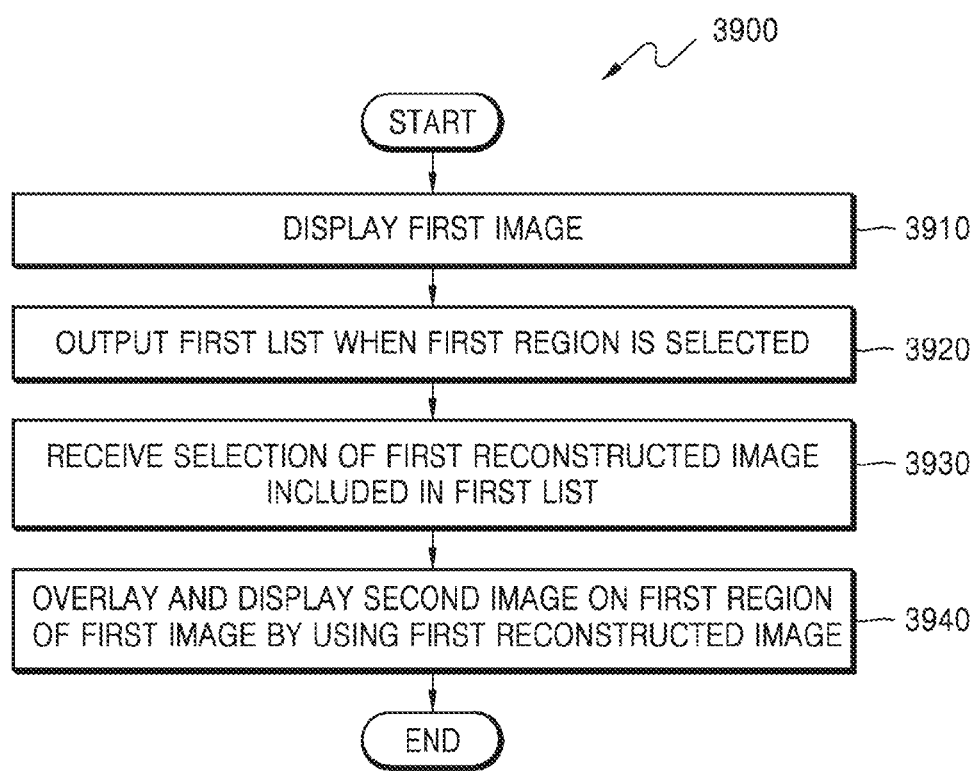
FIG. 39 is a flowchart of a medical image processing method according to another exemplary embodiment.

FIG. 39 is a flowchart of a medical image processing method 3900 according to another exemplary embodiment. The medical image processing method 3900 according to an exemplary embodiment may be performed by the medical image providing apparatus 500 or 600 described above with reference to FIGS. 1 through 37. Also, since operations of the medical image processing method 3900 include the same features as operations of the medical image providing apparatus 500 or 600, descriptions thereof that are the same as those of FIGS. 1 through 37 are not provided again.

According to the medical image processing method 3900, a first image including an object is displayed in operation 3910. Operation 3910 may be performed by the display unit 620 under control of the control unit 610.

When a first region included in the first image is selected, a first list including at least one reconstructed image that is reconstructed by using at least one piece of image data obtained by applying at least one protocol applied while scanning the object is output in operation 3920. Operation 3920 may be performed by the UI unit 630 under control of the control unit 610.

A selection of a first reconstructed image included in the first list is received through a UI, in operation 3930. Operation 3930 may be performed by the UI unit 630 under control of the control unit 610.

In operation 3940, a second image is overlaid and displayed on the first region of the first image by using the first reconstructed image selected in operation 3930. Operation 3940 may be performed by the display unit 620 under control of the control unit 610. In detail, a partial image of the first reconstructed image, which corresponds to the first region, is overlaid and displayed on the first region of the first image.

Figure 40:
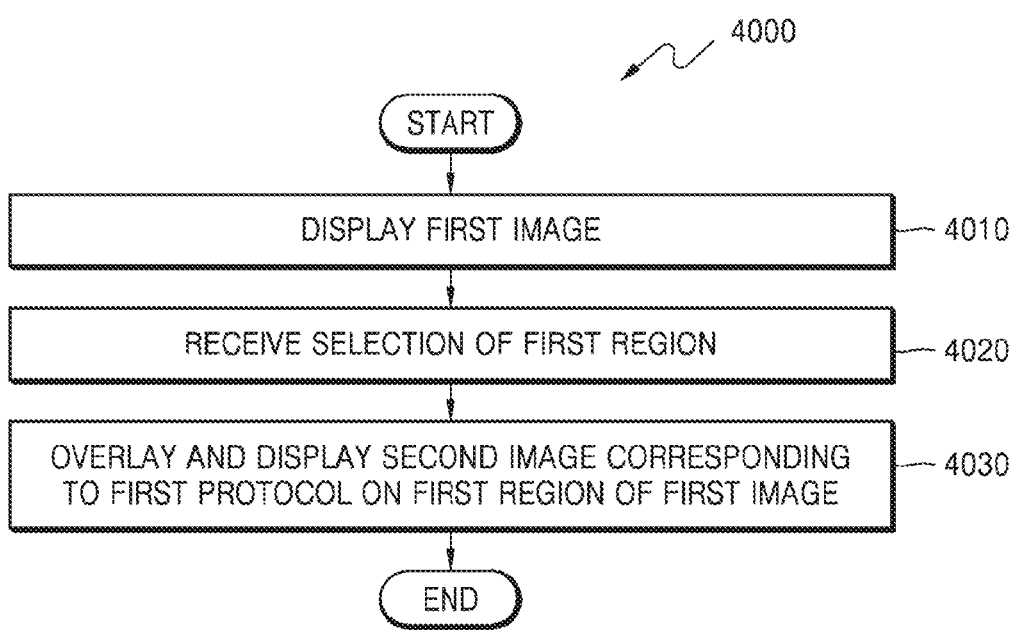
FIG. 40 is a flowchart of a medical image processing method according to another exemplary embodiment.

FIG. 40 is a flowchart of a medical image processing method 4000 according to another exemplary embodiment. The medical image processing method 4000 according to an exemplary embodiment may be performed by the medical image providing apparatus 500 or 600 described above with reference to FIGS. 1 through 37. Also, since operations of the medical image processing method 4000 include the same features as operations of the medical image providing apparatus 500 or 600, descriptions thereof that are the same as those of FIGS. 1 through 37 are not provided again.

According to the medical image processing method 4000, a first image including an object is displayed in operation 4010. Operation 4010 may be performed by the display unit 620 under control of the control unit 610.

A selection of a first region of the first image is received through a UI in operation 4020. Operation 4020 may be performed by the UI unit 630 under control of the control unit 610.

A second image reconstructed by using first image data obtained by scanning the object by applying a first protocol is overlaid and displayed on the first region of the first image in operation 4030. Operation 4030 may be performed by the display unit 620 under control of the control unit 610.

Figure 41:
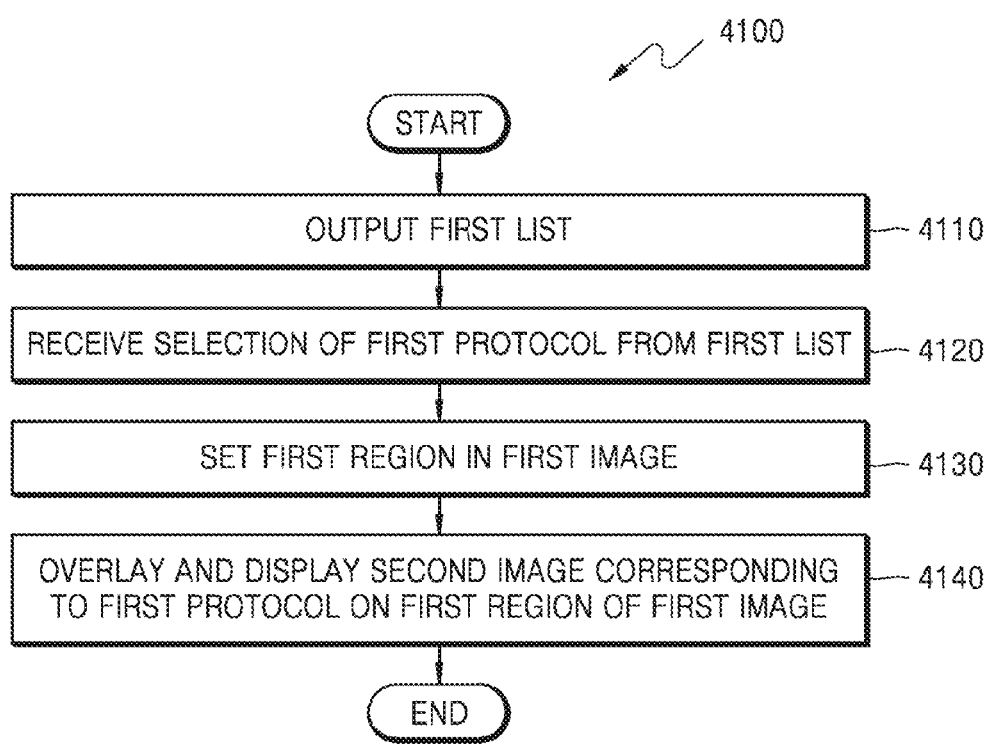
FIG. 41 is a flowchart of a medical image processing method according to another exemplary embodiment.

FIG. 41 is a flowchart of a medical image processing method 4100 according to another exemplary embodiment. The medical image processing method 4100 according to an exemplary embodiment may be performed by the medical image providing apparatus 500 or 600 described above with reference to FIGS. 1 through 37. Also, since operations of the medical image processing method 4100 include the same features as operations of the medical image providing apparatus 500 or 600, descriptions thereof that are the same as those of the medical image providing apparatus 500 or 600 of FIGS. 1 through 37 are not provided again.

A screen including a first list including at least one protocol applied while scanning an object is displayed in operation 4110. Operation 4110 may be performed by the display unit 620 under control of the control unit 610.

A selection of a first protocol from the first list is received through a UI in operation 4120. Operation 4120 may be performed by the UI unit 630 under control of the control unit 610.

Then, a first region is set in the first image including the object in operation 4130. Operation 4130 may be performed by the control unit 610. Alternatively, when the first region is set based on a user input, operation 4130 may be performed by the UI unit 630 under control of the control unit 610.

A second image reconstructed by using image data obtained by applying the first protocol is overlaid and displayed on the first region in operation 4140. Operation 4140 may be performed by the display unit 620 under control of the control unit 610.

Figure 42:
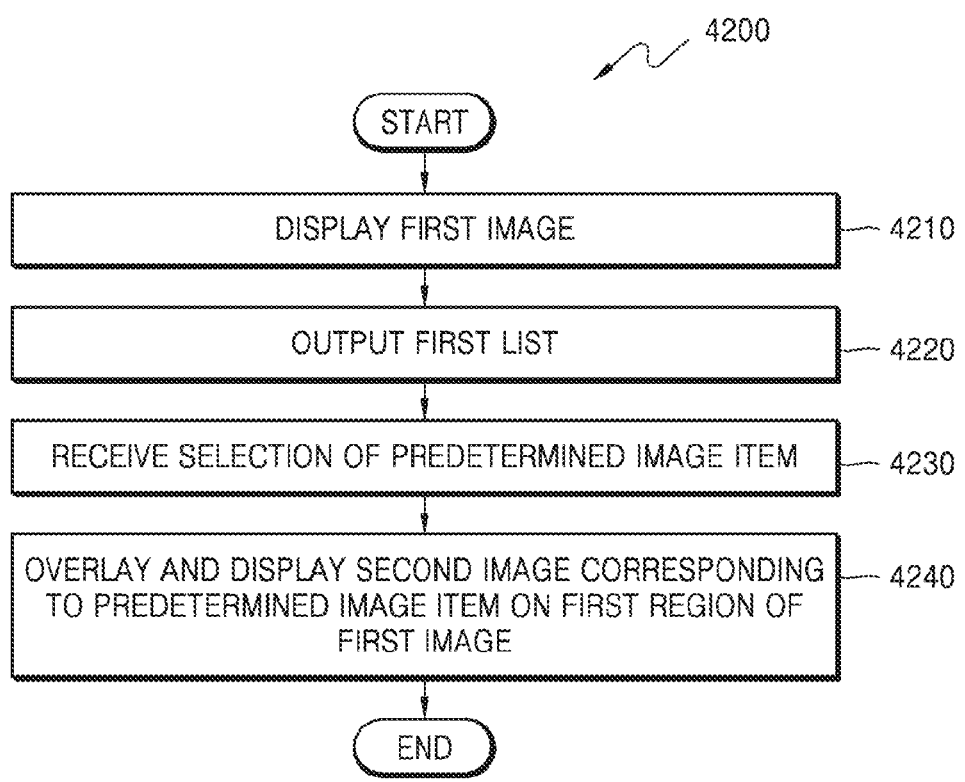
FIG. 42 is a flowchart of a medical image processing method according to another exemplary embodiment.

FIG. 42 is a flowchart of a medical image processing method 4200 according to another exemplary embodiment. The medical image processing method 4200 according to an exemplary embodiment may be performed by the medical image providing apparatus 500 or 600 described above with reference to FIGS. 1 through 37. Also, since operations of the medical image processing method 4200 include the same features as operations of the medical image providing apparatus 500 or 600, descriptions thereof that are the same as those of the medical image providing apparatus 500 or 600 of FIGS. 1 through 37 are not provided again.

According to the medical image processing method 4200, a first image including an object is displayed in operation 4210. Operation 4210 may be performed by the display unit 620 under control of the control unit 610.

A selection of a predetermined item included in the first list is received through a UI in operation 4220. Operation 4220 may be performed by the UI unit 630 under control of the control unit 610.

A selection of a first region from the first image is received through a UI in operation 4230. Operation 4220 may be performed by the UI unit 630 under control of the control unit 610.

A second image corresponding to the predetermined item selected in operation 4220 is overlaid and displayed on the first region in operation 4240. Operation 4240 may be performed by the display unit 620 under control of the control unit 610.

As described above, according to the one or more of the above exemplary embodiments, a medical image providing apparatus and a medical image processing method of the same may provide a UI screen for a user, such as a doctor, to easily read a medical image of a patient.

The medical image providing apparatus and the medical image processing method of the same may enable the user to further accurately read a predetermined region of an object by using at least one medical image reconstructed by scanning the object by applying at least one protocol.

Accordingly, the user may further easily diagnose a disease and read the medical image.

The exemplary embodiments can be written as computer programs and can be implemented in digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs), etc.

While the exemplary embodiments have been particularly shown and described with reference to the drawings, it will be understood by those of ordinary skill in the art that various changes in form and details may be made therein without departing from the spirit and scope of the present inventive concept as defined by the following claims.

What is claimed is:

1. A medical image providing apparatus comprising:
    a display configured to display a first image comprising an object; and
    a processor configured to:
        while the first image is displayed, control to output, on the display, a list comprising items corresponding to a plurality of medical image reconstruction techniques, used to generate a second medical image based on image data of a first region included in the first image,
        receive a selection of a medical image reconstruction technique among the plurality of medical image reconstruction techniques, and
        control to display a second image generated based on the image data of the first image, by applying the selected medical image reconstruction technique to image data of at least a part of the object displayed in the first image.

2. The medical image providing apparatus of claim 1, wherein the plurality of medical image reconstruction techniques comprises at least one of post-processing or reconstruction.

3. The medical image providing apparatus of claim 1, wherein the second image comprises a region of the object included in the first region.

4. The medical image providing apparatus of claim 1, the first region is a partial region of the first image.

5. The medical image providing apparatus of claim 1, wherein the first image is obtained from image data acquired by a computed tomography (CT) protocol.

6. The medical image providing apparatus of claim 1, further comprising an input device,
    wherein the processor is further configured to receive, through the input device, a user input for selecting the first region on the first image.

7. The medical image providing apparatus of claim 1, wherein the processor is further configured to automatically extract a target region for diagnosis from the first image and select the target region as the first region.

8. The medical image providing apparatus of claim 1, wherein the list further comprises at least one additional item obtained or calculated by using image data obtained by scanning for the first image.

9. The medical image providing apparatus of claim 8, wherein the at least one additional item comprises at least one of a cerebral blood volume (CBV) map, a cerebral blood flow (CBF) map, a histogram equalization image, an apparent diffusion coefficient (ADC) map, a trace map, a functional MRI (fMRI) map, a fractional anisotropy map, or a diffusion tractography image.

10. The medical image providing apparatus of claim 1, wherein the plurality of medical image reconstruction techniques comprises at least one of a contrast medium image reconstruction technique or a non-contrast medium image reconstruction technique.

11. The medical image providing apparatus of claim 1, further comprising an input device,
    wherein the processor is further configured to:
        receive, through the input device, a user selection input for selecting medical image reconstruction techniques corresponding to a plurality of first regions included in the first image, respectively, among the plurality of medical image reconstruction techniques, and
        control to display a plurality of second images on the plurality of first regions, respectively,
    the plurality of second images is generated by using the selected medical image reconstruction techniques, respectively,
    the first region is one of the plurality of first regions, and
    the second image is one of the plurality of second images.

12. The medical image providing apparatus of claim 1, wherein the processor is further configured to automatically extract a disease suspected region from the first image and select the disease suspected region as the first region.

13. The medical image providing apparatus of claim 1, wherein the processor is further configured to additionally output a sub-list comprising a reconstructed image according to a point in time, the reconstructed image corresponding to one of the items included in the list.

14. The medical image providing apparatus of claim 1, wherein the first region is a partial region of the first image,
    the second image is displayed in the partial region,
    the first image is an image of a first type different from a second type of an image which is the second image, and
    based on a user request, the processor is further configured to:
        change the second type of the image displayed in the partial region to be the first type,
        change the first type of the image displayed outside of the partial region to be the second type,
        control to display the image of the second type outside the partial region, and
        control to display the image of the first type in the partial region, so that the first type of the image and the second type of the image are mutually switched,
        wherein the image of the first type displays the at least the part of the object in the partial region.

15. The medical image providing apparatus of claim 1, wherein the second image is displayed overlaid on the first region,
    the processor is further configured to:
        based on receiving a selection of a second region included in the first image, receive a selection of another medical image reconstruction technique among the plurality of medical image reconstruction techniques, and
        control to display another second image generated by applying the another medical image reconstruction technique to image data of the second region, by overlaying the another second image on the second region of the first image, and an image type of the another second image overlaid on the second region is different from an image type of the second image.

16. A computer program product comprising a non-transitory computer-readable recording medium, the non-transitory computer-readable recording medium comprising instructions which, when executed by a processor, cause the processor to execute a method including:
  displaying a first image comprising an object;
  while the first image is displayed, displaying a list comprising items corresponding to a plurality of medical image reconstruction techniques, respectively, for generating a plurality of second images, respectively, based on image data of a first region included in the first image;
  receiving a selection of a medical image reconstruction technique among the plurality of medical image reconstruction techniques; and
  displaying a second image among the plurality of second images that is generated based on the image data of the first image, by applying the medical image reconstruction technique to image data of at least a part of the object displayed in the first image.

17. The computer program product of claim 16, wherein the plurality of medical image reconstruction techniques comprises at least one of post-processing or reconstruction.

18. The computer program product of claim 16, wherein the second image comprises a region of the object included in the first region.

* * * * *